United States Patent
Pasquale et al.

(10) Patent No.: US 8,461,119 B2
(45) Date of Patent: Jun. 11, 2013

(54) AGENTS THAT MODULATE EPH RECEPTOR ACTIVITY

(75) Inventors: Elena B. Pasquale, San Diego, CA (US); Mitchell Koolpe, San Diego, CA (US); Keith K. Murai, Candiac (CA)

(73) Assignee: The Burnham Institute, La Jolla, CA (US)

( * ) Notice: Subject to any disclaimer, the term of this patent is extended or adjusted under 35 U.S.C. 154(b) by 203 days.

(21) Appl. No.: 10/652,407

(22) Filed: Aug. 29, 2003

(65) Prior Publication Data

US 2004/0180823 A1 Sep. 16, 2004

Related U.S. Application Data

(60) Provisional application No. 60/413,242, filed on Sep. 24, 2002.

(51) Int. Cl.
*A61K 38/10* (2006.01)
*C07K 7/08* (2006.01)

(52) U.S. Cl.
USPC ........ 514/21.5; 514/13.3; 514/18.9; 530/327; 530/402

(58) Field of Classification Search
None
See application file for complete search history.

(56) References Cited

U.S. PATENT DOCUMENTS

| | | | |
|---|---|---|---|
| 5,512,457 | A | 4/1996 | Lyman et al. |
| 5,516,658 | A | 5/1996 | Beckmann et al. |
| 5,624,899 | A | 4/1997 | Bennett et al. |
| 5,627,267 | A | 5/1997 | Lyman et al. |
| 5,650,504 | A | 7/1997 | Bartley et al. |
| 5,716,934 | A | 2/1998 | Bartley et al. |
| 5,738,844 | A | 4/1998 | Beckmann et al. |
| 5,795,734 | A | 8/1998 | Flanagan et al. |
| 5,798,448 | A | 8/1998 | Caras et al. |
| 5,824,303 | A | 10/1998 | Bartley et al. |
| 6,001,964 | A | 12/1999 | Gaynor et al. |
| 6,864,227 | B1 | 3/2005 | Wang et al. |
| 2004/0247592 | A1 | 12/2004 | Roifman et al. |

FOREIGN PATENT DOCUMENTS

| | | |
|---|---|---|
| CA | 2329270 | 5/1999 |
| CA | 2461898 | 9/2002 |
| WO | WO 90/00192 | 1/1990 |
| WO | WO 94/11020 | 5/1994 |
| WO | WO 95/06065 | 3/1995 |
| WO | WO 96/01839 | 1/1996 |
| WO | WO 96/02645 | 2/1996 |
| WO | WO 96/09384 | 3/1996 |
| WO | WO 96/10911 | 4/1996 |
| WO | WO 96/13518 | 5/1996 |
| WO | WO 96/17925 | 6/1996 |
| WO | WO 96/23000 | 8/1996 |
| WO | WO 96/26958 | 9/1996 |
| WO | WO 96/36713 | 11/1996 |
| WO | WO 97/36919 | 10/1997 |
| WO | WO 99/08696 | 2/1999 |
| WO | WO 99/10495 | 3/1999 |
| WO | WO 99/45121 | 9/1999 |
| WO | WO 99/52541 | 10/1999 |
| WO | WO 99/67285 | 12/1999 |
| WO | WO 00/30673 | 6/2000 |
| WO | WO 00/37500 | 6/2000 |
| WO | WO0108636 A2 * | 2/2001 |
| WO | WO 02/26827 | 4/2002 |
| WO | WO 2004/028551 | 4/2004 |
| WO | WO 2004/080425 | 9/2004 |
| WO | WO 2004/091375 | 10/2004 |
| WO | WO 2006/081418 | 8/2006 |

OTHER PUBLICATIONS

Appendix A is the sequence of rat IgG-2B C region. Underlined is the hydrophobic motif. 2 pages.*
Appendix B is a dictionary definition of 'ligand.'*
Ogawa et al. (2000). Oncogene. 19, 6043-6052.*
Toth et al (2001). Dev. Cell. 1, 83-92.*
Bork, A. Powers and pitfalls in sequence analysis: the 70% hurdie. Genome Res 102 398-400, 2000.*
Skolnick et al. From genes to protein structure and function: novel applications of computational approaches in the genomicera. Trends in Biotech 18(1): 34-39, 2000.*
Doerks et al. Protein annotation'. detective work for function prediction. Trends in Genetics 14(6): 248-250, 1998.*
Smith et al. The challenges of genome sequence annotation or "The devil is in the details". Nature Biotech 15: 1222-1223,1997.*
Brenner, S.E. Errors in genome function. Trends in Genetics 15(4): 132-133, 1999.*
Bork et al. Go hunting in sequence databases but watch out for the traps. Trends in Genetics. 12410): 425-427, 1996.*
Kropinski (2000). Accession No. NP_061584. p. 1.*
Chang et al(1986). Accession No. P01153. p. 1.*
Fumoleau et al (1997). Expert opin Investig Drugs. 6, 1853-65. Abstract only.*
Hill et al. (1996). Mol Microbiol. 20, 685-92. Abstract only.*
Dybwad et al. (1996). Annals of Rheumatoid Disease. 55, 437-441.*
Rogers et al. (2000). JMB. 304, 911-926.*
Rivkin et al. (2000). Molecular Reproduction and Development. 56, 401-411.*
Andres, A.C. et al. 1994 "Expression of two novel *eph*-related receptor protein tyrosine kinases in mammary gland development and carcinogenesis," Oncogene 9: 1461-1467.
Arap, W. et al. 2002 "Cancer treatment by targeted drug delivery to tumor vasculature in a mouse model," *PNAS USA* 99:1527-1531.
Arap, W. et al. 1998 "Targeting the prostate for destruction through a vascular adress," *Science* 279:377-380.
Carles-Kinch, K. et al. 2002 "Antibody targeting of the EphA2 tyrosine kinase inhibits malignant cell behavior," *Cancer Res.* 62:2840-2847.
Daniel, T.O. et al. 1996 "ELK and LERK-2 in developing kidney and microvascular endothelial assembly," *Kidney Int. Suppl.* 57:S73-S81.

(Continued)

*Primary Examiner* — Robert C Hayes
(74) *Attorney, Agent, or Firm* — Knobbe, Martens, Olson & Bear, LLP

(57) ABSTRACT

Novel agents are described that bind to Eph receptors. Methods of using these agents to modulate the activity of Eph receptors, stimulate apoptosis, and deliver therapeutic agents are also described. Methods of screening for agents capable of selectively binding to Eph receptors are also described.

11 Claims, 21 Drawing Sheets

OTHER PUBLICATIONS

Devlin, J.J. et al. 1990 "Random peptide libraries: a source of specific protein binding molecules," *Science* 249:404-406.

Dodelet, V.C. et al. 2000 "Eph receptors and ephrin ligands: embryogenesis to tumorigenesis," *Oncogene* 19:5614-5619.

Dohn, M. et al. 2001 "Receptor tyrosine kinase EphA2 is regulated by p53-family proteins and induces apoptosis," *Oncogene* 20:6503-6515.

Dottori, M. et al. 1998 "EphA4 (Sek1) receptor tyrosine kinase is required for the development of the corticospinal tract," *PNAS USA* 95:13248-13253.

Dvorak, H.F. et al. 1988 "Identification and characterization of the blood vessels of solid tumors that are leaky to circulating macromolecules," *Am. J. Pathol.* 133:95-109.

Easty, D.J. et al. 1995 "Abnormal protein tyrosine kinase gene expression during melanoma progression and metastasis," *Int. J. Cancer* 60:129-136.

Eberhart, J. et al. 2002 "EphA4 constitutes a population-specific guidance cue for motor neurons," *Dev.Biol.* 247:89-101.

Ellerby, H.M. et al. 1999 "Anti-cancer activity of targeted pro-apoptotic peptides," *Nat. Med.* 5:1032-1038.

Ellis, J. et al. 1995 "Embryo brain kinase: a novel gene of the eph/elk receptor tyrosine kinase family," *Mechanisms Devel.* 52:319-341.

Eph Nomenclature Committee. 1997 "Unified nomenclature for Eph family receptors and their ligands, the ephrins," *Cell* 90:403-404.

Essler, M. et al. 2002 "Molecular specialization of breast vasculature : a breast-homing phage-displayed peptide binds to aminopeptidase P in breast vasculature," *PNAS USA* 99:2252-2257.

Flanagan, J.G. et al. 1998 "The ephrins and Eph receptors in neural development." *Ann. Rev. Neurosci.* 21:309-345.

Ganju, P. et al. 1994 "The Eck receptor tyrosine kinase is implicated in pattern formation during gastrulation, hindbrain segmentation and limb development," *Oncogene* 9:1613-1624.

Gerlag, D.M. et al. 2001 "Suppression of murine collagen-induced arthritis by targeted apoptosis of synovial neovasculature," *Arthritis Res.* 3:357-361.

Hess, A.R. et al. 2001 "Molecular regulation of tumor cell vasculogenic mimicry by tyrosine phosphorylation : role of epithelial cell kinase (Eck/EphA2)[1]," *Cancer Res.* 61:3250-3255.

Himanen, J.P. et al. 1998 "Crystal structure of the ligand-binding domain of the receptor tyrosine kinase EphB2," *Nature* 396:486-491.

Himanen, J.P. et al. 2001 "Crystal structure of an Eph receptor-ephrin complex," *Nature* 414:933-938.

Koivunen, E. et al. 1999 "Tumor targeting with a selective gelatinase inhibitor," *Nat. Biotechnol.* 17:768-774.

Koivunen, E. et al. 1994 "Isolation of a highly specific ligand for the $\alpha_5\beta_1$ integrin from a phage display library," *J. Cell Biol.* 124:373-380.

Koolpe, M. et al. 2002 "An Ephrin Mimetic Peptide That Selectively Targets the EphA2 Receptor," *J. Biol. Chem.* 277:46974-46979.

Kullander, K. et al. 2002 "Mechanisms and functions of Eph and ephrin signaling," *Nat. Rev. Mol. Cell Biol.* 3:475-486.

Labrador, J. P., et al. 1997 "The n-terminal globular domain of Eph receptors is sufficient for ligand binding and receptor signaling," *EMBO J.* 16:3889-3897.

Manning, G. et al. 2002 "Evolution of protein kinase signaling from yeast to man," *Trends Biochem. Sci.* 27:514-520.

McBride, J.L. et al. 1998 "Ephrin-A1 is expressed at sites of vascular development in the mouse," *Mech. Dev.* 77:201-204.

McLennan, R. et al. 2002 "Ephrin-as cooperate with EphA4 to promote trunk neural crest migration," *Gene Exp.* 10:295-305.

Miao, H. et al. 2001 "Activation of EphA receptor tyrosine kinase inhibits the Ras/MAPK pathway," *Nature Cell Biol.* 3:527-530.

Miranda, J.D. et al. 1999 "Induction of Eph B3 after spinal cord injury," *Exp. Neurol.* 156:218-222.

Mori, T. et al. 1995 "Differential expressions of the eph family of receptor tyrosine kinase genes (sek, elk, eck) in the developing nervous system of the mouse," *Brain Res. Mol. Brain Res.* 29:325-335.

Mori, T. et al. 1995 "Localization of novel receptor tyrosine kinase genes of the eph family, MDK1 and its splicing variant, in the developing mouse nervous system," *Brain Res. Mol. Brain Res.* 34:154-160.

Murai, K.K. et al. 2003 "Targeting the EphA4 receptor in the nervous system with biologically active peptides," *Mol. Cell. Neurosci.* 24:1000-1011.

Murai, K.K. et al. 2003 "Control of hippocampal dendritic spine morphology through ephrinA3/EphA4 signaling," *Nat. Neurosci.* 6:153-160.

Murai, K.K. et al. 2003 "'Eph'ective signaling: forward, reverse, and crosstalk," *J. Cell. Sci.* 116:2823-2832.

Myers, C. et al. 2000 "Homeobox B3 promotes capillary morphogenesis and angiogenesis," *J. Cell Biol.* 148:343-351.

Nemoto, T. et al. 1997 "Overexpression of protein tyrosine kinases in human esophageal cancer," *Pathobiology* 65:195-203.

Nieto, M.A. et al. 1992 "A receptor protein tyrosine kinase implicated in the segmental patterning of the hindbrain and mesoderm," *Development* 116: 1137-1150.

Ogawa, K. et al. 2000 "The ephrin-A1 ligand an dits receptor, EphA2, are expressed during tumor neovascularization," *Oncogene* 19: 6043-6052.

Ohta, K. et al. 1996 "The receptor tyrosine kinase, Cek8 is transiently expressed on subtypes of motoneurons in the spinal cord during development," *Mech. Devel.* 54: 59-69.

Olivieri, G. et al. 1999 "Immunohistochemical localization of EphA5 in the adult human central nervous system," *J. Histochem. Cytochem.* 47:855-861.

Olson, T. A. et al. 1997 "Targeting the tumor vasculature : inhibition of tumor growth by a vascular endothelial growth factor-toxin conjugate," *Int. J. Cancer* 73:865-870.

Pandey, A. et al. 1995 "Role of B61, the ligand for the Eck receptor tyrosine kinase, in TNF—induced angiogenesis," *Science* 268:567-569.

Prevost, N. et al. 2002 "Interactions between Eph kinases and ephrins provide a mechanism to support platelet aggregation once cell-to-cell contact has occurred," *PNAS USA* 99:9219-9224.

Ruiz, J. C. et al. 1994 "The expression of the receptor-protein tyrosine kinase gene, eck, is highly restricted during early mouse development," *Mech. Dev.* 46:87-100.

Smith, G. P. 1985 "Filamentous fusion phage: novel expression vectors that display cloned antigens on the virion surface," *Science* 228:1315-1317.

Soans, C. et al. 1994 "Characterization of the expression of the Cek8 receptor-type tyrosine kinase during development and in tumor cell lines," *Oncogene* 9:3353-3361.

Thompson, S.M. 2003 "Ephrins keep dendritic spines in shape," *Nat. Neurosci* 6:103-104.

van der Geer, P. et al. 1994 "Receptor protein-tyrosine kinases and their signal transduction pathways," *Annu. Rev. Cell Biol.* 10:251-337.

Walker-Daniels, J. et al. 1999 "Overexpression of the EphA2 tyrosine kinase in prostate cancer," *Prostate* 41:275-280.

Wang B. Presentation at NIH, Jul. 2002 published on-line at: http://www.niddk.nih.gov/fund/other/genoproteo/wang.pdf.

Willson, C.A. et al. 2002 "Upregulation of EphA receptor expression in the injured adult rat spinal cord," *Cell Transplant* 11:229-239.

Yancopoulos, G.D. et al. 2000 "Vascular-specific growth factors and blood vessel formation," *Nature* 407: 242-248.

Yue, Y. et al. 1999 "Specification of distinct dopaminergic neural pathways: roles of the Eph family receptor EphB1 and ligand ephrin-B2," *J. Neurosci.* 19:2090-2101.

Zantek, N.D. et al. 1999 "E-cadherin regulates the function of the EphA2 receptor tyrosine kinase," *Cell Growth Differ*. 10:629-638.

Zelinski, D.P. et al. 2001 "EphA2 overexpression causes tumorigenesis of mammary epithelial cells," *Cancer Res.* 61: 2301-2306.

Zelinski, D.P. et al. 2002 "Estrogen and Myc negatively regulate expression of the EphA2 tyrosine kinase," *J. Cell. Biochem.* 85:714-720.

Zhang, J.H. et al. 1997 "Dynamic expression suggests multiple roles of the eph family receptor brain-specific kinase (Bsk) during mouse neurogenesis," *Brain Res. Mol. Brain Res.* 47:202-214.

Dail et al., 2006, "Eph receptors inactivate R-Ras through different mechanisms to achieve cell repulsion," J. Cell. Sci. 119(Pt 7):1244-54.

Koolpe et al., 2005, "EphB receptor-binding peptides identified by phage display enable design of an antagonist with ephrin-like affinity," J. Biol. Chem. 280(17):17301-11.

Ogawa et al., 2006, "EphB2 and ephrin-B1 expressed in the adult kidney regulate the cytoarchitecture of medullary tubule cells through Rho family GTPases," J. Cell. Sci. 119(Pt 3):559-70.

Lin, D. et al. (1999) "The carboxyl terminus of b class ephrins constitutes a pdz domain binding motif" The Journal of Biological Chemistry 274:3726-3733.

European Supplemental Partial Search Report from corresponding European application No. EP 03 74 9303.

U.S. Appl. No. 60/647,852, filed Jan. 27, 2005, Pasquale.

Aasland et al., 2002, "Normalization of nomenclature for peptide motifs as ligands of modular protein domains," FEBS Lett., vol. 513(1):141-144.

Adams et al., 2004, "Eph receptors and ephrin ligands. essential mediators of vascular development," Trends Cardiovasc. Med., vol. 10(5):183-188.

Aoki et al., 2004, "EphA receptors direct the differentiation of mammalian neural precursor cells through a mitogen-activated protein kinase-dependent pathway," J. Biol. Chem., vol. 279(31):32643-32650.

Battaglia et al., 2003, "EphB receptors and ephrin-B ligands regulate spinal sensory connectivity and modulate pain processing," Nat. Neurosci. vol. 6(4):339-340.

Batlle et al., 2005, "EphB receptors activity suppresses colorectal cancer progression," Nature, vol. 435:1126-1130.

Bennett et al., 1995, "Molecular cloning of a ligand for the EPH-related receptor protein-tyrosine kinase Htk," Proc. Natl. Acad. Sci. U S A. vol. 92(6):1866-1870.

Blanco et al., 1998, "Formation and stability of beta-hairpin structures in polypeptides," Curr. Opin. Struct. Biol. vol. 8(1):107-111.

Brantley-Sieders et al., 2004, "Eph receptor tyrosine kinases in angiogenesis: from development to disease," Angiogenesis 7(1):17-28.

Brantley-Sieders et al., 2004, "Eph receptor tyrosine kinases in tumor and tumor microenvironment," Curr Pharma. Design, vol. 10:3431-3442.

Chrencik et al., 2006, "Structure and thermodynamic characterization of the EphB4/Ephrin-B2 antagonist peptide complex reveals the determinants for receptor specificity," Structure, vol. 14(2):321-330.

Conover et al., 2000, "Disruption of Eph/ephrin signaling affects migration and proliferation in the adult subventricular zone," Nat. Neurosci., vol. 3(11):1091-1097.

Cwirla et al., 1997, "Peptide agonist of the thrombopoietin receptor as potent as the natural cytokine," Science, vol. 276(5319):1696-1699.

Davis et al., 1994, "Ligands for EPH-related receptor tyrosine kinases that require membrane attachment or clustering for activity," Science, vol. 266(5186):816-819.

Easty et al., 1994, "Cytokine B61 as a growth factor for metastatic melanomas and increasing expression of its receptor ECK during melanoma progression," Proc. Am. Asso. Cancer Mtng. (Abstract 356; 85th Annual Meeting, American Association for Cancer Research, San Francisco, California, Apr. 10-13, 1994).

Easty et al., 1995 "Protein B61 as a new growth factor: expression of B61 and up-regulation of its receptor epithelial cell kinase during melanoma progression," Cancer Res., vol. 55:2528-2532.

Fairbrother et al., 1998, "Novel peptides selected to bind vascular endothelial growth factor target the receptor-binding site," Biochemistry, vol. 37(51):17754-17764.

Fang et al., 2005, "A kinase-dependent role for EphA2 receptor in promoting tumor growth and metastasis," Oncogene, vol. 24:7859-7868.

Gale et al., 1996, "Eph Receptors and Ligands Comprise Two Major Specificity Subclasses and Are Reciprocally Compartmentalized during Embryogenesis," Neuron, vol. 17(1):9-19.

Goldshmit et al., 2004, "Axonal regeneration and lack of astrocytic gliosis in EphA4-deficient mice," J. Neurosci., vol. 24(45):10064-10073.

Hafner et al., 2004, "Differential gene expression of Eph receptors and ephrins in benign human tissues and cancers," Clin. Chem., vol. 50(3):490-499.

Hajduk et al., 1997, "Discovering high-affinity ligands for proteins," Science, vol. 278(5337):497-499.

Himanen et al., 2004, "Repelling class discrimination: ephrin-A5 binds to and activates EphB2 receptor signaling," Nat. Neurosci., vol. 7(5):501-509.

Holash et al., 1995, "Polarized expression of the receptor protein tyrosine kinase Cek5 in the developing avian visual system," Dev. Biol., vol. 172(2):683-693.

Hu et al., 2005, "Genome-wide association study in esophageal cancer using GeneChip mapping 10K array," Cancer Res., vol. 65(7):2542-2546.

Kozlosky et al., 1995, "Ligands for the receptor tyrosine kinases hek and elk: isolation of cDNAs encoding a family of proteins" Oncogene, vol. 10:299-306.

Kuntz, 1992, "Structure-based strategies for drug design and discovery," Science, vol. 257(5073):1078-1082.

Lackmann et al., 1997, "Ligand for EPH-related kinase (LERK) 7 is the preferred high affinity ligand for the HEK Xreceptor," J. Biol. Chem., vol. 272(26):16521-16530.

Lackmann et al., 1998, "Distinct subdomains of the EphA3 receptor mediate ligand binding and receptor dimerization," J. Biol. Chem., vol. 273(32):20228-20237.

Livnah et al., 1996, "Functional mimicry of a protein hormone by a peptide agonist: the EPO receptor complex at 2.8 A," Science, vol. 273(5274):464-471.

Lowman et al., 1998, "Molecular mimics of insulin-like growth factor 1 (IGF-1) for inhibiting IGF-1: IGF-binding protein interactions," Biochemistry, vol. 37(25):8870-8878.

Magal et al., 1996, "B61, a ligand for the Eck receptor protein-tyrosine kinase, exhibits neurotrophic activity in cultures of rat spinal cord neurons," J. Neuroscience Res., vol. 43:735-744.

Meima et al., 1997, "Lerk2 (Ephrin-B1) is a collapsing factor for a subset of cortical growth cones and acts by a mechanism different from AL-1 (Ephrin-A5)" Molecular and Cellular Neuroscience, vol. 9:314-328.

Miao et al., 2000, "Activation of EphA2 kinase suppresses integrin function and causes focal-adhesion-kinase dephosphorylation," Nat. Cell. Biol., vol. 2:62-69.

Miller et al., 1997, "Ligand binding to proteins: the binding landscape model," Protein Sci., vol. 6(10):2166-2179.

Moore et al., 2004, "Morphogenetic movements underlying eye field formation require interactions between the FGF and ephrinB1 signaling pathways," Dev. Cell, vol. 6(1):55-67.

Nakamoto et al., 2002, "Diverse roles for the Eph family of receptor tyrosine kinases in carcinogenesis," Microsc. Res. Tech., vol. 59(1):59-67.

Neidigh et al., 2002, "Designing a 20-residue protein," Nat. Struct. Biol., vol. 9(6):425-430.

Nikolova et al., 1998, "Cell-type specific and estrogen dependent expression of the receptor tyrosine kinase EphB4 and its ligand ephrin-B2 during mammary gland morphogenesis," J. Cell Sci., vol. 111:2741-2751.

Noren et al., 2004, "Interplay between EphB4 on tumor cells and vascular ephrin-B2 regulates tumor growth," Proc. Natl. Acad. Sci. U S A. vol. 101(15):5583-5588.

Office Action, dated Dec. 14, 2007, U.S. Appl. No. 11/342,247, filed Jan. 26, 2006.

Office Action, dated Jun. 6, 2007, U.S. Appl. No. 11/342,247, filed Jan. 26, 2006.

Prevost et al., 2005, "Eph kinases and ephrins support thrombus growth and stability by regulating integrin outside-in signaling in platelets," Proc. Natl. Acad. Sci., vol. 102(28):9820-9825.

Salvucci et al., 2006, "EphB2 and EphB4 receptors forward signaling promotes SDF-1-induced endothelial cell chemotaxis and branching remodeling," Blood, vol. 108(9):2914-2922.

Smith et al., 2004, "Dissecting the EphA3/Ephrin-A5 interactions using a novel functional mutagenesis screen," J. Biol. Chem., vol. 279(10):9522-9531.

Song et al., 2002, "Solution structure and backbone dynamics of the functional cytoplasmic subdomain of human ephrin B2, a cell-surface ligand with bidirectional signaling properties," Biochemistry X41(36):10942-10949.

Stein et al., 1998, "Eph receptors discriminate specific ligand oligomers to determine alternative signaling complexes, attachment, and assembly responses," Genes Dev., vol. 12:667-678.

Sturz et al., 2004, "EphB4 signaling is capable of mediating ephrinB2-induced inhibition of cell migration," Biochem. Biophys. Res. Comm., vol. 313:80-88.

Surawska et al., 2004, "The role of Ephrins and Eph receptors in cancer," Cytokine & Growth Factor Reviews, vol. 15:419-433.

Twigg et al., 2004, "Mutations of Ephrin-B1 (EFNB1), a marker of tissue boundary formation, cause craniofrontonasal syndrome," Proc. Natl. Acad. Sci. U S A., vol. 101(23):8652-8657.

Walker-Daniels et al., 2003, "Differential regulation of EphA2 in normal and malignant cells," Am. J. Pathol., vol. 162(4):1037-1042.

Wang et al., 1998, "Molecular distinction and angiogenic interaction between embryonic arteries and veins revealed by ephrin-B2 and its receptor Eph-B4," Cell, vol. 93:741-753.

Wang et al., 1998, "Molecular distinction and angiogenic interactions between embryonic arteries and veins revealed by EphrinB2 and its receptor EphB4," Abstracts from 71st Scientific Sessions, Nov. 8-11, 1998; Dallas, Texas; Circulation, vol. 98(17): Abstract 341.

Wieland et al., 2004, "Mutations of the Ephrin-B1 gene cause craniofrontonasal syndrome," Am. J. Hum. Genet., vol. 74(6):1209-1215.

Wrighton et al., 1996, "Small peptides as potent mimetics of the protein hormone erythropoietin," Science, vol. 273(5274):458-463.

Yancopoulos et al., 1998, "Vasculogenesis, Angiogenesis, and growth factors: ephrins enter the fray at the border," Cell, vol. 93:661-664.

Zhou, R., 1998, "The Eph family receptors and ligands," Pharmacol. Ther., vol. 77(3):151-181.

* cited by examiner

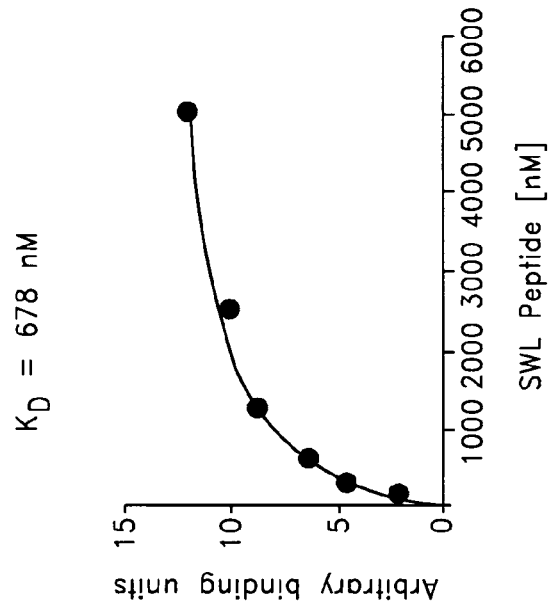
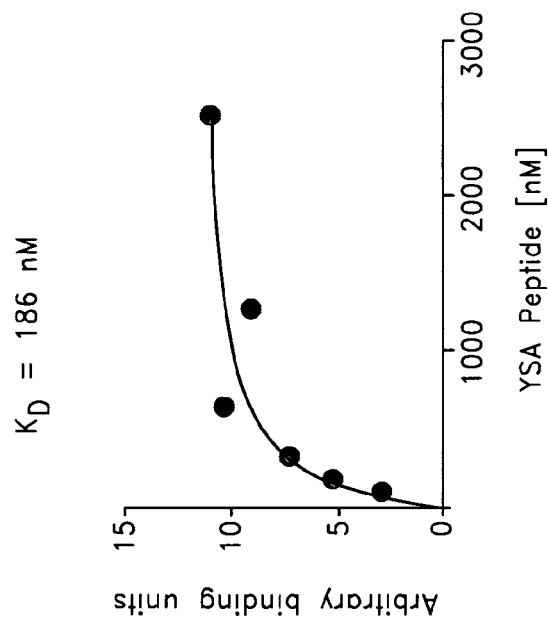
FIG. 3A
FIG. 3B

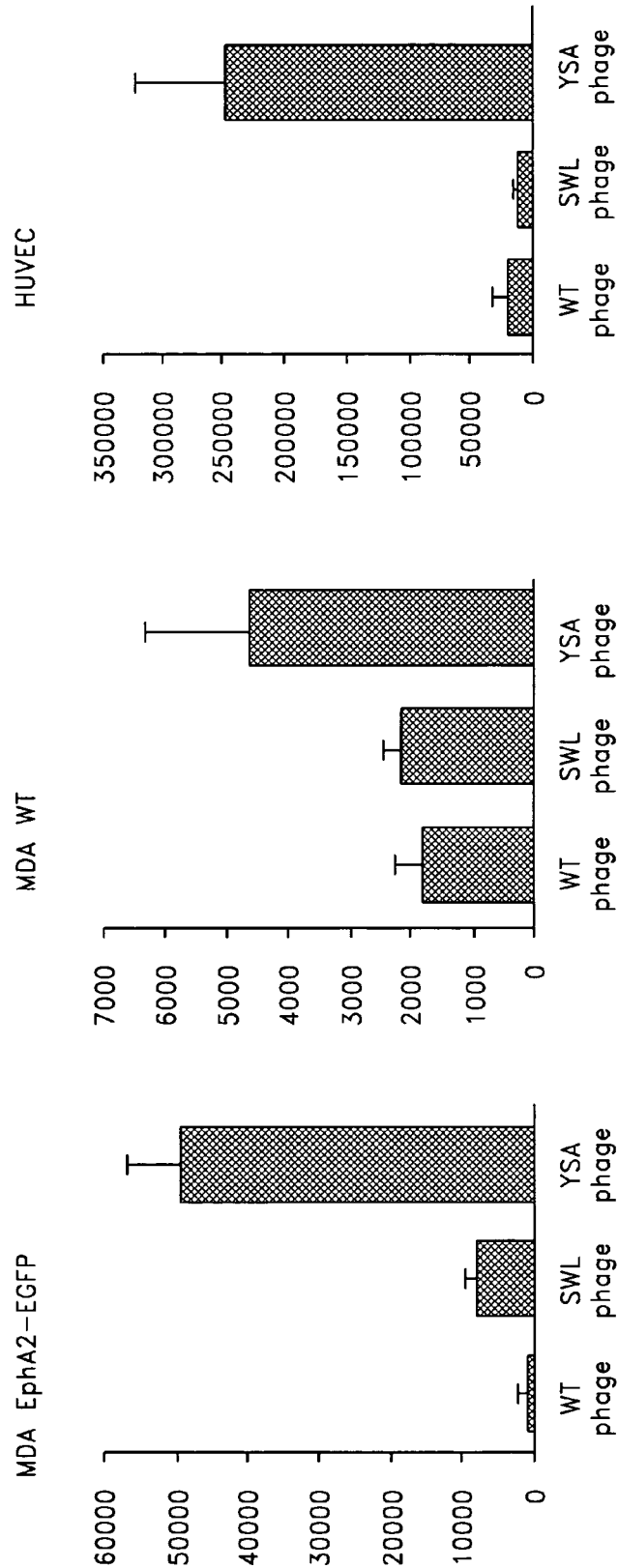

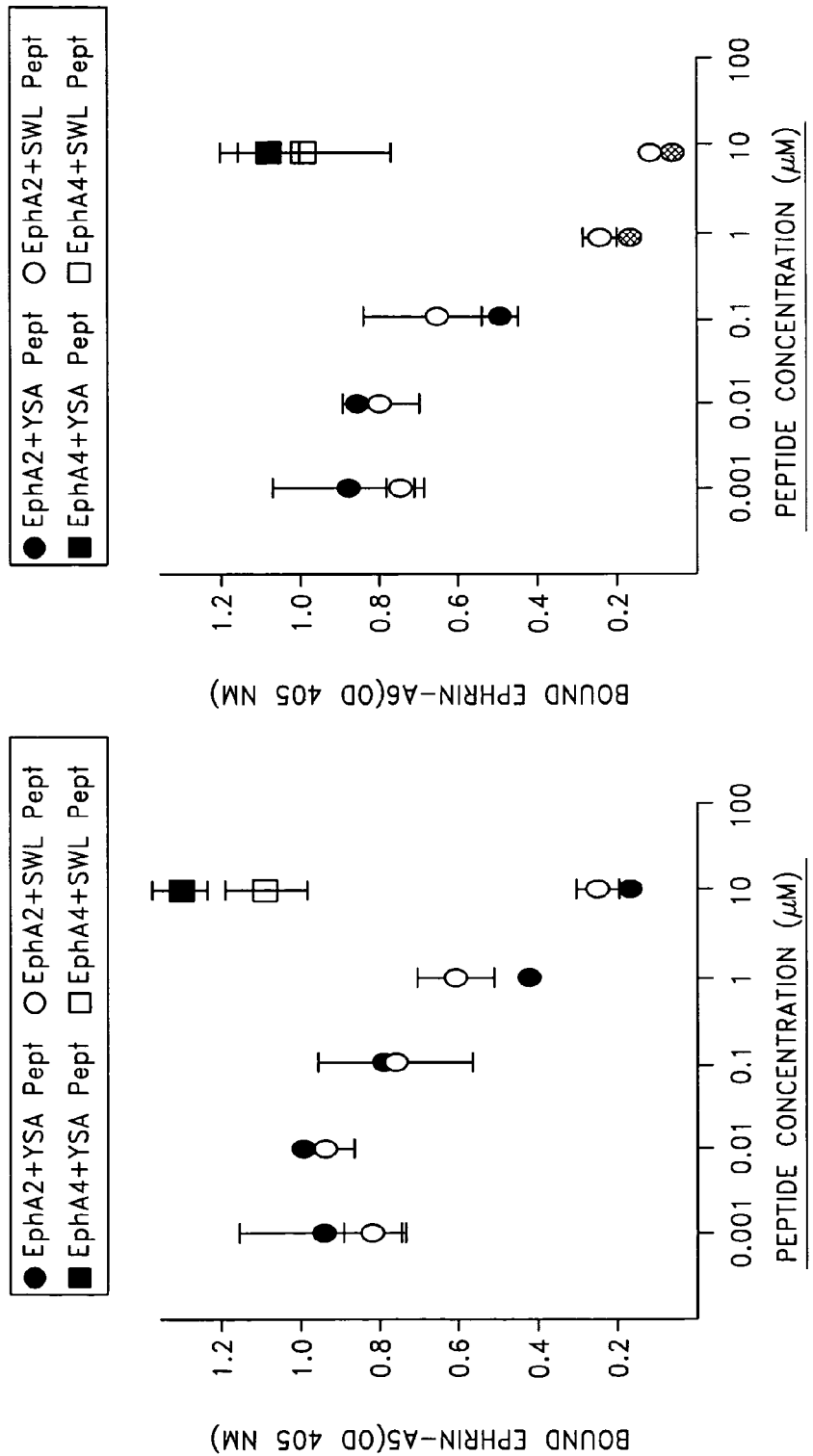

G-H LOOP

| | | |
|---|---|---|
| SWL peptide | SWLAYRGAVSYR | SEQ ID NO: 1 |
| YSA peptide | YSAYPDSVPMMS | SEQ ID NO: 2 |
| hEphrin-A3 | RYSAFSLGYEFHA | SEQ ID NO: 3 |
| A3 peptide | YSAFSLGYEFHA | SEQ ID NO: 4 |
| hEphrin-A2 | LETPFSLGFEERP | SEQ ID NO: 5 |
| hEphrin-A5 | LETPFSLGFEERP | SEQ ID NO: 6 |
| cEphrin-A6 | RETRFSLGFEERP | SEQ ID NO: 7 |
| hEphrin-A1 | RETRFTLGKEFKE | SEQ ID NO: 8 |
| hEphrin-A4 | RETRFSLGFEFLP | SEQ ID NO: 9 |

FIG. 9A

| | A-A' β-STRAND | |
|---|---|---|
| SWL reverse | RYSVAGPYALWS | SEQ ID NO: 10 |
| YSA reverse | SMMPVSDPYASY | SEQ ID NO: 11 |
| hEphrin-A5 | GSKAVADRYAVYW | SEQ ID NO: 12 |
| A5 peptide | KAVADRYAVYW | SEQ ID NO: 13 |
| hEphrin-A2 | AARANADRYAVYW | SEQ ID NO: 14 |
| hEphrin-A4 | LRGGSSLRHVVYW | SEQ ID NO: 15 |
| hEphrin-A1 | CSLAAADRHTVFW | SEQ ID NO: 16 |
| hEphrin-A3 | PGGALGNRHAVYW | SEQ ID NO: 17 |
| cEphrin-A6 | PPPVRGRRHGVYW | SEQ ID NO: 18 |

FIG.9B

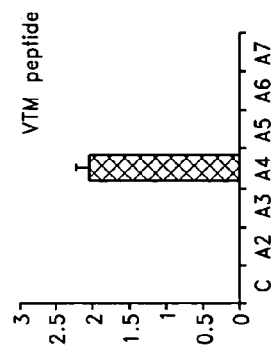
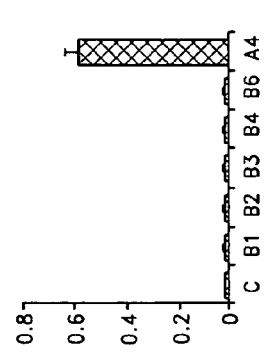
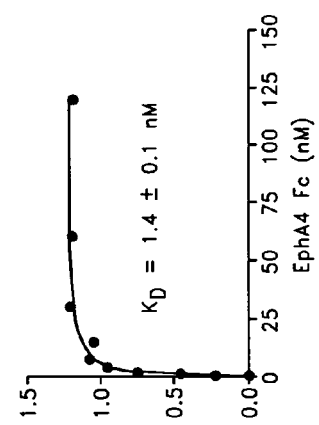
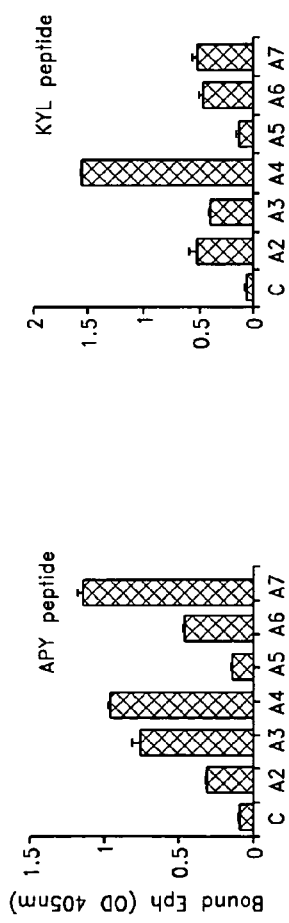
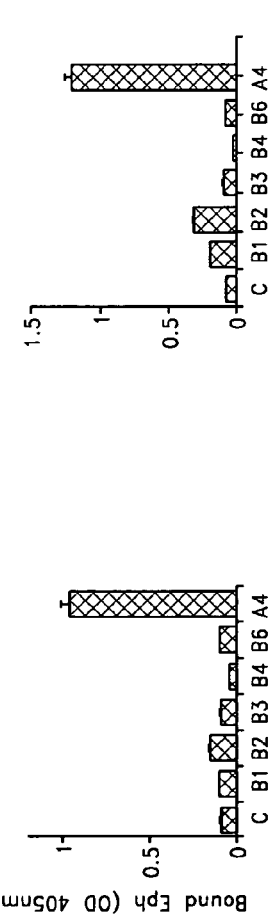
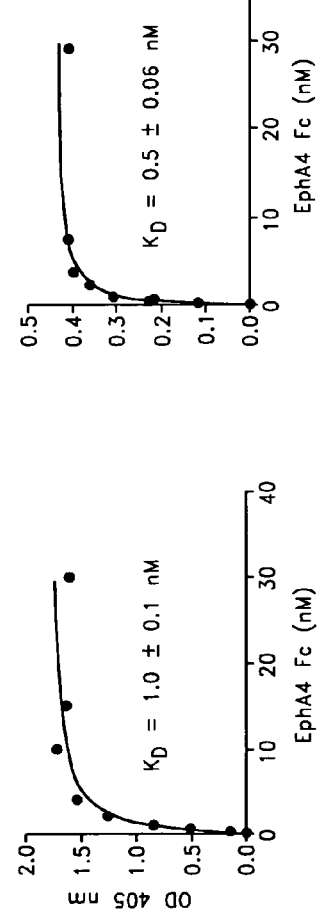

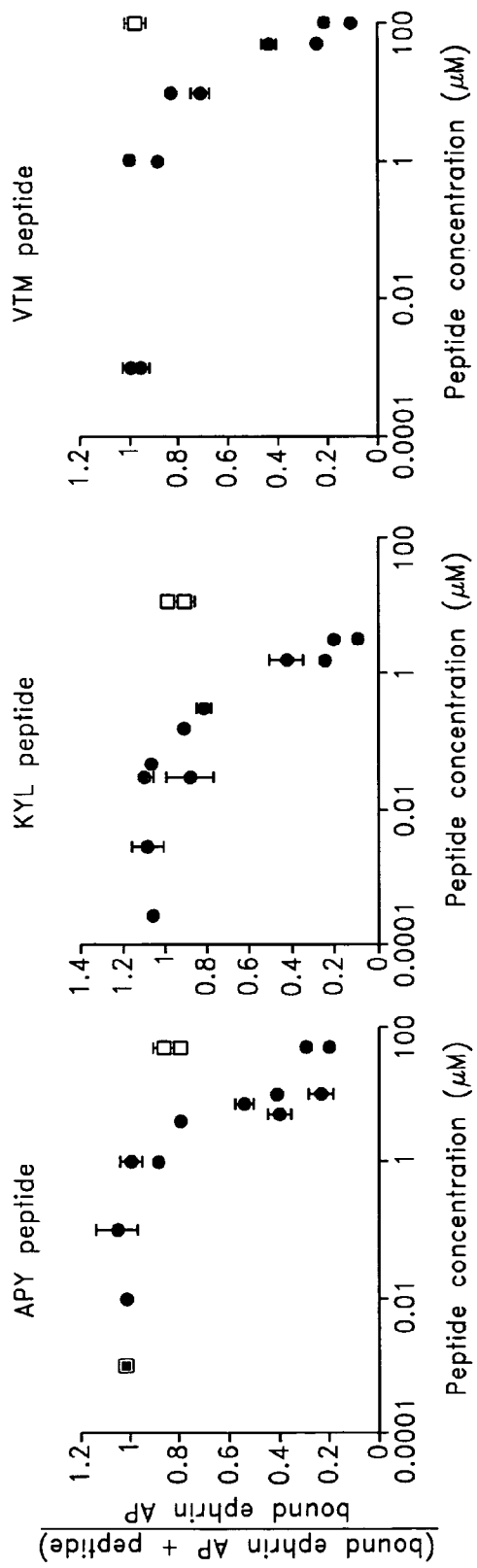

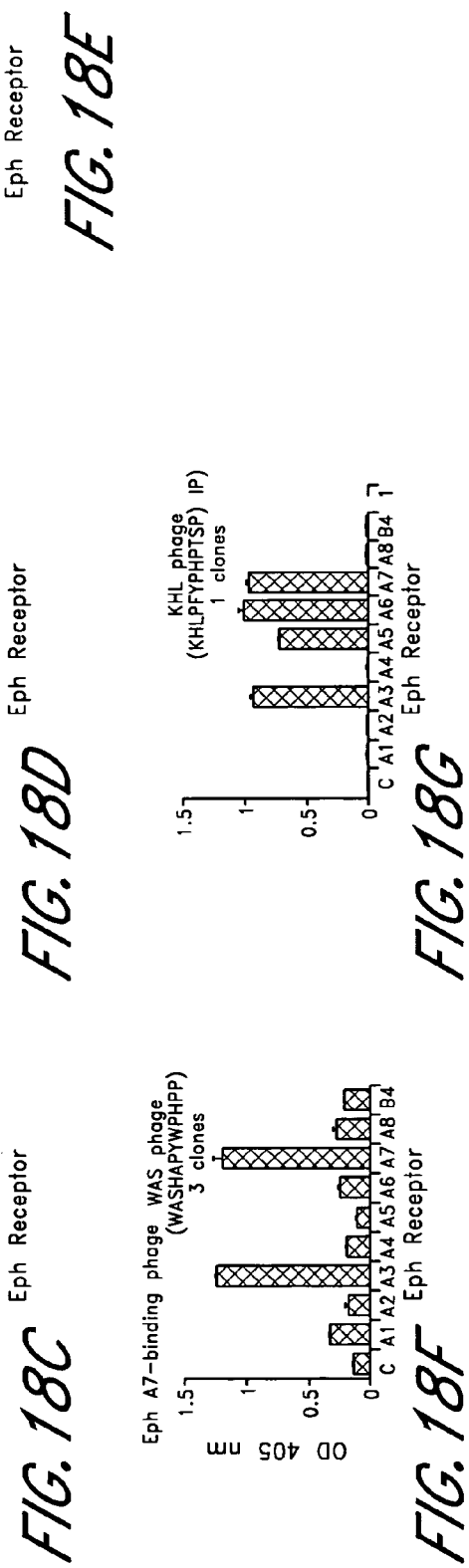

| | ΦXXΦ | synthetic peptide | SEQ ID NO |
|---|---|---|---|
| hEphrin-A1 | QRFTPFTLGKEFKEG | | 63 |
| hEphrin-A2 | QLFTPFSLGFEFRPG | | 64 |
| hEphrin-A3 | QRYSAFSLGYEFHAG | | 65 |
| hEphrin-A4 | QRFTPFSLGFEFLPG | | 66 |
| hEphrin-A5 | QLFTPFSLGFEFRPG | | 67 |
| cEphrin-A6 | QRFTPFSLGFEFRPG | | 68 |
| EphA2 | SWLAYPGAVSYR | *** | 1 |
| EphA2 | YSAYPDSVPMMS | *** | 2 |
| EphA4 | APYCVYRGSWSC | *** | 20 |
| EphA4 | KYLPYWPVLSSL | *** | 21 |
| EphA5 | WDCNGPYCHWLG | | 28 |
| EphA5 | WTFPVLWDDKHP | | 29 |
| EphA5 | SLRDTYMRAKVL | | 27 |
| EphA7 | KHLPFYPHPTSP | | 62 |
| EphA7 | WASHAPYWPHPP | | 61 |
| | ΦXXXΦ | | |
| | ΦXXXXΦ | | |
| hEphrin-B1 | QEFSPNYMGLEFKKH | | 69 |
| hEphrin-B2 | QEFSPNLWGLEFQKN | | 70 |
| hEphrin-B3 | QEYSPNLWGHEFRSH | | 71 |
| EphA4 | VTMEAINLAFPG | *** | 22 |
| EphB2 | SHWPISPYSLLS | *** | 47 |
| EphB2 | DHWRVSPYSLLY | | 48 |
| EphB2 | DHWRILPFSLSS | *** | 50 |
| EphB2 | SHWPVLPFAHWQ | | 51 |
| EphB2 | IHWPVAPSYSYLD | | 52 |
| EphB2 | WHWTIEPFAITS | *** | 54 |
| EphB2 | DHWYYTPWQPIE | | 56 |
| EphB2 | NHWPTQPYAIPI | | 57 |
| EphB2 | DHWPLLPYALAH | | 59 |
| EphB2 | WPPHWPRSLDYA | | 58 |
| EphB2 | WHRYPDPRMLPT | | 53 |
| EphB2 | SNEWIQPRLPQH | *** | 49 |
| EphB4 | EFFTWRPTYYGI | | 42 |
| EphB4 | EWYMKFPPEHYF | | 37 |
| EphB4 | FSPQGPAARNFA | | 45 |
| EphB4 | TNYLFSPNGPIA | *** | 34 |
| EphB4 | DHNHNLYNPWRL | | 44 |
| EphB4 | DHNHDLYNPWRL | *** | 33 |
| EphB4 | TYFDFQAWSIRA | | 36 |
| EphB4" | DALNDWLLFRPW | *** | 23 |
| EphB4/EphB4" | GPVADAWLVYPR | | 31 |
| EphB4 | GPVHRAWEPTSH | | 38 |
| EphB4 | GPVERAWRPDLI | | 43 |
| EphB4 | GPVSKAWQETET | | 41 |
| EphB4 | LPHGPVAAAWDA | | 35 |
| EphB4 | SHVGPIMRAWAP | | 39 |
| EphB4 | NPVIGPIQRAWT | *** | 32 |
| EphB4 | WGIPRAAQVMWT | | 40 |
| EphB4" | IPWTQHMAMSPM | *** | 24 |
| Peptides that cannot be aligned | | | |
| EphB4"/EphA | SVSVGMKPSPRP | *** | 25 |
| EphB2 | THWCHLLNCAAL | | 55 |
| EphB4" | SGHQLLLNKMPN | | 26 |
| EphB2 | RNKRIRMQLPMI | | 60 |

FIG. 19

AGENTS THAT MODULATE EPH RECEPTOR ACTIVITY

RELATED APPLICATIONS

This Application claims the benefit of priority under 35 U.S.C. §119 of the U.S. Provisional Application No. 60/413,242 filed Sep. 24, 2002, and which is expressly incorporated herein by reference in its entirety.

GOVERNMENTAL INTERESTS

This invention was made with government support under grant numbers CA82713 and NS43029 awarded by the National Institutes of Health and grant number DAMD17-01-1-0168 awarded by the Department of Defense. The United States Government has certain rights in this invention.

FIELD OF THE INVENTION

The present invention pertains to novel ligands that modulate Eph receptor function.

DESCRIPTION OF THE RELATED ART

The Eph receptors comprise a large family of closely related transmembrane tyrosine kinases that actively signal when bound to their ephrin ligands (Flanagan & Vanderhaeghen 1998 *Ann Rev Neurosci* 21:309-345; Manning et al. 2002 *Trends Biochem Sci* 27:514-520; Murai, K. & Pasquale, E. 2003 *J. Cell Sci* 116:2823-2832). The sixteen Eph receptors are divided into two subgroups (EphA and EphB) based on sequence homology. EphA receptors bind the GPI-linked ephrin-A ligands, while EphB receptors bind the transmembrane ephin-B ligands.

Originally identified as regulators of neural development, the Eph family of receptor tyrosine kinases and their ephrin ligands are also critical for vascular development and pathological forms of angiogenesis (Flanagan, J. G. & Vanderhaeghen, P. 1998 *Ann Rev Neurosci* 21:309-345; Dodelet, V. C. & Pasquale, E. B. 2000 *Oncogene* 19:5614-5619; Yancopoulos G. D. et al. 2000 *Nature* 407:242-248). For example, the EphA2 receptor and ephrin-A1—a ligand for EphA2—are coordinately expressed in the vasculature of human tumors and mouse xenograft tumors grown from human cancer cells (Ogawa, K. et al. 2000 *Oncogene* 19:6043-6052). The EphA2 receptor plays a critical role in vascular endothelial growth factor (VEGF) and tumor necrosis factor α (TNFα)-induced neovascularization because VEGF and TNFα upregulates ephrin-A1, which causes receptor activation in blood vessels (Pandey, A. et al. 1995 *Science* 268:567-569; Cheng, N. et al. 2002 *Mol Cancer Res* 1: 2-11). Similarly, the Homeobox transcription factor Hox B3 promotes angiogenesis by upregulating ephrin-A1 (Myers, C. et al. 2000 *J Cell Biol* 148:343-351). Furthermore, EphA2 signaling is required for the formation of endothelial capillary tubes in vitro (Ogawa, K. et al. 2000 *Oncogene* 19:6043-6052; Daniel, T. O. et al. 1996 *Kidney Int Suppl* 57: S73-81) and promotes the formation of blood vessel-like structures by melanoma cells (Hess, A. R. et al. 2001 *Cancer Res* 61:3250-3255). The expression of EphA2 appears to be restricted to "activated" adult blood vessels, as this receptor has not been detected in either embryonic or adult quiescent blood vessels (Ogawa, K. et al. 2000 *Oncogene* 19:6043-6052; Ruiz, J. C. & Robertson, E. J. 1994 *Mech Dev* 46:87-100; Ganju, P. et al. 1994 *Oncogene* 9:1613-1624). Ephrin-A1 has also not been detected in adult blood vessels, although it is present in the embryonic vasculature (McBride, J. L. & Ruiz, J. C. 1998 *Mech Dev* 77:201-204).

In addition to being present in tumor endothelial cells, EphA2 and ephrin-A1 are upregulated in the transformed cells of a wide variety of tumors including breast, prostate, colon, skin, and esophageal cancers (Ogawa, K. et al. 2000 *Oncogene* 19:6043-6052; Zelinski, D. P. et al. 2001 *Cancer Res* 61:2301-2306; Walker-Daniels, J. et al. 1999 *Prostate* 41:275-28; Easty, D. J. et al. 1995 *Int J Cancer* 60:129-136; Nemoto, T. et al. 1997 *Pathobiology* 65:195-203). Many factors increase EphA2 expression in cancer cells—including the H-Ras oncogene, E-cadherin, members of the p53 family of transcriptional regulators, DNA damage, and loss of estrogen receptors and c-Myc (Andres, A. C. et al. 1994 *Oncogene* 9:1461-1467; Dohn, M. et al. 2001 *Oncogene* 20:6503-6515; Zelinski, D. P. et al. 2002 *J Cell Biochem* 85:714-720).

Since the tumor vasculature is discontinuous and leaky in nature, it is possible to utilize the upregulation of EphA2 and ephrin-A1 to deliver cancer eradicating agents to both blood vessels and tumor cells (Dvorak, H. F. et al. 1988 *Am J Pathol* 133:95-109). Indeed, systemically administered biological agents can easily penetrate into tumors from the blood circulation (Essler, M. & Ruoslahti, E. 2002 *PNAS USA* 99:2252-2257). Selectively targeting EphA2 and ephrin-A1, however, is a challenging task because these proteins belong to large families of closely related proteins (*Eph-Nomenclature-Committee Unified nomenclature for Eph family receptors and their ligands, the ephrins* 1997 *Cell* 90:403-404).

EphA4 is another member of the Eph family of receptor tyrosine kinases. It has important functions in the developing and adult nervous system. Along with its known expression pattern during neural development (Mori, T. et al. 1995 *Brain Res Mol Brain Res* 29:325-335; Nieto, M. A. et al. 1992 *Development* 116:1137-1150; Ohta, K. et al. 1996 *Mechanisms of Development* 54:59-69; Soans, C. et al. 1994 *Oncogene* 9:3353-3361), EphA4 is expressed in brain regions that show extensive synaptic remodeling (Murai, K. et al. 2003 *Nature Neurosci* 6:153-160). In the adult, EphA4 is enriched in the hippocampus and cortex, two brain structures critical for learning and memory.

EphA5 and EphA7 are two EphA receptors that are closely related to EphA4 but are differentially expressed in the developing and adult nervous system (Ellis, J. et al. 1995 *Mechanisms of Development* 52:319-341; Mori, T. et al 1995 *Brain Res Mol Brain Res* 34:154-160; Olivieri, G. & Miescher, G. C. 1999 *J Histochem Cytochem* 47:855-861; Zhang, J. H. et al 1997 *Brain Res Mol Brain Res* 47:202-214). For example, EphA5 receptor is overexpressed in a number of human gliomas and glioblastoma cell lines (Bruce, V. et al. 1999 *Brain Res* 821:169-176; Miescher, G. C. et al. 1997 *Mol Brain Res* 46:17-24).

EphB2 and EphB4 receptors are both over-expressed in certain tumor tissues. EphB4 overexpression is mainly found in infiltrating ductal breast carcinomas with high grade malignancy (Berclaz, G. et al. 1996 *Biochem Biophys Res Commun* 226:869-875) while EphB2 is overexpressed in a majority of gastric tumors (Kiyuokawa, E. et al. 1994 *Cancer Res* 54:3645-3650). Both receptors are overexpressed in many tumor cell lines as well (Berclaz, G. et al. 1996 *Biochem Biophys Res Commun* 226:869-875; Kiyuokawa, E. et al. 1994 *Cancer Res* 54:3645-3650; Bennett, B. D. et al. 1995 *PNAS USA* 92:1866-1870). Both EphB2 and EphB4 are also upregulated in colon carcinoma tissue (Liu, W. et al. 2002 *Cancer* 94:934-939; Stephenson, S. et al. 2001 *BMC Mol Biol* 2:15-23). In addition, EphB2 and EphB4 are also important for vascular development in the embryo and possibly in tumors (Wang, H. U. et al. 1998 *Cell* 93:741-753; Gerety, S. S. et al. 1999 *Mol Cell* 4:403-414).

Identification of Eph receptor binding peptides with different agonistic and drug targeting activities would have important therapeutic applications. For example, bioactive ephrin mimetic peptides could be used to selectively deliver agents to Eph receptor-expressing tissues and modify Eph signaling in therapies for cancer, pathological angiogenesis, nerve regeneration, and cognitive dysfunction. Other possible applications for identified Eph binding peptides include treatment of chronic pain due to injury (Battaglia, A. A. et al. 2003 *Nature Neurosci* 6:339-340), stimulation of neuroblast proliferation in the adult brain (Conover, J. C. et al. 2000 *Nature Neurosci* 3:1091-1097), and modulation of synaptic plasticity (Murai, K. K., & Pasquale, E. B. 2002 *Neuron* 33:159-162) which is thought to have an important role in learning and memory.

SUMMARY OF THE INVENTION

One embodiment of the present invention is a compound which selectively binds to a member of the Eph receptor family or a subset of these receptors.

Another embodiment of the present invention is an isolated a peptide, a peptidomimetic, or a small molecule which selectively binds to a member of the Eph receptor family or a subset of these receptors.

Another embodiment of the present invention is a method of modulating the activity of an Eph receptor in a cell by contacting the cell with an effective amount of an Eph receptor binding compound that comprises a peptide, a peptidomimetic, or a small molecule that selectively binds to a member of the Eph receptor family. The Eph receptor binding compound can be either an agonist or an antagonist. In certain embodiments, Eph receptors including EphA2, EphA4, EphA5, EphA7, EphB2 and EphB4 can be modulated either in vitro or in vivo.

Another embodiment of the present invention is a method of stimulating programmed cell death (apoptosis) by administering to a mammal an Eph receptor agonist or antagonist in an amount that is sufficient to activate programmed cell death. The Eph receptor agonist or antagonist comprises a peptide, a peptidomimetic, or a small molecule that selectively binds to a member of the Eph receptor family. Eph receptors agonists and antagonists can be delivered to both normal and neoplastic cells. In some embodiments, the agonist stimulates the phosphorylation of an Eph receptor while the antagonist inhibits the phosphorylation of an Eph receptor. In other embodiments, agonists or antagonists inhibit the binding of ephrin ligands to Eph receptors.

Another embodiment of the present invention is a method of stimulating and promoting neural regeneration, and reversing neuronal degeneration due to traumatic injury, mental retardation and neurodegenerative diseases. The method comprises administering to a mammal an amount of an Eph receptor agonist which is effective for stimulating neuronal regeneration in said mammal, wherein said agonist comprises a peptide, a peptidomimetic or a small molecule which selectively binds to a member of the Eph receptor family.

Another embodiment of the present invention is a method of modulating cognitive function by administering to a mammal an amount of an Eph receptor agonist or antagonist which is effective in modulating cognitive function, wherein said agonist or antagonist comprises a peptide, a peptidomimetic or a small molecule which selectively binds to a member of the Eph receptor family.

Another embodiment of the present invention is a method of modifying a blood clotting process by administering to a mammal an amount of an Eph receptor agonist which is effective for modifying the blood clotting process, wherein said agonist comprises a peptide, a peptidomimetic or a small molecule which selectively binds to a member of the Eph receptor family.

A further embodiment of the present invention is a method for delivering a therapeutic agent to a cell. The therapeutic agent is linked to an Eph receptor binding compound that comprises a peptide, a peptidomimetic, or a small molecule that selectively binds to member of the Eph receptor family.

Yet another embodiment of the present invention is a conjugate which comprises a therapeutic agent linked to an Eph receptor binding compound that selectively binds to a member of the Eph receptor family. In some embodiments, the therapeutic agent can be an imaging agent.

Another embodiment of the present invention is a method of identifying an Eph receptor binding compound by panning phage display libraries, which contain phage-encapsulated nucleic acids that encode peptides having random sequences, against immobilized Eph receptors. Phage clones which bind to the immobilized receptors are then identified.

Another embodiment of the present invention is a method of identifying an Eph receptor binding ligand by providing an Eph receptor binding agent bound to an Eph receptor, providing a test compound or library of test compounds, and identifying compounds which are capable of dissociating the Eph receptor binding agent from the Eph receptor. Such compounds identified by this method may be further screened against other Eph receptors and Eph receptor binding agents to identify selective Eph receptor binding ligands.

Other embodiments of the invention provide a method for screening compounds using spectral techniques to determine binding of compounds to an Eph receptor. Compounds may screened by using a combination of Alkaline phosphatase assays, Nuclear Magnetic Resonance (NMR) binding assays, Fluorescence Polarization Assay (FPA) and Computational-Docking studies.

BRIEF DESCRIPTION OF THE DRAWINGS

FIGS. 3A and 3B are line graphs which illustrate the changes in surface plasmon resonance units over the surface of BIACORE biosensor chips coated with EphA2 Fc, measured for various concentrations of YSA peptide (3A) or SWL peptide (3B). Dissociation constants were determined by non-linear regression.

FIGS. 4A-4C are bar graphs which compare the number of wildtype M13 phage (WT), phage displaying the YSA peptide (YSA), and phage displaying the SWL peptide (SWL) bound to MDA-MB-435 human breast cancer cells overexpressing the extracellular and transmembrane domains of EphA2 fused to enhanced green fluorescent protein (MDA EphA2-EGFP) (4A), untransfected MDA-MB-435 cells (MDA WT) (4B), or adherent human umbilical vein endothelial (HUVE) cells (4C).

FIGS. 7A and 7B are graphs which show that the SWL and YSA peptides antagonize binding of ephrin-A5 (7A) and ephrin-A6 (7B) to immobilized EphA2 but not EphA4 in a concentration dependent manner.

FIG. 9A shows the alignment of the sequences of the SWL and YSA peptides, the G-H loop of the A-ephrins, and an "A3 peptide" that was synthesized based on the alignment. Identical amino acids are in dark gray; amino acids with similar characteristics are in light gray.

FIG. 9B shows the alignment of the reverse sequences of the SWL and YSA peptides, the A-A' β-strand of ephrins, and an "A5 peptide" that was synthesized based on the alignment. Identical amino acids are in dark gray; amino acids with similar characteristics are in light gray.

FIG. 12A shows M13 phage displaying random 12-mer peptides bound to EphA4 Fc or BSA (control). FIG. 12E shows phage clones that display peptides beginning with NHW showed preferential binding to EphA4.

FIGS. 13A to 13I are bar graphs showing binding selectivity of synthetic EphA4-binding peptides. FIGS. 13(A-C) are bar graphs showing that biotinylated APY, KYL, and VTM peptides immobilized on streptavidin coated plates captured EphA receptor Fc proteins. FIGS. 13(D-F) are bar graphs showing that all three of these peptides showed a low ability to bind to EphB receptors. FIG. 13 (G-I) are bar graphs showing the relative affinities for binding of dimeric EphA4 Fc to the immobilized peptides.

FIGS. 15A-C are graphs showing that APY (FIG. 15A), KYL (FIG. 15B), and VTM (FIG. 15C) peptides antagonize ephrin-A5 binding to EphA4 in a concentration-dependent manner. (Control peptide, white squares).

FIGS. 18A to 18G are bar graphs showing identification and binding selectivity of EphA5- and EphA7-binding peptides. FIGS. 18A and 18B show M13 phage displaying random 12-mer peptides bound to EphA5 Fc, EphA7 Fc, or BSA (control). FIGS. 18C to 18E show that phage clones isolated by panning on EphA5 display peptides (SLR and WDC) selectively bind to EphA5 while one phage clone (WTF) displays a peptide that binds to both EphA5 and EphA6. The three phage clones isolated by panning on EphA7 display peptides that bind to different subsets of EphA receptors including EphA7 (FIGS. 18F and 18G).

FIG. 19 is the alignment of Eph receptor binding peptides with the G-H loop of A- and B-ephrins.

DETAILED DESCRIPTION

Figure 1A:
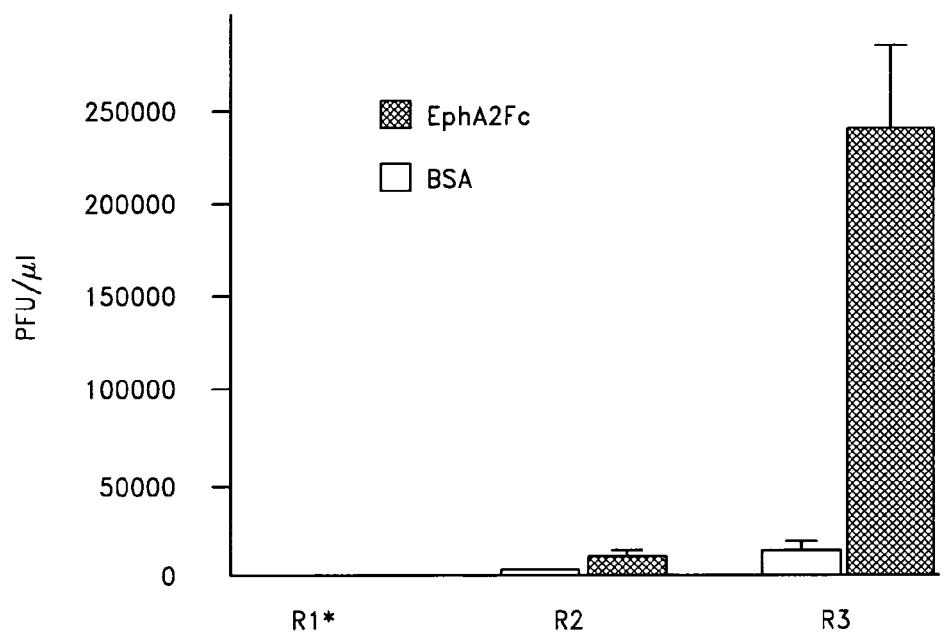
FIG. 1A is a bar graph which shows the titer (pfu/µl) of phage, from a random 12-mer phage display library, obtained over successive rounds of panning (R1-R3) against either immobilized EphA2 Fc or immobilized bovine serum albumin (BSA). Bound phage were eluted with low pH. The peptide sequence of the obtained EphA2-binding clone is shown.

The family of Eph receptor tyrosine kinases represent promising disease targets because they are differentially expressed in pathologic versus normal tissues. For example, the EphA2 receptor is upregulated in transformed cells and tumor vasculature where it likely contributes to the pathogenesis of cancer. EphB4 is overexpressed in a variety of melanomas and carcinomas. EphA4 may play a role in the development of vascular diseases and potentially rheumatoid arthritis (see, Prevost, et al. 2002. *PNAS* 99:9219-9224).

To exploit Eph receptors as therapeutic targets, phage display was used to identify peptides that bind selectively to specific members of the Eph receptor family. A number of such peptides are described herein. For example, peptides have been isolated that selectively bind EphA2 with high affinity (submicromolar $K_D$). Other peptides have been found that selectively bind to EphB2, EphB4, EphA4, EphA5 and EphA7. In some cases the peptides bind a subset of Eph receptors rather than a single receptor. In the case of EphA2, two peptides were found to target the ligand-binding domain of EphA2 and compete with ephrin ligands for binding. These peptides have ephrin-like activity in that they stimulate EphA2 tyrosine phosphorylation and downstream signaling by the receptor. Furthermore, one of the peptides can deliver phage particles to endothelial and tumor cells expressing EphA2. In contrast, peptides corresponding to the receptor-interacting portions of ephrin ligands bind weakly and promiscuously to many Eph receptors. Three EphA4-binding peptides and an EphB2-binding peptide also competed with ephrin ligands for binding to these receptors. However, the peptides did not activate the receptor, and therefore appear to act as antagonists. Bioactive ephrin mimetic peptides can be used to selectively deliver agents to Eph receptor-expressing tissues and modify Eph signaling in therapies for cancer, pathological angiogenesis, and nerve regeneration.

DEFINITIONS

The following definitions are set forth to illustrate and define the meaning and scope of the various terms used to describe the invention herein.

As used herein, "agonist" refers to a biologically active ligand which binds to its complementary biologically active receptor and activates the latter either to cause a biological response in the receptor or to enhance preexisting biological activity of the receptor.

As used herein, "antagonist" refers to a biologically active ligand which binds to its complementary biologically active receptor and inhibits the physiological response of the receptor.

As used herein, "pharmaceutically acceptable salts" refer to the non-toxic alkali metal, alkaline earth metal, and ammonium salts commonly used in the pharmaceutical industry including the sodium, potassium, lithium, calcium, magnesium, barium, ammonium, and protamine zinc salts, which are prepared by methods well known in the art. The term also includes non-toxic acid addition salts, which are generally prepared by reacting the compounds of this invention with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate, and the like.

As used herein, "pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like. For a description of pharmaceutically acceptable acid addition salts as prodrugs, see Bundgaard, H. ed., 1985 *Design of Prodrugs*, Elsevier Science Publishers, Amsterdam.

As used herein, "pharmaceutically acceptable ester" refers to those esters which retain, upon hydrolysis of the ester bond, the biological effectiveness and properties of the carboxylic acid or alcohol and are not biologically or otherwise undesirable. For a description of pharmaceutically acceptable esters as prodrugs, see Bundgaard, H. ed. 1985 *Design of Prodrugs*, Elsevier Science Publishers, Amsterdam. These esters are typically formed from the corresponding carboxylic acid and an alcohol. Generally, ester formation can be accomplished via conventional synthetic techniques. See, for example, March, 1992 *Advanced Organic Chemistry*, 4th Ed., John Wiley & Sons, New York, p. p. 393-396 and references cited therein, and Mark, et al. 1980 *Encyclopedia of Chemical Technology*, John Wiley & Sons, New York. The alcohol component of the ester will generally comprise (i) a $C_2$-$C_{12}$ aliphatic alcohol that can or can not contain one or more double bonds and can or can not contain branched carbons or (ii) a $C_7$-$C_{12}$ aromatic or heteroaromatic alcohols. This invention also contemplates the use of those compositions which are both esters as described herein and at the same time are the pharmaceutically acceptable acid addition salts thereof.

As used herein, "pharmaceutically acceptable amide" refers to those amides which retain, upon hydrolysis of the amide bond, the biological effectiveness and properties of the carboxylic acid or amine and are not biologically or otherwise undesirable. For a description of pharmaceutically acceptable amides as prodrugs, see Bundgaard, H. ed. 1985 *Design of Prodrugs* Elsevier Science Publishers, Amsterdam. These amides are typically formed from the corresponding carboxylic acid and an amine. Generally, amide formation can be accomplished via conventional synthetic techniques. See, for example, March, 1992 *Advanced Organic Chemistry*, 4th Ed., John Wiley & Sons, New York, p. 393 and Mark, et al. 1980 *Encyclopedia of Chemical Technology*, John Wiley & Sons, New York. This invention also contemplates the use of those compositions which are both amides as described herein and at the same time are the pharmaceutically acceptable acid addition salts thereof.

As used herein, "pharmaceutically or therapeutically acceptable carrier" refers to a carrier medium which does not interfere with the effectiveness of the biological activity of the active ingredients and which is not toxic to the host or patient.

As used herein, "stereoisomer" refers to a chemical compound having the same molecular weight, chemical composition, and bonding sequence as another, but having its atoms grouped differently in space about one or more chiral centers. That is, stereoisomers of the same chemical formula will contain identical chemical moieties located in different spacial orientations about at least one chiral center. When pure, stereoisomers have the ability to rotate plane-polarized light. Some pure stereoisomers, however, may have an optical rotation that is so slight that it is undetectable with present instrumentation. The compounds of the instant invention may have one or more asymmetrical carbon atoms and therefore include various stereoisomers. All stereoisomers are included within the scope of the invention.

As used herein, "therapeutically- or pharmaceutically-effective amount" as applied to the compositions of the instant invention refers to the amount of composition sufficient to induce a desired biological result. That result can be alleviation of the signs, symptoms, or causes of a disease, or any other desired alteration of a biological system. In the present invention, the result will, for example, involve inhibition and/or reversal of cancerous cell growth.

As used herein, the terms "peptide compound" and "peptidic structure" are intended to include peptides comprised of naturally-occurring L-amino acids, as well as peptide derivatives, peptide analogues and peptidomimetics of the naturally-occurring L-amino acid structures. The terms "peptide analogue", "peptide derivative" and "peptidomimetic" as used herein are intended to include molecules which mimic the chemical structure of a peptide and retain the functional properties of the peptide. Approaches to designing peptide analogues, derivatives and mimetics are known in the art. For example, see Farmer, P. S. in: *Drug Design* E. J. Ariens, ed. Academic Press, New York, 1980, vol. 10, pp. 119-143; Ball J. B. & Alewood, P. F. 1990 *J Mol Recognition* 3:55; Morgan, B. A. & Gainor, J. A. 1989 *Ann Rep Med Chem* 24:243; and Freidinger, R. M. 1989 *Trends Pharmacol Sci* 10:270; Luthman, et al. 1996 *A Textbook of Drug Design and Development*, 14:386-406, 2nd Ed., Harwood Academic Publishers; Joachim Grante, Angew. 1994 *Chem Int Ed Engl* 33:1699-1720; Fauchere, J. 1986 *Adv Drug Res* 15:29; Veber and Freidinger 1985 *TINS* p. 392; Evans, et al. 1987 *J Med Chem* 30:229, all of which are hereby incorporated by reference. Peptidomimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as naturally-occurring receptor-binding polypeptide, but have one or more peptide linkages optionally replaced by a linkage selected from the group consisting of: $CH_2NH$, $CH_2S$, $CH_2$—$CH_2$, $CH$=$CH$ (cis and trans), $COCH_2$, $CH(OH)CH_2$, and $CH_2SO$, by methods known in the art and further described in the following references: Spatola, A. F. 1983 in: *Chemistry and Biochemistry of Amino Acids,*

*Peptides, and Proteins*, B. Weinstein, eds., Marcel Dekker, New York, p. 267; Spatola, A. F. 1983 *Vega Data*, Vol. 1, Issue 3, *Peptide Backbone Modifications* (general review); Morley, 1980 *Trends Pharm Sci* pp. 463-468, (general review); Hudson, et al. 1979 *Int J Pept Prot Res* 14:177-185 ($CH_2NH$, $CH_2CH_2$); Spatola, et al. 1986 *Life Sci* 38:1243-1249 ($CH_2S$); Hann, 1982 *J Chem Soc Perkin Trans I* 307-314 (CH CH, cis and trans); Almquist, et al. 1980 *J Med Chem* 23:1392-1398, ($COCH_2$); Jennings-White, et al. 1982 *Tetrahedron Lett* 23:2533 ($COCH_2$); Szelke, et al. 1982 European Appln. EP 45665 ($CH(OH)CH_2$); Holladay, et al. 1983 *Tetrahedron Lett* 24:4401-4404 ($C(OH)CH_2$); and Hruby, 1982 *Life Sci* 31:189-199 ($CH_2S$); each of which is incorporated herein by reference. Such peptidomimetics may have significant advantages over polypeptide embodiments, including, for example: more economical production, greater chemical stability, enhanced pharmacological properties (half-life, absorption, potency, efficacy, etc.), altered specificity (for example, a broad-spectrum of biological activities), reduced antigenicity, and others. Labeling of peptidomimetics usually involves covalent attachment of one or more labels, directly or through a spacer (for example, an amide group), to non-interfering position(s) on the peptidomimetic that are predicted by quantitative structure-activity data and/or molecular modeling. Such non-interfering positions generally are positions that do not form direct contacts with the macromolecules(s) (such as, receptor molecules) to which the peptidomimetic binds to produce the therapeutic effect. Derivatization (for example, labeling) of peptidomimetics should not substantially interfere with the desired biological or pharmacological activity of the peptidomimetic. Generally, peptidomimetics of receptor-binding peptides bind to the receptor with high affinity and possess detectable biological activity (i.e., are agonistic or antagonistic to one or more receptor-mediated phenotypic changes).

Systematic substitution of one or more amino acids of a consensus sequence with a D-amino acid of the same type (for example, D-lysine in place of L-lysine) may be used to generate more stable peptides. In addition, constrained peptides comprising a consensus sequence or a substantially identical consensus sequence variation may be generated by methods known in the art (Rizo, et al. 1992 *Ann Rev Biochem* 61:387, incorporated herein by reference); for example, by adding internal cysteine residues capable of forming intramolecular disulfide bridges which cyclize the peptide.

Synthetic or non-naturally occurring amino acids refer to amino acids which do not naturally occur in vivo but which, nevertheless, can be incorporated into the peptide structures described herein. Preferred synthetic amino acids are the D-α-amino acids of naturally occurring L-α-amino acid as well as non-naturally occurring D- and L-α-amino acids represented by the formula $H_2NCHR^5COOH$ where $R^5$ is 1) a lower alkyl group, 2) a cycloalkyl group of from 3 to 7 carbon atoms, 3) a heterocycle of from 3 to 7 carbon atoms and 1 to 2 heteroatoms selected from the group consisting of oxygen, sulfur, and nitrogen, 4) an aromatic residue of from 6 to 10 carbon atoms optionally having from 1 to 3 substituents on the aromatic nucleus selected from the group consisting of hydroxyl, lower alkoxy, amino, and carboxyl, 5)-alkylene-Y where alkylene is an alkylene group of from 1 to 7 carbon atoms and Y is selected from the group consisting of (a) hydroxy, (b) amino, (c) cycloalkyl and cycloalkenyl of from 3 to 7 carbon atoms, (d) aryl of from 6 to 10 carbon atoms optionally having from 1 to 3 substituents on the aromatic nucleus selected from the group consisting of hydroxyl, lower alkoxy, amino and carboxyl, (e) heterocyclic of from 3 to 7 carbon atoms and 1 to 2 heteroatoms selected from the group consisting of oxygen, sulfur, and nitrogen, (f) $C(O)R^2$ where $R^2$ is selected from the group consisting of hydrogen, hydroxy, lower alkyl, lower alkoxy, and $NR^3R^4$ where $R^3$ and $R^4$ are independently selected from the group consisting of hydrogen and lower alkyl, (g) $S(O)_nR^6$ where n is an integer from 1 to 2 and $R^6$ is lower alkyl and with the proviso that $R^5$ does not define a side chain of a naturally occurring amino acid.

Other preferred synthetic amino acids include amino acids wherein the amino group is separated from the carboxyl group by more than one carbon atom such as β-alanine, γ-aminobutyric acid, and the like.

Particularly preferred synthetic amino acids include, by way of example, the D-amino acids of naturally occurring L-amino acids, L-(1-naphthyl)-alanine, L-(2-naphthyl)-alanine, L-cyclohexylalanine, L-2-aminoisobutyric acid, the sulfoxide and sulfone derivatives of methionine (i.e., HOOC $(H_2NCH)CH_2CH_2$ $S(O)_nR^6$) where n and $R^6$ are as defined above as well as the lower alkoxy derivative of methionine (i.e., HOOC $(H_2NCH)CH_2CH_2$ $OR^6$ where $R^6$ is as defined above).

As used herein, a "derivative" of a compound X (for example, a peptide or amino acid) refers to a form of X in which one or more reactive groups in the compound have been derivatized with a substituent group. Examples of peptide derivatives include peptides in which an amino acid side chain, the peptide backbone, or the amino- or carboxy-terminus has been derivatized (for example, peptidic compounds with methylated amide linkages).

As used herein an "analogue" of a compound X refers to a compound which retains chemical structures of X necessary for functional activity of X yet which also contains certain chemical structures which differ from X. An example of an analogue of a naturally occurring peptide is a peptide which includes one or more non-naturally-occurring amino acids. As used herein, a "mimetic" of a compound X refers to a compound in which chemical structures of X necessary for functional activity of X have been replaced with other chemical structures which mimic the conformation of X. Examples of peptidomimetics include peptidic compounds in which the peptide backbone is substituted with one or more benzodiazepine molecules (see for example, James, G. L. et al. 1993 *Science* 260:1937-1942), peptides in which all L-amino acids are substituted with the corresponding D-amino acids and "retro-inverso" peptides (see U.S. Pat. No. 4,522,752 by Sisto), described further below.

The term mimetic, and in particular, peptidomimetic, is intended to include isosteres. The term "isostere" as used herein is intended to include a chemical structure that can be substituted for a second chemical structure because the steric conformation of the first structure fits a binding site specific for the second structure. The term specifically includes peptide backbone modifications (i.e., amide bond mimetics) well known to those skilled in the art. Such modifications include modifications of the amide nitrogen, the α-carbon, amide carbonyl, complete replacement of the amide bond, extensions, deletions or backbone crosslinks. Several peptide backbone modifications are known, including ψ[$CH_2S$], ψ[$CH_2NH$], ψ[$CSNH_2$], ψ[NHCO], ψ[$COCH_2$], and ψ[(E) or (Z) CH=CH]. In the nomenclature used above, ψ indicates the absence of an amide bond. The structure that replaces the amide group is specified within the brackets. Other examples of isosteres include peptides substituted with one or more benzodiazepine molecules (see for example, James, G. L. et al. 1993 *Science* 260:1937-1942).

Other possible modifications include an N-alkyl (or aryl) substitution (ψ[CONR]), backbone crosslinking to construct lactams and other cyclic structures, substitution of all D-amino acids for all L-amino acids within the compound ("inverso" compounds) or retro-inverso amino acid incorporation (ψ[NHCO]). By "inverso" is meant replacing L-amino acids of a sequence with D-amino acids, and by "retro-inverso" or "enantio-retro" is meant reversing the sequence of the amino acids ("retro") and replacing the L-amino acids with D-amino acids. For example, if the parent peptide is Thr-Ala-Tyr, the retro modified form is Tyr-Ala-Thr, the inverso form is thr-ala-tyr (lower case letters refer to D-amino acids), and the retro-inverso form is tyr-ala-thr. Compared to the parent peptide, a retro-inverso peptide has a reversed backbone while retaining substantially the original spatial conformation of the side chains, resulting in a retro-inverso isomer with a topology that closely resembles the parent peptide. See Goodman et al. 1981 *Perspectives in Peptide Chemistry* pp. 283-294. See also U.S. Pat. No. 4,522,752 by Sisto for further description of "retro-inverso" peptides. Other derivatives include C-terminal hydroxymethyl derivatives, O-modified derivatives (for example, C-terminal hydroxymethyl benzyl ether) and N-terminally modified derivatives including substituted amides such as alkylamides and hydrazides.

As used herein, the term "amino acid structure" (such as a "leucine structure", a "phenylalanine structure" or a "glutamine structure") is intended to include the amino acid, as well as analogues, derivatives and mimetics of the amino acid that maintain the functional activity of the compound. For example, the term "phenylalanine structure" is intended to include phenylalanine as well as pyridylalanine and homophenylalanine. The term "leucine structure" is intended to include leucine, as well as substitution with valine or other natural or non-natural amino acid having an aliphatic side chain, such as norleucine.

The amino- and/or carboxy-terminus of the peptide compounds disclosed herein can be unmodified (i.e., Y1 and/or Y2 can be, independently, hydrogen. Alternatively, the amino- and/or carboxy-terminus of the peptide compound can be modified with a derivative group. Amino-derivative groups which can be present at the N-terminus of a peptide compound (i.e., can be Y1) include acetyl, aryl, aralkyl, acyl, epoxysuccinyl and cholesteryl groups. Carboxy-derivative groups which can be present at the C-terminus of a peptide compound (i.e., can be Y2) include alcohol, aldehyde, epoxysuccinate, acid halide, carbonyl, halomethane, and diazomethane groups.

As used herein, "detectable label" or "imaging agent" refers to materials, which when covalently attached to a compound, permit detection of the compound, including but not limited to, detection in vivo in a patient to whom an Eph receptor binding agent has been administered. Suitable detectable labels are well known in the art and include, by way of example, radioisotopes, fluorescent labels (for example, fluorescein), and the like. The particular detectable label employed is not critical and is selected relative to the amount of label to be employed as well as the toxicity of the label at the amount of label employed. Selection of the label relative to such factors is well within the skill of the art.

Covalent attachment of the detectable label to the peptide or peptidomimetic is accomplished by conventional methods well known in the art. For example, when the $^{125}$I radioisotope is employed as the detectable label, covalent attachment of $^{125}$I to the peptide or the peptidomimetic can be achieved by incorporating the amino acid tyrosine into the peptide or peptidomimetic and then iodinating the peptide (see, for example, Weaner, et al. 1994 *Synthesis and Applications of Isotopically Labelled Compounds*, pp. 137-140). If tyrosine is not present in the peptide or peptidomimetic, incorporation of tyrosine to the N or C terminus of the peptide or peptidomimetic can be achieved by well known chemistry. Likewise, $^{32}$P can be incorporated onto the peptide or peptidomimetic as a phosphate moiety through, for example, a hydroxyl group on the peptide or peptidomimetic using conventional chemistry.

By "selectively" is meant having a binding affinity for one or a few Eph receptor family members that is substantially greater than said binding affinity for the other known Eph receptor family members. As used in connection with selective binding affinity, "substantially greater" means at least a two-fold, at least a three-fold, at least a four-fold, at least a five-fold, at least a six-fold, at least a seven-fold, at least a eight-fold, at least a nine-fold, at least a ten-fold, at least a fifteen-fold, at least a twenty-fold, at least a thirty-fold, at least a forty-fold, at least a fifty-fold or at least a hundred-fold increase in the amount of ligand bound to a receptor.

As used herein, "Eph receptor binding agent" or "Eph receptor binding ligand" is a compound that binds to an Eph receptor. The compound may comprise any molecule that is capable of binding one or more Eph receptors. In some cases, the molecule that is capable of binding one or more Eph receptors is a peptide or a peptidomimetic. Such peptides or peptidomimetics can have a length of less than 10, less than 11, less than 12, less than 13, less than 14, less than 15, less than 20, less than 25, less than 30, less than 35, less than 40, less than 45, less than 50, less than 75, less than 100, less than 200, less than 300, less than 400 or less than 500 residues. The terms "Eph receptor binding agent" and "Eph receptor binding ligand may be used interchangeably.

As used herein, "ephrin-A" includes any of the ephrins that are members of the ephrin-A ligand subclass.

As used herein, "ephrin-B" includes any of the ephrins that are members of the ephrin-B ligand subclass As used herein the term "therapeutic agent" means an anticancer agent, neuroprotective agent, or other agent capable of having a desired therapeutic effect for a specific disease indication.

Anticancer agents described herein can be cytotoxic agents or cancer chemotherapeutic agents. As non limiting examples, cytotoxic agents that target a DNA associated process encompass cyclophosphamide, melphalan, mitomycin C, bizelesin, cisplatin, doxorubicin, etoposide, mitoxantrone, SN 38, Et 743, actinomycin D, bleomycin and TLK286. Cancer chemotherapeutic agents can be, without limitation, a taxane such as docetaxel; an anthracyclin such as doxorubicin; an alkylating agent; a vinca alkaloid; an anti metabolite; a platinum agent such as cisplatin or carboplatin; a steroid such as methotrexate; an antibiotic such as adriamycin; a isofamide; or a selective estrogen receptor modulator; an antibody such as trastuzumab.

Taxanes are chemotherapeutic agents useful in the combination treatment of the invention. Useful taxanes include, without limitation, docetaxel (Taxotere; Aventis Pharmaceuticals, Inc.; Parsippany, N.J.) and paclitaxel (Taxol; Bristol Myers Squibb; Princeton, N.J.). See, for example, Chan et al. 1999 *J Clin Oncol* 17:2341 2354, and Paridaens et al. 2000 *J Clin Oncol* 18:724.

Another cancer chemotherapeutic agent useful in the combination treatment of the invention is an anthracyclin such as doxorubicin, idarubicin or daunorubicin. Doxorubicin is a commonly used cancer chemotherapeutic agent and can be useful, for example, for treating breast cancer (Stewart and Ratain, In: "Cancer: Principles and Practice of Oncology" 5th ed., chap. 19, eds. DeVita, Jr. et al.; J. P. Lippincott 1997; Harris et al., In: "Cancer: Principles and practice of oncology," supra, 1997). In addition, doxorubicin has anti angiogenic activity (Folkman, 1997 *Nature Biotechnology* 15:510; Steiner, In: "Angiogenesis: Key principles Science, technology and medicine," pp. 449 454, eds. Steiner et al. Birkhauser Verlag, 1992), which can contribute to its effectiveness in treating cancer.

Alkylating agents such as melphalan or chlorambucil are cancer chemotherapeutic agents useful in the combination treatment of the invention. Similarly, a vinca alkaloid such as vindesine, vinblastine or vinorelbine; or an antimetabolite such as 5 fluorouracil, 5 fluorouridine or a derivative thereof are cancer chemotherapeutic agents useful in the combination treatment of the invention.

Platinum agents are chemotherapeutic agents useful in the combination treatment of the invention. Such a platinum agent can be, for example, cisplatin or carboplatin as described, for example, in Crown, 2001 *Seminars in Oncol* 28:28-37. Other cancer chemotherapeutic agents useful in the combination treatment of the invention include, without limitation, methotrexate, mitomycin C, adriamycin, ifosfamide and ansamycins.

Cancer chemotherapeutic agents used for treatment of breast cancer and other hormonally dependent cancers also can be used as an agent that antagonizes the effect of estrogen, such as a selective estrogen receptor modulator or an anti estrogen. The selective estrogen receptor modulator, tamoxifen, is a cancer chemotherapeutic agent that can be used in the combination treatment of the invention for treatment of breast cancer (Fisher et al. 1998 *J Natl Cancer Instit* 90:1371 1388).

A therapeutic agent useful in the combination treatment of the invention can be an antibody such as a humanized monoclonal antibody. As an example, the anti epidermal growth factor receptor 2 (HER2) antibody, trastuzumab (Herceptin; Genentech, South San Francisco, Calif.) is a therapeutic agent useful in a conjugate of the invention for treating HER2/neu overexpressing breast cancers (White et al. 2001 *Ann Rev Med* 52:125-141).

Another therapeutic agent useful in the invention also can be a cytotoxic agent, which, as used herein, is any molecule that directly or indirectly promotes cell death. Cytotoxic agents useful in the invention include, without limitation, small molecules, polypeptides, peptides, peptidomimetics, nucleic acid molecules, cells and viruses. As non limiting examples, cytotoxic agents useful in the invention include cytotoxic small molecules such as doxorubicin, docetaxel or trastuzumab; antimicrobial peptides such as those described further below; pro-apoptotic polypeptides such as caspases and toxins, for example, caspase 8; diphtheria toxin A chain, Pseudomonas exotoxin A, cholera toxin, ligand fusion toxins such as DAB389EGF, ricinus communis toxin (ricin); and cytotoxic cells such as cytotoxic T cells. See, for example, Martin et al. 2000 *Cancer Res* 60:3218-3224; Kreitman and Pastan 1997 *Blood* 90:252-259; Allam et al. 1997 *Cancer Res* 57:2615-2618; Osborne and Coronado Heinsohn 1996 *Cancer J Sci Am* 2:175. One skilled in the art understands that these and additional cytotoxic agents described herein or known in the art can be useful as therapeutic agents of the invention.

Neuroprotective agents are well known in the art and can be compounds which prevent or delay the death of neuronal cells. As nonlimiting examples, neuroprotective agents can be anti-apoptotic compounds such as small molecule drugs, peptides, proteins, antibodies or a combination thereof. Neuroprotective agents may act through interference with one or more apoptotic or necrotic pathways, activation of neural growth hormone receptors or modulation of ion channels. One skilled in the art understands that these and additional neuroprotective agents described herein or known in the art can be useful as therapeutic agents of the invention.

Eph Receptor Binding Agents

Embodiments of the invention provide agents that bind to the Eph receptors. Many of the compounds described herein selectively bind to only one or a limited number of the sixteen known receptors of the Eph receptor family. The Eph receptor binding agents can be small molecule drugs, peptides, or peptidomimetics. The Eph receptor binding agents may be natural compounds or synthetic compounds. Many of the compounds described herein also bind Eph receptors with high affinity and can act as either an Eph receptor agonist or antagonist. The compounds described herein include "lead" compounds and "derivative" compounds constructed so as to have the same or similar molecular structure or shape as the lead compounds but that differ from the lead compounds either with respect to susceptibility to hydrolysis or proteolysis and/or with respect to other biological properties, such as increased affinity for the receptor, or having additional biological properties unrelated to the target Eph receptor.

Preparation of Peptides and Peptidomimetics

1. Solid Phase Synthesis

The peptides described herein can be prepared by classical methods known in the art, for example, by using standard solid phase techniques. The standard methods include exclusive solid phase synthesis, partial solid phase synthesis methods, fragment condensation, classical solution synthesis, and even by recombinant DNA technology. See, for example, Merrifield, 1963 *J Am Chem Soc* 85:2149, incorporated herein by reference. On solid phase, the synthesis is typically commenced from the C-terminal end of the peptide using an alpha-amino protected resin. A suitable starting material can be prepared, for instance, by attaching the required alpha-amino acid to a chloromethylated resin, a hydroxymethyl resin, or a benzhydrylamine resin. One such chloromethylated resin is sold under the trade name BIO-BEADS SX-1 by BioRad Laboratories, Richmond, Calif., and the preparation of the hydroxymethyl resin is described by Bodonszky, et al. 1966 *Chem Ind* (*London*) 38:1597. The benzhydrylamine (BHA) resin has been described by Pietta and Marshall, 1970 *Chem Commn* 650, and is commercially available from Beckman Instruments, Inc., Palo Alto, Calif., in the hydrochloride form.

Thus, compounds can be prepared by coupling an alpha-amino protected amino acid to the chloromethylated resin with the aid of, for example, cesium bicarbonate catalyst, according to the method described by Gisin, 1973 *Helv Chim Acta* 56:1467. After the initial coupling, the alpha-amino protecting group is removed by a choice of reagents including trifluoroacetic acid (TFA) or hydrochloric acid (HCl) solutions in organic solvents at room temperature.

The alpha-amino protecting groups are those known to be useful in the art of stepwise synthesis of peptides. Included are acyl type protecting groups (for example, formyl, trifluoroacetyl, acetyl), aromatic urethane type protecting groups (for example benzyloxycarboyl (Cbz) and substituted Cbz), aliphatic urethane protecting groups (for example, t-butyloxycarbonyl (Boc), isopropyloxycarbonyl, cyclohexyloxycarbonyl) and alkyl type protecting groups (for example, benzyl, triphenylmethyl). Boc and Fmoc are preferred protecting groups. The side chain protecting group remains intact during coupling and is not split off during the deprotection of the amino-terminus protecting group or during coupling. The side chain protecting group must be removable upon the completion of the synthesis of the final peptide and under reaction conditions that will not alter the target peptide.

The side chain protecting groups for Tyr include tetrahydropyranyl, tert-butyl, trityl, benzyl, Cbz, Z—Br—Cbz, and 2,5-dichlorobenzyl. The side chain protecting groups for Asp include benzyl, 2,6-dichlorobenzyl, methyl, ethyl, and cyclohexyl. The side chain protecting groups for Thr and Ser include acetyl, benzoyl, trityl, tetrahydropyranyl, benzyl, 2,6-dichlorobenzyl, and Cbz. The side chain protecting group for Thr and Ser is benzyl. The side chain protecting groups for Arg include nitro, Tosyl (Tos), Cbz, adamantyloxycarbonyl mesitoylsulfonyl (Mts), or Boc. The side chain protecting groups for Lys include Cbz, 2-chlorobenzyloxycarbonyl (2Cl-Cbz), 2-bromobenzyloxycarbonyl (2-BrCbz), Tos, or Boc.

After removal of the alpha-amino protecting group, the remaining protected amino acids are coupled stepwise in the desired order. An excess of each protected amino acid is generally used with an appropriate carboxyl group activator such as dicyclohexylcarbodiimide (DCC) in solution, for example, in methylene chloride ($CH_2Cl_2$), dimethyl formamide (DMF) mixtures.

After the desired amino acid sequence has been completed, the desired peptide is decoupled from the resin support by treatment with a reagent such as trifluoroacetic acid or hydrogen fluoride (HF), which not only cleaves the peptide from the resin, but also cleaves all remaining side chain protecting groups. When the chloromethylated resin is used, hydrogen fluoride treatment results in the formation of the free peptide acids. When the benzhydrylamine resin is used, hydrogen fluoride treatment results directly in the free peptide amide. Alternatively, when the chloromethylated resin is employed, the side chain protected peptide can be decoupled by treatment of the peptide resin with ammonia to give the desired side chain protected amide or with an alkylamine to give a side chain protected alkylamide or dialkylamide. Side chain protection is then removed in the usual fashion by treatment with hydrogen fluoride to give the free amides, alkylamides, or dialkylamides.

These solid phase peptide synthesis procedures are well known in the art and further described by J. M. Stewart and J. D. Young, 1984 *Solid Phase Peptide Syntheses* 2nd Ed., Pierce Chemical Company.

Using the "encoded synthetic library" or "very large scale immobilized polymer synthesis" system described in U.S. patent application Ser. No. 07/492,462, filed Mar. 7, 1990; Ser. No. 07/624,120, filed Dec. 6, 1990; and Ser. No. 07/805,727, filed Dec. 6, 1991; one can not only determine the minimum size of a peptide with such activity, one can also make all of the peptides that form the group of peptides that differ from the preferred motif (or the minimum size of that motif) in one, two, or more residues. This collection of peptides can then be screened for ability to bind to members of the Eph receptor family including, but not limited to, EphA2, EphA4, EphA5, EphA7, EphB2 and EphB4. It will be appreciated that this immobilized polymer synthesis system or other peptide synthesis methods can also be used to synthesize truncation analogs and deletion analogs and combinations of truncation and deletion analogs of all of the peptide compounds of the invention.

2. Synthetic Amino Acids

These procedures can also be used to synthesize peptides in which amino acids other than the 20 naturally occurring, genetically encoded amino acids are substituted at one, two, or more positions of any of the compounds of the invention. For instance, naphthylalanine can be substituted for tryptophan, facilitating synthesis. Other synthetic amino acids that can be substituted into the peptides of the present invention include L-hydroxypropyl, L-3,4-dihydroxy-phenylalanyl, d amino acids such as L-d-hydroxylysyl and D-d-methylalanyl, L-α-methylalanyl, β amino acids, and isoquinolyl. D amino acids and non-naturally occurring synthetic amino acids can also be incorporated into the peptides of the present invention (see, for example, Roberts, et al. 1983 *Unusual Amino/Acids in Peptide Synthesis* 5:341-449).

One can replace the naturally occurring side chains of the 20 genetically encoded amino acids (or D amino acids) with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclic. In particular, proline analogs in which the ring size of the proline residue is changed from 5 members to 4, 6, or 7 members can be employed. Cyclic groups can be saturated or unsaturated, and if unsaturated, can be aromatic or non-aromatic. Heterocyclic groups preferably contain one or more nitrogen, oxygen, and/or sulphur heteroatoms. Examples of such groups include the farazanyl, furyl, imidazolidinyl, imidazolyl, imidazolinyl, isothiazolyl, isoxazolyl, morpholinyl (for example, morpholino), oxazolyl, piperazinyl (for example, 1-piperazinyl), piperidyl (for example, 1-piperidyl, piperidino), pyranyl, pyrazinyl, pyrazolidinyl, pyrazolinyl, pyrazolyl, pyridazinyl, pyridyl, pyrimidinyl, pyrrolidinyl (for example, 1-pyrrolidinyl), pyrrolinyl, pyrrolyl, thiadiazolyl, thiazolyl, thienyl, thiomorpholinyl (for example, thiomorpholino), and triazolyl. These heterocyclic groups can be substituted or unsubstituted. Where a group is substituted, the substituent can be alkyl, alkoxy, halogen, oxygen, or substituted or unsubstituted phenyl.

One can also readily modify the peptides of the instant invention by phosphorylation (see, for example, W. Bannwarth, et al. 1996 *Biorganic and Medicinal Chemistry Letters* 6:2141-2146), and other methods for making peptide derivatives of the compounds of the present invention are described in Hruby, et al. 1990 *Biochem J* 268:249-262. Thus, the peptide compounds of the invention also serve as a basis to prepare peptidomimetics with similar biological activity.

3. Terminal Modifications

Those of skill in the art recognize that a variety of techniques are available for constructing peptidomimetics with the same or similar desired biological activity as the corresponding peptide compound but with more favorable activity than the peptide with respect to solubility, stability, and susceptibility to hydrolysis and proteolysis. See, for example, Morgan, et al. 1989 *Ann Rep Med Chem* 24:243-252. The following describes methods for preparing peptidomimetics modified at the N-terminal amino group, the C-terminal carboxyl group, and/or changing one or more of the amido linkages in the peptide to a non-amido linkage. It being understood that two or more such modifications can be coupled in one peptidomimetic structure (for example, modification at the C-terminal carboxyl group and inclusion of a CH2-carbamate linkage between two amino acids in the peptide).

1). N-terminal Modifications

The peptides typically are synthesized as the free acid but, as noted above, could be readily prepared as the amide or ester. One can also modify the amino and/or carboxy terminus of the peptide compounds to produce other useful compounds. Amino terminus modifications include methylation (i.e., —$NHCH_3$ or $NH(CH_3)_2$), acetylation, adding a benzyloxycarbonyl group, or blocking the amino terminus with any blocking group containing a carboxylate functionality defined by RCOO, where R is selected from the group consisting of naphthyl, acridinyl, steroidyl, and similar groups. Carboxy terminus modifications include replacing the free acid with a carboxamide group or forming a cyclic lactam at the carboxy terminus to introduce structural constraints.

Amino terminus modifications are as recited above and include alkylating, acetylating, adding a carbobenzoyl group, forming a succinimide group, etc. (See, for example, Murray, et al. 1995 *Burger's Medicinal Chemistry and Drug Discovery* 5th ed., Vol. 1, Manfred E. Wolf, ed., John Wiley and Sons, Inc.) Specifically, the N-terminal amino group can then be reacted as follows:

(a) to form an amide group of the formula RC(O)NH where R is as defined above by reaction with an acid halide [for example, RC(O)Cl] or symmetric anhydride. Typically, the reaction can be conducted by contacting about equimolar or excess amounts (for example, about 5 equivalents) of an acid halide to the peptide in an inert diluent (for example, dichloromethane) preferably containing an excess (for example, about 10 equivalents) of a tertiary amine, such as diisopropylethylamine, to scavenge the acid generated during reaction. Reaction conditions are otherwise conventional (for example, room temperature for 30 minutes). Alkylation of the terminal amino to provide for a lower alkyl N-substitution followed by reaction with an acid halide as described above will provide for N-alkyl amide group of the formula RC(O)NR;

(b) to form a succinimide group by reaction with succinic anhydride. As before, an approximately equimolar amount or an excess of succinic anhydride (for example, about 5 equivalents) can be employed and the amino group is converted to the succinimide by methods well known in the art including the use of an excess (for example, ten equivalents) of a tertiary amine such as diisopropylethylamine in a suitable inert solvent (for example, dichloromethane). See, for example, Wollenberg, et al., U.S. Pat. No. 4,612,132 which is incorporated herein by reference in its entirety. It is understood that the succinic group can be substituted with, for example, $C_2$ $C_6$ alkyl or SR substituents which are prepared in a conventional manner to provide for substituted succinimide at the N-terminus of the peptide. Such alkyl substituents are prepared by reaction of a lower olefin ($C_2$ $C_6$) with maleic anhydride in the manner described by Wollenberg, et al., supra and SR substituents are prepared by reaction of RSH with maleic anhydride where R is as defined above;

(c) to form a benzyloxycarbonyl-NH or a substituted benzyloxycarbonyl-NH group by reaction with approximately an equivalent amount or an excess of CBZ Cl (i.e., benzyloxycarbonyl chloride) or a substituted CBZ Cl in a suitable inert diluent (for example, dichloromethane) preferably containing a tertiary amine to scavenge the acid generated during the reaction;

(d) to form a sulfonamide group by reaction with an equivalent amount or an excess (for example, 5 equivalents) of R $S(O)_2Cl$ in a suitable inert diluent (dichloromethane) to convert the terminal amine into a sulfonamide where R is as defined above. Preferably, the inert diluent contains excess tertiary amine (for example, ten equivalents) such as diisopropylethylamine, to scavenge the acid generated during reaction. Reaction conditions are otherwise conventional (for example, room temperature for 30 minutes);

(e) to form a carbamate group by reaction with an equivalent amount or an excess (for example, 5 equivalents) of R OC(O)Cl or R OC(O)OC$_6$H$_4$ p NO$_2$ in a suitable inert diluent (for example, dichloromethane) to convert the terminal amine into a carbamate where R is as defined above. Preferably, the inert diluent contains an excess (for example, about 10 equivalents) of a tertiary amine, such as diisopropylethylamine, to scavenge any acid generated during reaction. Reaction conditions are otherwise conventional (for example, room temperature for 30 minutes); and (f) to form a urea group by reaction with an equivalent amount or an excess (for example, 5 equivalents) of R N=C=O in a suitable inert diluent (for example, dichloromethane) to convert the terminal amine into a urea (i.e., RNHC(O)NH) group where R is as defined above. Preferably, the inert diluent contains an excess (for example, about 10 equivalents) of a tertiary amine, such as diisopropylethylamine. Reaction conditions are otherwise conventional (for example, room temperature for about 30 minutes).

2). C-Terminal Modifications

In preparing peptidomimetics wherein the C-terminal carboxyl group is replaced by an ester (i.e., C(O)OR where R is as defined above), the resins used to prepare the peptide acids are employed, and the side chain protected peptide is cleaved with base and the appropriate alcohol, for example, methanol. Side chain protecting groups are then removed in the usual fashion by treatment with hydrogen fluoride to obtain the desired ester.

In preparing peptidomimetics wherein the C-terminal carboxyl group is replaced by the amide $C(O)NR^3R^4$, a benzhydrylamine resin is used as the solid support for peptide synthesis. Upon completion of the synthesis, hydrogen fluoride treatment to release the peptide from the support results directly in the free peptide amide (i.e., the C-terminus is $C(O)NH_2$). Alternatively, use of the chloromethylated resin during peptide synthesis coupled with reaction with ammonia to cleave the side chain protected peptide from the support yields the free peptide amide and reaction with an alkylamine or a dialkylamine yields a side chain protected alkylamide or dialkylamide (i.e., the C-terminus is $C(O)NRR^1$ where R and $R^1$ are as defined above). Side chain protection is then removed in the usual fashion by treatment with hydrogen fluoride to give the free amides, alkylamides, or dialkylamides.

In another alternative embodiment, the C-terminal carboxyl group or a C-terminal ester can be induced to cyclize by internal displacement of the OH or the ester (OR) of the carboxyl group or ester respectively with the N-terminal amino group to form a cyclic peptide. For example, after synthesis and cleavage to give the peptide acid, the free acid is converted to an activated ester by an appropriate carboxyl group activator such as dicyclohexylcarbodiimide (DCC) in solution, for example, in methylene chloride ($CH_2Cl_2$), dimethyl formamide (DMF) mixtures. The cyclic peptide is then formed by internal displacement of the activated ester with the N-terminal amine. Internal cyclization as opposed to polymerization can be enhanced by use of very dilute solutions. Such methods are well known in the art.

One can also cyclize the peptides of the invention, or incorporate a desamino or descarboxy residue at the termini of the peptide, so that there is no terminal amino or carboxyl group, to decrease susceptibility to proteases or to restrict the conformation of the peptide. C-terminal functional groups of the compounds of the present invention include amide, amide lower alkyl, amide di(lower alkyl), lower alkoxy, hydroxy, and carboxy, and the lower ester derivatives thereof, and the pharmaceutically acceptable salts thereof.

In addition to the foregoing N-terminal and C-terminal modifications, the peptide compounds described herein, including peptidomimetics, can advantageously be modified with or covalently coupled to one or more of a variety of hydrophilic polymers. It has been found that when the peptide compounds are derivatized with a hydrophilic polymer, their solubility and circulation half-lives are increased and their immunogenicity is masked. Quite surprisingly, the foregoing can be accomplished with little, if any, diminishment in their binding activity. Nonproteinaceous polymers suitable for use include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives, etc. Generally, such hydrophilic polymers have an average molecular weight ranging from about 500 to about 100,000 daltons, more preferably from about 2,000 to about 40,000 daltons and, even more preferably, from about 5,000 to about 20,000 daltons. In preferred embodiments, such hydrophilic polymers have average molecular weights of about 5,000 daltons, 10,000 daltons and 20,000 daltons.

The peptide compounds can be derivatized with or coupled to such polymers using any of the methods set forth in Zallipsky, S. 1995 *Bioconjugate Chem* 6:150-165; Monfardini, C, et al. 1995 *Bioconjugate Chem* 6:62-69; U.S. Pat. Nos. 4,640,835; 4,496,689; 4,301,144; 4,670,417; 4,791,192; 4,179,337 or WO 95/34326, all of which are incorporated by reference in their entirety herein.

In one embodiment, the peptide compounds are derivatized with polyethylene glycol (PEG). PEG is a linear, water-soluble polymer of ethylene oxide repeating units with two terminal hydroxyl groups. PEGs are classified by their molecular weights which typically range from about 500 daltons to about 40,000 daltons. In a presently preferred embodiment, the PEGs employed have molecular weights ranging from 5,000 daltons to about 20,000 daltons. PEGs coupled to the peptide compounds of the present invention can be either branched or unbranched. (See, for example, Monfardini, C. et al. 1995 *Bioconjugate Chem* 6:62-69). PEGs are commercially available from Shearwater Polymers, Inc. (Huntsville, Ala.), Sigma Chemical Co. and other companies. Such PEGs include, but are not limited to, monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH2), monomethoxypolyethylene glycol-tresylate (MePEG-TRES), and monomethoxypolyethylene glycol-imidazolyl-carbonyl (MePEG-IM).

Briefly, in one exemplar embodiment, the hydrophilic polymer which is employed, for example, PEG, is preferably capped at one end by an unreactive group such as a methoxy or ethoxy group. Thereafter, the polymer is activated at the other end by reaction with a suitable activating agent, such as cyanuric halides (for example, cyanuric chloride, bromide or fluoride), diimadozle, an anhydride reagent (for example, a dihalosuccinic anhydride, such as dibromosuccinic anhydride), acyl azide, p-diazoiumbenzyl ether, 3-(p-diazoniumphenoxy)-2-hydroxypropylether) and the like. The activated polymer is then reacted with a peptide compound as described herein to produce a peptide compound derivatized with a polymer. Alternatively, a functional group in the peptide compounds of the invention can be activated for reaction with the polymer, or the two groups can be joined in a concerted coupling reaction using known coupling methods. It will be readily appreciated that the peptide compounds of the invention can be derivatized with PEG using a myriad of other reaction schemes known to and used by those of skill in the art.

In some embodiments, the derivatized peptides have an activity that is about 0.1 to about 0.01-fold that of the unmodified peptides. In more other embodiments, the derivatized peptides have an activity that is about 0.1 to about 1-fold that of the unmodified peptides. In still other embodiments, the derivatized peptides have an activity that is greater than the unmodified peptides.

Peptides suitable for use in this embodiment generally include the peptides, i.e., ligands, that bind to members of the Eph receptor family including, but not limited to, EphA2, EphA4, EphA5, EphA7, EphB2 or EphB4. Such peptides typically comprise about 50 amino acid residues or less and, more preferably, about 20 amino acid residues or less. Hydrophilic polymers suitable for use in the present invention include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives, etc. Generally, such hydrophilic polymers have an average molecular weight ranging from about 500 to about 100,000 daltons, more preferably from about 2,000 to about 40,000 daltons and, even more preferably, from about 5,000 to about 20,000 daltons. In some embodiments, such hydrophilic polymers have average molecular weights of about 5,000 daltons, 10,000 daltons and 20,000 daltons. The peptide compounds can be derivatized with using the methods described above and in the cited references.

4. Backbone Modifications

Other methods for making peptide derivatives of the compounds are described in Hruby, et al. 1990 *Biochem J* 268(2): 249-262, incorporated herein by reference. Thus, the peptide compounds also serve as structural models for non-peptidic compounds with similar biological activity. Those of skill in the art recognize that a variety of techniques are available for constructing compounds with the same or similar desired biological activity as the lead peptide compound but with more favorable activity than the lead with respect to solubility, stability, and susceptibility to hydrolysis and proteolysis. See Morgan, et al. 1989 *Ann Rep Med Chem* 24:243-252, incorporated herein by reference. These techniques include replacing the peptide backbone with a backbone composed of phosphonates, amidates, carbamates, sulfonamides, secondary amines, and N-methylamino acids.

Peptidomimetics wherein one or more of the peptidyl linkages [C(O)NH] have been replaced by such linkages as a $CH_2$-carbamate linkage, a phosphonate linkage, a $CH_2$-sulfonamide linkage, a urea linkage, a secondary amine ($CH_2NH$) linkage, and an alkylated peptidyl linkage [C(O) $NR^6$ where $R^6$ is lower alkyl] are prepared during conventional peptide synthesis by merely substituting a suitably protected amino acid analogue for the amino acid reagent at the appropriate point during synthesis.

Suitable reagents include, for example, amino acid analogues wherein the carboxyl group of the amino acid has been replaced with a moiety suitable for forming one of the above linkages. For example, if one desires to replace a C(O)NR linkage in the peptide with a $CH_2$-carbamate linkage ($CH_2OC$ (O)NR), then the carboxyl (COOH) group of a suitably protected amino acid is first reduced to the $CH_2OH$ group which is then converted by conventional methods to a OC(O)Cl functionality or a para-nitrocarbonate $OC(O)O\ C_6H_4\ p\ NO_2$ functionality. Reaction of either of such functional groups with the free amine or an alkylated amine on the N-terminus of the partially fabricated peptide found on the solid support leads to the formation of a $CH_2OC(O)NR$ linkage. For a more detailed description of the formation of such $CH_2$-carbamate linkages, see Cho, et al. 1993 *Science* 261:1303-1305.

Similarly, replacement of an amido linkage in the peptide with a phosphonate linkage can be achieved in the manner set forth in U.S. patent application Ser. Nos. 07/943,805, 08/081,577, and 08/119,700, the disclosures of which are incorporated herein by reference in their entirety.

Replacement of an amido linkage in the peptide with a $CH_2$-sulfonamide linkage can be achieved by reducing the carboxyl (COOH) group of a suitably protected amino acid to the $CH_2OH$ group and the hydroxyl group is then converted to a suitable leaving group such as a tosyl group by conventional methods. Reaction of the tosylated derivative with, for example, thioacetic acid followed by hydrolysis and oxidative chlorination will provide for the $CH_2S(O)_2Cl$ functional group which replaces the carboxyl group of the otherwise suitably protected amino acid. Use of this suitably protected amino acid analogue in peptide synthesis provides for inclusion of a $CH_2S(O)_2NR$ linkage, which replaces the amido linkage in the peptide thereby providing a peptidomimetic. For a more complete description on the conversion of the carboxyl group of the amino acid to a $CH_2S(O)_2Cl$ group, see, for example, Weinstein, B., 1983 *Chemistry & Biochemistry of Amino Acids, Peptides and Proteins* Vol. 7, pp. 267-357, Marcel Dekker, Inc., New York, which is incorporated herein by reference.

Replacement of an amido linkage in the peptide with a urea linkage can be achieved in the manner set forth in U.S. patent application Ser. No. 08/147,805 which application is incorporated herein by reference in its entirety.

Secondary amine linkages wherein a $CH_2NH$ linkage replaces the amido linkage in the peptide can be prepared by employing, for example, a suitably protected dipeptide analogue wherein the carbonyl bond of the amido linkage has been reduced to a $CH_2$ group by conventional methods. For example, in the case of diglycine, reduction of the amide to the amine will yield after deprotection $H_2NCH_2CH_2NHCH_2COOH$ which is then used in N-protected form in the next coupling reaction. The preparation of such analogues by reduction of the carbonyl group of the amido linkage in the dipeptide is well known in the art (see, for example, M. W. Remington 1994 *Meth Mol Bio* 35:241-247).

The suitably protected amino acid analogue is employed in the conventional peptide synthesis in the same manner as would the corresponding amino acid. For example, typically about 3 equivalents of the protected amino acid analogue are employed in this reaction. An inert organic diluent such as methylene chloride or DMF is employed and, when an acid is generated as a reaction by-product, the reaction solvent will typically contain an excess amount of a tertiary amine to scavenge the acid generated during the reaction. One particularly preferred tertiary amine is diisopropylethylamine which is typically employed in about 10-fold excess. The reaction results in incorporation into the peptidomimetic of an amino acid analogue having a non-peptidyl linkage. Such substitution can be repeated as desired such that from zero to all of the amido bonds in the peptide have been replaced by non-amido bonds.

One can also cyclize the peptides, or incorporate a desamino or descarboxy residue at the termini of the peptide, so that there is no terminal amino or carboxyl group, to decrease susceptibility to proteases or to restrict the conformation of the peptide. C-terminal functional groups of the compounds include amide, amide lower alkyl, amide di(lower alkyl), lower alkoxy, hydroxy, and carboxy, and the lower ester derivatives thereof, and the pharmaceutically acceptable salts thereof.

5. Disulfide Bond Formation

The compounds may exist in a cyclized form with an intramolecular disulfide bond between the thiol groups of the cysteines. Alternatively, an intermolecular disulfide bond between the thiol groups of the cysteines can be produced to yield a dimeric (or higher oligomeric) compound. One or more of the cysteine residues may also be substituted with a homocysteine.

Other embodiments of this invention include analogs of these disulfide derivatives in which one of the sulfurs has been replaced by a $CH_2$ group or other isostere for sulfur. These analogs can be made via an intramolecular or intermolecular displacement, using methods known in the art.

Alternatively, the amino-terminus of the peptide can be capped with an alpha-substituted acetic acid, wherein the alpha substituent is a leaving group, such as an α-haloacetic acid, for example, α-chloroacetic acid, α-bromoacetic acid, or α-iodoacetic acid. The compounds of the present invention can be cyclized or dimerized via displacement of the leaving group by the sulfur of the cysteine or homocysteine residue. See, for example, Andreu, et al. 1994 *Meth Mol Bio* 35(7): 91-169; Barker, et al. 1992 *J Med Chem* 35:2040-2048; and Or, et al. 1991 *J Org Chem* 56:3146-3149, each of which is incorporated herein by reference.

The peptides may also be prepared by recombinant DNA techniques well known in the art.

Modulation of Eph Receptors with Eph Receptor Binding Compounds

The Eph receptor binding compounds described herein are capable of modulating Eph activity in a cell. The Eph receptor binding compounds that modulate Eph activity comprise a peptide or peptidomimetic described herein which binds to one or more members of the Eph receptor family. In some embodiments of the present invention the Eph receptor binding compounds include only a single peptide or peptidomimetic described herein. In some embodiments of the present invention, cells are contacted with an amount of Eph receptor binding compound in an amount that is effective to cause the phosphorylation of the receptor thereby activating downstream signaling events. In some embodiments, cells are contacted with an amount of Eph receptor binding compound in an amount that is effective to prevent phosphorylation of the receptor by ephrin ligands, thereby inhibiting receptor activity. In other embodiments, the cells can be contacted with an Eph receptor binding compound in an amount that is effective to cause activation or inactivation of downstream signaling events. The amount of Eph receptor binding compound that is effective to activate or inactivate downstream signaling events includes concentrations of at least 0.05 µM, at least 0.1 µM, at least 0.2 µM, at least 0.3 µM, at least 0.4 µM, at least 0.5 µM, at least 0.6 µM, at least 0.7 µM, at least 0.8 µM, at least 0.9 µM, at least 1 µM, at least 5 µM, at least 10 µM, at least 20 µM, at least 30 µM, at least 40 µM, at least 50 µM, at least 60 µM, at least 70 µM, at least 80 µM, at least 90 µM, at least 100 µM or at least 200 µM. Determination of other effective concentrations not described herein can be readily determined by one of ordinary skill in the art.

In some embodiments of the present invention, the Eph receptor of interest is modulated in cells both in vitro and in vivo. With respect to either application, the cells can be any cells that express at least one member of the Eph family of receptors including but not limited to human cells.

In some embodiments of the present invention, receptors of the EphA sub-family are modulated. Such receptors include EphA1, EphA2, EphA3, EphA4, EphA5, EphA6, EphA7, EphA8, EphA9, or EphA10. In certain embodiments, cells expressing the EphA2 receptor are contacted with effective amounts of peptides, peptidomimetics or small molecules described herein so as to modulate the activity of this receptor and subsequent downstream signaling events. In other embodiments, cells expressing the EphA4 receptor are contacted with effective amounts of peptides, peptidomimetics or small molecules described herein so as to modulate the activity of this receptor and subsequent downstream signaling events. In still other embodiments, cells expressing the EphA5 or EphA7receptor are contacted with effective amounts of peptides, peptidomimetics or small molecules described herein so as to modulate the activity of this receptor and subsequent downstream signaling events.

In other embodiments, receptors of the EphB sub-family are modulated. Such receptors include EphB1, EphB2, EphB3, EphB4, EphB5 and EphB6. In certain embodiments, cells expressing the EphB4 receptor are contacted with effective amounts of peptides, peptidomimetics or small molecules described herein so as to modulate the activity of this receptor and subsequent downstream signaling events.

Stimulation of certain members of Eph family receptors have been implicated in the activation of apoptosis (programmed cell death). Accordingly, activation of programmed cell death in certain cells overexpressing an Eph receptor, such as certain types of neoplastic cells, would be advantageous for the selective killing of undesirable cell populations. Furthermore, an Eph receptor binding compound that acts as a selective agonist of a specific overexpressed Eph receptor in a cell type targeted for programmed cell death would provide a method to eliminate target cells without killing nontarget cells.

In some embodiments of the present invention, methods of administering an Eph receptor binding compound that acts as a selective agonist or antagonist of a specific member of the Eph receptor family are contemplated. In some embodiments, selective agonists, such as a peptide, peptidomimetics or small molecules described herein, can be used to activate programmed cell death by administering an effective amount of such peptide, peptidomimetic or small molecule to mammals, including humans. In certain embodiments, the agonist binds to EphA2 thereby competitively inhibiting ephrin-A1 binding to this receptor. In other embodiments, binding of the agonist stimulates the phosphorylation of the receptor.

The effective amount of agonist that is administered to the mammal can range from about 0.001 mg to about 50 mg/kg of body weight per day. The effective amount will depend on factors including, but not limited to, the route by which the agonist is administered, binding affinity of the agonist, Eph receptor expression level in target cells, and Eph receptor expression level in nontarget cells. It will be appreciated, however, that determination of an effective amount of agonist can be readily determined by one of ordinary skill in the art.

Eph Receptor Binding Compounds as Therapeutics and Therapeutic Delivery Agents

The Eph receptor binding compounds described herein can also be administered to warm blooded animals, including humans, to modulate Eph receptors in vivo. For example, certain peptides disclosed herein can be used to selectively activate EphA2 or inhibit EphA4. Thus, the present invention encompasses methods for therapeutic treatment of Eph related disorders that comprise administering such a compound in amounts sufficient to activate or inhibit an Eph receptor in vivo.

Targeting Eph receptors also allows therapeutic intervention in cancer and other diseases. The Eph receptor binding compounds described herein can be used to deliver cytotoxic agents to blood vessels of diseased tissues. Indeed, vascular-targeted peptides coupled to chemotherapeutic drugs, toxins, or pro-apoptotic peptides can decrease tumor growth, suppress clinical arthritis, or destroy prostate tissue (Arap, W. et al. 1998 *Science* 279:377-380; Olson, T. A. et al. 1997 *Int J Cancer* 73:865-870; Ellerby, H. M. et al. 1999 *Nat Med* 5:1032-1038; Arap, W. et al. 2002 *PNAS USA* 99:1527-1531; Gerlag, D. M. et al. 2001 *Arthritis Research* 3:357-361). For example, tyrosine phosphorylation of EphA2 caused by agonists mediates internalization of the receptor and the agonist (Zantek, N. D. et al. 1999 *Cell Growth Differ* 10:629-638; Carles-Kinch, K. et al. 2002 *Cancer Res* 62:2840-2847; Van der Geer, P. et al. 1994 *Annu Rev Cell Biol* 10:251-337), therefore, toxic or pro-apoptotic substances can be delivered intracellularly to selectively kill cells (Ellerby, H. M. et al. 1999 Nat Med 5:1032-1038). Furthermore, activation of EphA2 induced by the Eph receptor binding compounds described herein can reduce proliferation, invasiveness, and metastatic behavior of EphA2-expressing cancer cells (Zantek, N. D. et al. 1999 *Cell Growth Differ* 10:629-638; Carles-Kinch, K. et al. 2002 *Cancer Res* 62:2840-2847; Miao, H. et al. Nature 2000 *Cell Biol* 2:62-69). It is known in the art that EphA2 activation correlates with decreased malignancy of breast and prostate cancer cells and reverses the transforming effects of EphA2 overexpression (Zelinski, D. P. et al. 2002 *J Cell Biochem* 85:714-720; Zantek, N. D. et al. 1999 *Cell Growth Differ* 10:629-638; Carles-Kinch, K. et al. 2002 *Cancer Res* 62:2840-2847). EphA2 activation by the compositions disclosed herein can sensitize cells to apoptotic stimuli when the Eph receptor binding compounds described herein are used to deliver cytotoxic agents (Dohn, M. et al. 2001 *Oncogene* 20:6503-6515).

Some embodiments of the present invention contemplate conjugates that comprise a therapeutic agent linked to an Eph receptor binding compound, such as the peptides, peptidomimetics and small molecules described herein. Such conjugates can be delivered to target cells that express an appropriate Eph receptor by administering an appropriate conjugate to an animal in need of treatment. In some embodiments, the therapeutic agent is responsible for the treatment. In other embodiments, both the therapeutic agent and the Eph receptor binding compound contribute to the treatment. In some embodiments the therapeutic agent is an imaging agent.

The Eph receptor binding compound which binds to the Eph receptor of interest is linked to a therapeutic agent with a linker. The linker can be any bond, small molecule, or other vehicle that allows the Eph receptor binding compound and the therapeutic agent to be targeted to the same area, tissue, or cell. Preferably, the linker is cleavable.

In one embodiment the linker is a chemical bond between one or more Eph receptor binding compounds and one or more therapeutic agents. Thus, the bond may be covalent or ionic. An example of a conjugate where the linker is a chemical bond would be a fusion protein. In one embodiment, the chemical bond is a pH sensitive bond. Alternatively, the bond may not be pH sensitive, but may be cleavable by a specific enzyme or chemical which is subsequently added or naturally found in the microenvironment of the targeted site. Alternatively, the bond may be a bond that is cleaved under reducing conditions, for example a disulfide bond. Alternatively, the bond may not be cleavable.

Any kind of pH cleavable or pH sensitive linker may be used. Examples of acid cleavable bonds include, but are not limited to: a class of organic acids known as cis-polycarboxylic alkenes. This class of molecule contains at least three carboxylic acid groups (COOH) attached to a carbon chain that contains at least one double bond. These molecules as well as how they are made and used is disclosed in Shen, et al. U.S. Pat. No. 4,631,190 (herein incorporated by reference). Alternatively, molecules such as amino-sulfhydryl cross-linking reagents which are cleavable under mildly acidic conditions may be used. These molecules are disclosed in Blattler et al. U.S. Pat. No. 4,569,789 (herein incorporated by reference).

Alternatively, the cleavable linker may be a time-release bond, such as a biodegradable, hydrolyzable bond. Typical biodegradable carrier bonds include esters, amides or urethane bonds, so that typical carriers are polyesters, polyamides, polyurethanes and other condensation polymers having a molecular weight between about 5,000 and 1,000,000. Examples of these carriers/bonds are shown in Peterson, et al. U.S. Pat. No. 4,356,166 (herein incorporated by reference). Other acid cleavable linkers may be found in U.S. Pat. Nos. 4,569,789 and 4,631,190 (herein incorporated by reference) or Blattler et al. 1985 *Biochemistry* 24:1517-1525. The linkers are cleaved by natural acidic conditions, or alternatively, acid conditions can be induced at a target site as explained in Abrams et al. U.S. Pat. No. 4,171,563 (herein incorporated by reference).

Examples of linking reagents which contain cleavable disulfide bonds (reducable bonds) include, but are not limited to "DPDPB", 1,4-di-[3'-(2'-pyridyldithio)propionamido]butane; "SADP", (N-succinimidyl(4-azidophenyl) 1,3'-dithiopropionate); "Sulfo-SADP" (Sulfosuccinimidyl (4-azidophenyldithio)propionate; "DSP"—Dithio bis (succinimidylproprionate); "DTSSP"—3,3'-Dithio bis (sulfosuccinimidylpropionate); "DTBP"—dimethyl 3,3'—dithiobispropionimidate-2HCl, all available from Pierce Chemicals (Rockford, Ill.).

Examples of linking reagents cleavable by oxidation are "DST"-disuccinimidyl tartarate; and "Sulfo-DST"—disuccinimidyl tartarate. Again, these linkers are available from Pierce Chemicals.

Examples of non-cleavable linkers are "Sulfo-LC-SMPT"—(sulfosuccinimidyl 6-[alpha-methyl-alpha-(2-pyridylthio)toluamido]hexanoate; "SMPT"; "ABH"—Azidobenzoyl hydrazide; "NHS-ASA"—N-Hydroxysuccinimidyl-4-azidosalicyclic acid; "SASD"—Sulfosuccinimidyl 2-(p-azidosalicylamido)ethyl-1,3-dithiopropionate; "APDP"—N-[4-(p-azidosalicylamido) buthy]-3'(2'-pyidyldithio) propionamide; "BASED"—Bis-[beta-(4-azidosalicylamido) ethyl]disulfide; "HSAB"—N-hydroxysuccinimidyl-4 azidobenzoate; "APG"—p-Azidophenyl glyoxal monohydrate; "SANPAH"—N-Succiminidyl-6-(4'-azido-2'-mitrophenyl-amimo)hexanoate; "Sulfo-SANPAH"—Sulfosuccinimidyl 6-(4'-azido-2'-nitrophenylamino)hexanoate; "ANB-NOS"—N-5-Azido-2-nitrobenzyoyloxysuccinimide; "SAND"—Sulfosuccinimidyl-2-(m-azido-o-mitrobenzamido)-ethyl-1,3'-dithiopropionate; "PNP-DTP"—p-nitrophenyl-2-diazo-3,3,3-trifluoropropionate; "SMCC"—Succinimidyl 4-(N-maleimidomethyl)cyclohexane-1-carboxylate; "Sulfo-SMCC"—Sulfosuccinimidyl 4-(N-maleimidomethyl) cyclohexane-1-carboxylate; "MBS"—m-Maleimidobenzoyl-N-hydroxysuccinimide ester; "sulfo-MBS"—m-Maleimidobenzoyl-N-hydroxysulfosuccinimide ester; "SIAB"—N-Succinimidyl(4-iodoacetyl)aminobenzoate; "Sulfo-SIAB"—N-Sulfosuccinimidyl(4-iodoacetyl) aminobenzoate; "SMPB"—Succinimidyl 4-(p-malenimidophenyl)butyrate; "Sulfo-SMPB"—Sulfosuccinimidyl 4-(p-malenimidophenyl)butyrate; "DSS"—Disuccinimidyl suberate; "BSSS"—bis(sulfosuccinimidyl) suberate; "BMH"—Bis maleimidohexane; "DFDNB"—1,5-difluoro-2,4-dinitrobenzene; "DMA"—dimethyl adipimidate 2HCl; "DMP"—Dimethyl pimelimidate-2HCl; "DMS"—dimethyl suberimidate-2-HCl; "SPDP"—N-succinimidyl-3-(2-pyridylthio)propionate; "Sulfo-HSAB"—Sulfosuccinimidyl 4-(p-azidophenyl)butyrate; "Sulfo-SAPB"—Sulfosuccinimidyl 4-(p-azidophenylbutyrate); "ASIB"—1-9p-azidosalicylamido)-4-(iodoacetamido)butane; "ASBA"—4-(p-Azidosalicylamido)butylamine. All of these linkers are available from Pierce Chemicals.

In another embodiment the linker is a small molecule such as a peptide linker. In one embodiment the peptide linker is not cleavable. In a further embodiment the peptide linker is cleavable by base, under reducing conditions, or by a specific enzyme. In one embodiment, the enzyme is indigenous. Alternatively, the small peptide may be cleavable by an non-indigenous enzyme which is administered after or in addition to the therapeutic complex. Alternatively, the small peptide may be cleaved under reducing conditions, for example, when the peptide contains a disulfide bond. Alternatively, the small peptide may be pH sensitive. Examples of peptide linkers include: poly(L-Gly), (Poly L-Glycine linkers); poly (L-Glu), (Poly L-Glutamine linkers); poly(L-Lys), (Poly L-Lysine linkers). In one embodiment, the peptide linker has the formula (amino acid)$_n$, where n is an integer between 2 and 100, preferably wherein the peptide comprises a polymer of one or more amino acids.

In a further embodiment, the peptide linker is cleavable by proteinase (Suzuki, et al. 1998 *J Biomed Mater Res* 42:112-6). In some embodiments the linker is a cleavable linker comprising, poly(ethylene glycol) (PEG) and a dipeptide, L-alanyl-L-valine (Ala-Val), cleavable by the enzyme thermolysin (Goyal, et al. 2000 *Biochem J* 345:247-254).

The chemical and peptide linkers can be bonded between the Eph receptor binding compound and the therapeutic agent by techniques known in the art for conjugate synthesis, i.e. using genetic engineering, or chemically. The conjugate synthesis can be accomplished chemically via the appropriate antibody by classical coupling reactions of proteins to other moieties at appropriate functional groups. Examples of the functional groups present in proteins and utilized normally for chemical coupling reactions are outlined as follows. The carbohydrate structures may be oxidized to aldehyde groups that in turn are reacted with a compound containing the group $H_2NNH$—R (wherein R is the compound) to the formation of a C=NH—NH—R group. The thiol group (cysteines in proteins) may be reacted with a compound containing a thiol-reactive group to the formation of a thioether group or disulfide group. The free amino group (at the amino terminus of a protein or on a lysine) in amino acid residues may be reacted with a compound containing an electrophilic group, such as an activated carboxy group, to the formation of an amide group. Free carboxy groups in amino acid residues may be transformed to a reactive carboxy group and then reacted with a compound containing an amino group to the formation of an amide group.

The therapeutic agent that is linked to the Eph receptor binding compound could be any chemical, molecule, or complex which effects a desired result. Examples include, but are not limited to, conventional pharmaceutical agents such as antibiotics, anti-neoplastic agents, immunosuppressive agents, hormones, and the like, one or more genes, antisense oligonucleotides, small interfering RNA, contrast agents, proteins, toxins, radioactive molecules or atoms, surfactant proteins, nanoparticles, or clotting proteins. The therapeutic agent may be lipophilic, a quality which will help it enter the targeted cell.

The contrast agents may be any type of contrast agent known to one of skill in the art. The most common contrast agents basically fall into one of four groups; X-ray reagents, radiography reagents, magnetic resonance imaging agents, quantum dots, nanoparticles, and ultrasound agents. The X-ray reagents include ionic, iodine-containing reagents as well as non-ionic agents such as Omnipaque (Nycomed) and Ultravist (Schering). Radiographic agents include radioisotopes as disclosed below. Magnetic Resonance Imaging reagents include magnetic agents such a Gadolinium and iron-oxide chelates. Ultrasound agents include microbubbles of gas and a number of bubble-releasing formulations.

The radionuclides may be diagnostic or therapeutic. Examples of radionuclides that are generally medically useful include: Y, Ln, Cu, Lu, Tc, Re, Co, Fe and the like such as $^{90}$Y, $^{111}$Ln, $^{67}$Cu, $^{77}$Lu, $^{99}$Tc and the like, preferably trivalent cations, such as $^{90}$Y and $^{111}$Ln.

Radionuclides that are suitable for imaging organs and tissues in vivo via diagnostic gamma scintillation photometry include the following: γ-emitting radionuclides: $^{111}$Ln, $^{113m}$Ln, $^{67}$Ga, $^{68}$Ga, $^{99m}$Tc, $^{51}$Cr, $^{197}$Hg, $^{203}$Hg, $^{169}$Yb, $^{85}$Sr, and $^{87}$Sr. The preparation of chelated radionuclides that are suitable for binding by Fab' fragments is taught in U.S. Pat. No. 4,658,839 (Nicoletti et al.) which is incorporated herein by reference.

Paramagnetic metal ions, suitable for use as imaging agents in MRI include the lanthanide elements of atomic number 57-70, or the transition metals of atomic numbers 21-29, 42 or 44. U.S. Pat. No. 4,647,447 (Gries et al.) teaches MRI imaging via chelated paramagnetic metal ions and is incorporated herein by reference.

Examples of therapeutic radionuclides are the β-emitters. Suitable β-emitters include $^{67}$Cu, $^{186}$Rh, $^{188}$Rh, $^{189}$Rh, $^{153}$Sm, $^{90}$Y, and $^{111}$Ln.

Antisense oligonucleotides have a potential use in the treatment of any disease caused by overexpression of a normal gene, or expression of an aberrant gene. Antisense oligonucleotides can be used to reduce or stop expression of that gene. Examples of oncogenes which can be treated with antisense technology and references which teach specific antisense molecules which can be used include: c-Jun and cFos (U.S. Pat. No. 5,985,558, herein incorporated by reference); HER-2 (U.S. Pat. No. 5,968,748, herein incorporated by reference) E2F-1 (Popoff, et al. U.S. Pat. No. 6,187,587; herein incorporated by reference), SMAD 1-7 (U.S. Pat. Nos. 6,159,697; 6,013,788; 6,013,787; 6,013,522; and 6,037,142, herein incorporated by reference), and Fas (Dean et al. U.S. Pat. No. 6,204,055, herein incorporated by reference).

Also provided are double-stranded RNA molecules for use in RNA interference methods in the treatment of any disease caused by overexpression of a normal gene, or expression of an aberrant gene. RNA interference (RNAi) is a process of sequence-specific gene silencing by post-transcriptional RNA degradation, which is initiated by double-stranded RNA (dsRNA) homologous in sequence to the silenced gene. A suitable double-stranded RNA (dsRNA) for RNAi contains sense and antisense strands of about 21 contiguous nucleotides corresponding to the gene to be targeted that form 19 RNA base pairs, leaving overhangs of two nucleotides at each 3' end (Elbashir et al. 2001 *Nature* 411:494-498; Bass, 2001 *Nature* 411:428-429; Zamore, 2001 *Nat Struct Biol* 8:746-750). dsRNAs of about 25-30 nucleotides have also been used successfully for RNAi (Karabinos et al. 2001 *PNAS* 98:7863-7868). dsRNA can be synthesized in vitro and introduced into a cell by methods known in the art. By such methods, translation of the target polypeptide can be decreased.

Proteins which may be used as therapeutic agents include apoptosis inducing agents such as pRB and p53 which induce apoptosis when present in a cell (Xu et al. U.S. Pat. No. 5,912,236, herein incorporated by reference), and proteins which are deleted or underexpressed in disease such as erythropoietin (Sytkowski, et al. U.S. Pat. No. 6,048,971, herein incorporated by reference)

It will be appreciated that the therapeutic agent can be any chemotherapeutic agent for neoplastic diseases such as alkylating agents (nitrogen mustards, ethylenimines, alkyl sulfonates, nitrosoureas, and triazenes), antimetabolites (folic acid analogs such as methotrexate, pyrimidine analogs, and purine analogs), natural products and their derivatives (antibiotics, alkaloids, enzymes), hormones and antagonists (adrenocorticosteroids, progestins, estrogens), and the like. Alternatively, the therapeutic agent can be an antisense oligonucleotide which acts as an anti-neoplastic agent, or a protein which activates apoptosis in a neoplastic cell.

The therapeutic agent can be any type of neuroeffector, for example, neurotransmitters or neurotransmitter antagonists may be targeted to an area where they are needed without the wide variety of side effects commonly experienced with their use.

The therapeutic agent can be an anesthetic such as an opioid, which can be targeted specifically to the area of pain. Side effects, such as nausea, are commonly experienced by patients using opioid pain relievers. The method of the present invention would allow the very specific localization of the drug to the area where it is needed, such as a surgical wound or joints in the case of arthritis, which may reduce the side effects.

The therapeutic agent can be an anti-inflammatory agent such as histamine, $H_1$-receptor antagonists, and bradykinin. Alternatively, the anti-inflammatory agent can be a non-steroidal anti-inflammatory such as salicylic acid derivatives, indole and indene acetic acids, and alkanones. Alternatively, the anti-inflammatory agent can be one for the treatment of asthma such as corticosteroids, cromollyn sodium, and nedocromil. The anti-inflammatory agent can be administered with or without the bronchodilators such as $B_2$-selective andrenergic drugs and theophylline.

The therapeutic agent can be a diuretic, a vasopressin agonist or antagonist, angiotensin, or renin which specifically effect a patient's blood pressure.

The therapeutic agent can be any pharmaceutical used for the treatment of heart disease. Such pharmaceuticals include, but are not limited to, organic nitrites (amyl nitrites, nitroglycerin, isosorbide dinitrate), calcium channel blockers, antiplatelet and antithrombotic agents, vasodilators, vasoinhibitors, anti-digitalis antibodies, and nodal blockers.

The therapeutic agent can be any pharmaceutical used for the treatment of protozoan infections such as tetracycline, clindamycin, quinines, chloroquine, mefloquine, trimethoprimsulfamethoxazole, metronidazole, and oramin. The ability to target pharmaceuticals or other therapeutics to the area of the protozoal infection is of particular value due to the very common and severe side effects experienced with these antibiotic pharmaceuticals.

The therapeutic agent can be any anti-bacterial such as sulfonamides, quinolones, penicillins, cephalosporins, aminoglycosides, tetracyclines, chloramphenicol, erythromycin, isoniazids and rifampin.

The therapeutic agent can be any pharmaceutical agent used for the treatment of fungal infections such as amphotericins, flucytosine, miconazole, and fluconazole.

The therapeutic agent can be any pharmaceutical agent used for the treatment of viral infections such as acyclovir, vidarabine, interferons, ribavirin, zidovudine, zalcitabine, reverse transcriptase inhibitors, and protease inhibitors. It can also be envisioned that virally infected cells can be targeted and killed using other therapeutic agent, such as toxins, radioactive atoms, and apoptosis-inducing agents.

The therapeutic agent can be chosen from a variety of anticoagulant, anti-thrombolyic, and anti-platelet pharmaceuticals.

It will be appreciated that diseases resulting from an over- or under-production of hormones can be treated using such therapeutic agent as hormones (growth hormone, androgens, estrogens, gonadotropin-releasing hormone, thyroid hormones, adrenocortical steroids, insulin, and glucagon). Alternatively, if the hormone is over-produced, antagonists or antibodies to the hormones may be used as the therapeutic agent.

Various other possible therapeutic agents include vitamins, enzymes, and other under-produced cellular components and toxins such as diptheria toxin or botulism toxin.

Alternatively, the therapeutic agent may be one that is typically used in in vitro diagnostics. Thus, the ligand and linker are labeled by conventional methods to form all or part of a signal generating system. The ligand and linker can be covalently bound to radioisotopes such as tritium, carbon 14, phosphorous 32, iodine 125 and iodine 131 by methods well known in the art. For example, $^{125}I$ can be introduced by procedures such as the chloramine-T procedure, enzymatically by the lactoperoxidase procedure or by the prelabeled Bolton-Hunter technique. These techniques plus others are discussed in H. Van Vunakis and J. J. Langone, Eds, *Methods in Enzymology*, Vol. 70, Part A, 1980. See also U.S. Pat. Nos. 3,646,346, and 4,062,733, both of which are herein incorporated by reference, for further examples of radioactive labels.

Alternatively, the therapeutic agent can be a prodrug or a promolecule which is converted into the corresponding pharmaceutical agent by a change in the chemical environment or by the action of a discrete molecular agent, such as an enzyme. Preferably, the therapeutic agent is administered with the specific molecule needed for conversion of the promolecule. Alternatively, the promolecule can be cleaved by a natural molecule found in the microenvironment of the target tissue. Alternatively, the prodrug is pH sensitive and converted upon change in environment from the blood to the cell or intracellulart vesicles (Greco et al. 2001 *J Cell Physiol* 187:22-36).

An effective amount of conjugate that is administered to the mammal can range from about 0.001 mg to about 50 mg/kg of body weight per day. The effective amount will depend on factors, including but not limited to, the route by which the conjugate is administered, binding affinity of the conjugate, Eph receptor expression level in target cells, and Eph receptor expression level in nontarget cells. It will be appreciated, however, that determination of an effective amount of agonist can be readily determined by one of ordinary skill in the art.

Another aspect of the present invention includes pharmaceutical compositions comprising, as an active ingredient, at least one of the peptides, peptidomimetics or small molecules disclosed herein in association with a pharmaceutical carrier or diluent. These compounds can be administered by oral, pulmonary, parenteral (intramuscular, intraperitoneal, intravenous, or subcutaneous injection), inhalational (via a fine powder formulation, or aerosol), transdermal, nasal, vaginal, rectal, or sublingual routes of administration and can be formulated in dosage forms appropriate for each route of administration. See, for example, Bernstein, et al. PCT Patent Publication No. WO 93/25221; Pitt, et al. PCT Patent Publication No. WO 94/17784; and Pitt, et al. European Patent Application 613,683, each of which is incorporated herein by reference.

Solid dosage forms for oral administration include capsules, tablets, pills, powders, and granules. In such solid dosage forms, the active compound is admixed with at least one inert pharmaceutically acceptable carrier such as sucrose, lactose, or starch. Such dosage forms can also comprise, as is normal practice, additional substances other than inert diluents, for example, lubricating agents such as magnesium stearate. In the case of capsules, tablets, and pills, the dosage forms may also comprise buffering agents. Tablets and pills can additionally be prepared with enteric coatings.

Liquid dosage forms for oral administration include pharmaceutically acceptable emulsions, solutions, suspensions, syrups, with the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

The compositions containing the compounds can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective dose". Amounts effective for this use will depend on the severity of the disease and the weight and general state of the patient.

The compositions described herein can also be microencapsulated by, for example, the method of Tice and Bibi (in: *Treatise on Controlled Drug Delivery*, ed. A. Kydonieus, Marcel Dekker, N.Y. 1992, pp. 315-339), which is hereby incorporated by reference in its entirety.

In prophylactic applications, compositions containing the compounds disclosed herein are administered to a patient susceptible to or otherwise at risk of a particular disease. Such an amount is defined to be a "prophylactically effective dose". In this use, the precise amounts again depend on the patient's state of health and weight, and can be readily determined by one of ordinary skill in the art.

The quantities of the Eph receptor agonist necessary for effective therapy will depend upon many different factors, including means of administration, target site, physiological state of the patient, and other medications administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, for example, in: Gilman, et al. (eds.), 1990 *Goodman and Gilman's: The Pharmacological Basis of Therapeutics* 8th ed., Pergamon Press; and *Remington's Pharmaceutical Sciences*, 7th Ed., Mack Publishing Co., Easton, Pa. (1985), each of which is hereby incorporated by reference.

The peptides and peptidomimetics described herein are effective in treating Eph receptor mediated conditions when administered at a dosage range of from about 0.001 mg to about 50 mg/kg of body weight per day. The specific dose employed is regulated by the particular condition being treated, the route of administration as well as by the judgement of the attending clinician depending upon factors such as the severity of the condition, the age and general condition of the patient, and the like. Such doses can be readily determined by those of skill in the art.

For parenteral administration, the peptides can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (for example, sodium chloride, mannitol) and chemical stability (for example, buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions described herein can be administered as a single dose or in multiple doses; administered either as individual therapeutic agents or in combination with other therapeutic agents; and combined with conventional therapies, which may be administered sequentially or simultaneously.

The compounds can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are generally known to those skilled in the art.

The Eph receptor binding compounds described herein can be formulated into a pharmaceutical composition wherein the compound is the only active agent therein. Alternatively, the pharmaceutical composition can contain additional active agents. For example, two or more Eph receptor binding compounds described herein may be used in combination. Moreover, the peptide compound can be combined with one or more other agents that have modulatory effects on Eph receptor activity.

Use of Phage Display to Identify Peptides that Bind Selectively to Eph Family Members Phage display can be used to isolate peptides that specifically bind to each of the sixteen known Eph receptors. As described herein, several phage displayed peptides that specifically bind EphA2, EphA4, EphA5, EphA7, EphB2, or EphB4 have been isolated many of which bind selectively. Accordingly, panning random peptide libraries against any of the sixteen known members of the Eph receptor family can be used to obtain peptides that bind selectively to an Eph receptor of interest. The clones can be identified by sequencing techniques well known in the art. The length of the peptides contained in the peptide libraries can be modulated to obtain peptides that possess both high binding selectivity and high binding affinity.

Other Utility

The compounds described herein are useful in vitro as unique tools for understanding the biological role of Eph receptors, including the evaluation of the many factors thought to influence, and be influenced by, the production of ephrin ligands and the receptor binding process. The present compounds are also useful in the development of other compounds that bind to and activate Eph receptors, because the present compounds provide important information on the relationship between structure and activity to facilitate such development.

The compounds are also useful as competitive binders in assays to screen for new Eph receptor agonists. In such assay embodiments, the compounds described herein can be used without modification or can be modified in a variety of ways; for example, by labeling, such as covalently or non-covalently joining a moiety which directly or indirectly provides a detectable signal. In any of these assays, the materials thereto can be labeled either directly or indirectly. Possibilities for direct labeling include label groups such as: radiolabels such as $^{125}I$, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups. The compounds may also include spacers or linkers in cases where the compounds are to be attached to a solid support.

Nuclear magnetic resonance (NMR) spectroscopy is known for its ability to characterize macromolecular structures, and is a technique for investigating both static and transient features of ligand binding to a target molecule (Pellecchia, et al. 2002 *Nature Rev Drug Disc* 1:211). NMR spectroscopy is a useful tool for determining the binding of ligands to target molecules, and has the advantage of being able to detect and quantify interactions with high sensitivity without requiring prior knowledge of protein function. Furthermore, NMR spectroscopy can provide structural information on both the target and the ligand to aid subsequent optimization of weak-binding hits into high-affinity leads.

Methods of detecting binding of a ligand compound to a target biomolecule by generating first and second nuclear magnetic resonance correlation spectra from target biomolecules which have been uniformly labeled are reported in U.S. Pat. Nos. 5,698,401 and 5,804,390. The first spectrum is generated from data collected on the target substance in the absence of ligands, and the second in the presence of one or more ligands. A comparison of the two spectra permits determination of which compounds in the mixture of putative ligands bind(s) to the target biomolecule.

Eph receptors may be selectively labeled by incorporation of $^{1}H$, $^{13}C$, $^{15}N$ and/or $^{19}F$ into the side chain of one or more amino acid residues. Selectively labeled complexes of an Eph receptor bound to an Eph receptor binding ligand, can be exposed to a second molecule and any molecular interaction can be examined by NMR spectroscopy. For example, 2D 13C,1H-HMQC (heteronuclear multiple quantum coherence) and 13C-edited 1H,1H-NOESY NMR experiments can be used to detect molecular interaction and to determine the dissociation constant for any complex. In addition, a predictive model can be created based on the three-dimensional structure of the target and from the relative position of the ligand with respect to the labeled side chain. The use of several different labeled side-chains in a single, selectively-labeled, target-molecule will improve the resolution as well as the predictive nature of the model.

Because non-peptidic small molecules may be more suitable than peptides for clinical development, High Throughput Screening can be used to screen chemical libraries for small molecules that disrupt the Eph-ephrin complex. The assay uses immobilized Eph receptor ectodomains in complex with ephrin-alkaline phosphatase fusion proteins. The ability to decrease bound alkaline phosphatase activity will identify small molecule inhibitors of the Eph-ephrin interaction.

Moreover, based on their ability to selectively bind to Eph receptors, the peptides described herein can be used as reagents for selectively detecting Eph receptors on living cells, fixed cells, in biological fluids, in tissue homogenates, in purified, natural biological materials, etc. For example, by labeling peptides described herein, one can selectively identify cells having receptors such as EphA2, EphA4, EphA5, EphA7, EphB2 or EphB4 on their surfaces. In addition, based on their ability to bind Eph receptors, the peptides can be used in in situ staining, FACS (fluorescence-activated cell sorting), Western blotting, ELISA, etc. In addition, based on their ability to selectively bind Eph receptors, the peptides can be used in receptor purification, or in purifying cells expressing only specific Eph receptors on the cell surface (or inside permeabilized cells).

The compounds described herein can also be utilized as commercial reagents for various medical research and diagnostic uses. Such uses include but are not limited to: (1) use as a calibration standard for quantitating the activities of candidate Eph agonists in a variety of functional assays; (2) use to maintain the proliferation and growth of Eph-dependent cell lines; (3) use in structural analysis of the Eph-receptor ligand-binding interfaces through co-crystallization; (4) use to investigate the mechanism of Eph signal transduction/receptor activation; (5) other research and diagnostic applications wherein the Eph-receptor is preferably activated or such activation is conveniently calibrated against a known quantity of an Eph agonist, and the like; and (6) other research and diagnostic applications wherein the Eph-receptor is preferably inhibited or such inhibition is conveniently calibrated against a known quantity of an Eph antagonist, and the like.

EXAMPLES

The following examples describe the processes used to identify peptides that target EphA2, EphA4, EphA5, EphA7, EphB2, and EphB4 receptors.

Synthetic Peptides

In the examples that follow, biotinylated peptides, containing a carboxy-terminal GSGSK (SEQ ID NO: 30) linker, were synthesized using Fmoc-chemistry, purified by HPLC, and verified by MALDI-TOF mass spectrometry. Additional information on the preparation of the peptides and peptidomimetics described herein is provided below.

Plasmids

The ephrin-A5-AP and ephrin-A6-AP plasmids have been described (Menzel, P. et al. 2001 *Dev Biol* 230:74-88). To construct the EphA2 AP (EphA2-AP) plasmid, the globular amino-terminal region of human EphA2 (aa 1-219, GenBank Accession # M36395) was amplified by PCR and cloned into the APtag-2 vector (Cheng, H. J. & Flanagan, J. G. 1994 *Cell* 79:157-168). The expression plasmid was transiently transfected into 293T cells using Superfect transfection reagent (Qiagen). Cell culture supernatants containing the AP fusion proteins were centrifuged to eliminate cell debris, supplemented with 20 mM Hepes, and stored frozen at −20 C.

It will be appreciated that similar expression plasmids, which contain a nucleic acid encoding Eph-AP fusion proteins, can be constructed and expression of the encoded fusion proteins can be achieved using methods similar to those described above.

Example 1

Identification of Peptides that Target EphA2

This example describes the method used to obtain peptides that bind to EphA2. An M13 phage library (New England Biolabs, Beverly, Mass.) displaying random 12-mer peptides was used for panning on EphA2. A histidine-tagged mouse EphA2 Fc fusion protein (R&D Systems, Minneapolis, Minn.) was incubated overnight at 4° C. in nickel-nitrilotri-acetic acid (Ni-NTA)-coated ELISA plates at concentrations of 1-10 μg/ml in Tris-buffered saline (TBS) (150 mM NaCl, 50 mM Tris-HCl, pH 7.5). Wells were blocked with 0.5% bovine serum albumin (BSA) in TBS, and rinsed with binding buffer (TBS, 1 mM $CaCl_2$, 0.1% Tween 20). Control wells were coated with bovine serum albumin (BSA) using the above methods.

In round 1 of EphA2 panning, $1.7 \times 10^{11}$ plaque forming units (PFUs) of the phage library in 100 μl binding buffer were incubated for 1 hour at room temperature in an EphA2-coated well. Phage remaining bound after washing were eluted with 100 μl of 0.2 M glycine-HCl, pH 2.2 or 100 μg ephrin-A1 Fc. The entire eluate was used to infect early-log phase ER2738 host bacteria and amplified. The phage were concentrated and stored according to the manufacturer's recommendations. In rounds 2 and 3, $2 \times 10^{11}$ PFUs amplified phage pool from the previous round were added to an EphA2 Fc-coated well and a BSA-coated control well. The phage were panned as described for round 1, except that the Tween concentration in the wash buffer was 0.5%, and eluted phage were titered to assess enrichment.

Figure 1B:
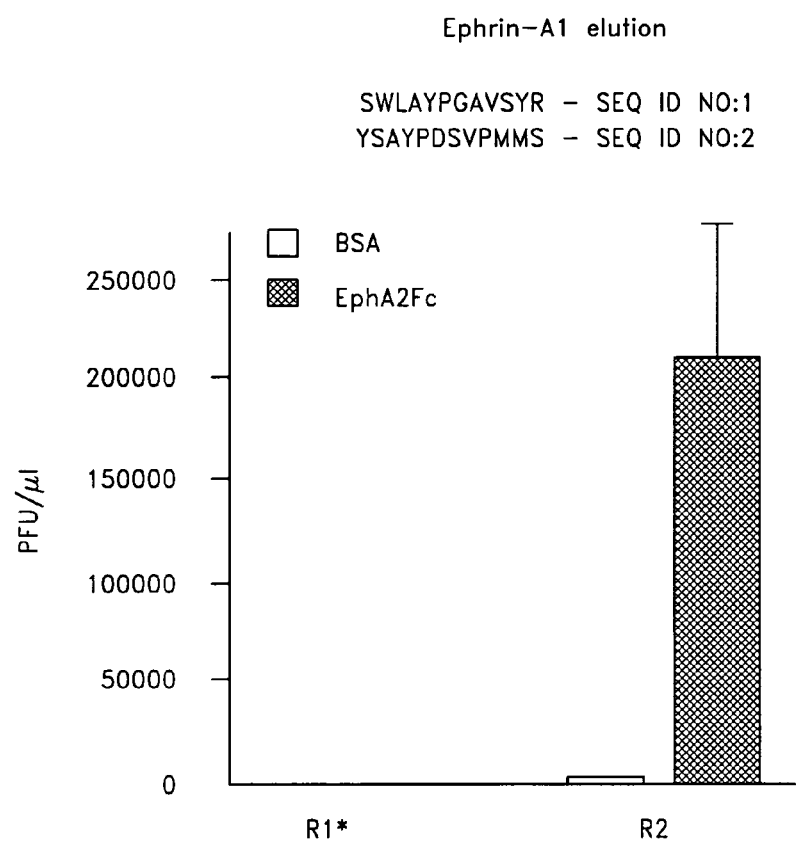
FIG. 1B is a bar graph which shows the titer (pfu/µl) of phage, from a random 12-mer phage display library, obtained over successive rounds of panning (R1-R2) against either immobilized EphA2 Fc or immobilized bovine serum albumin (BSA). Bound phage were eluted with ephrin-A1. Peptide sequences of the obtained EphA2-binding clones are shown.

FIGS. 1A and 1B show the results of testing to identify two peptides that bind selectively and with high affinity to EphA2. FIG. 1A shows bound phage eluted with a low pH solution to maximize phage recovery whereas FIG. 1B shows elution of bound phage with ephrin-A1 to improve recovery of peptides that interact with the ligand-binding site of EphA2. After several rounds of selection on EphA2, the screen yielded approximately 17-fold (low pH elution) and 115-fold (ephrin-A1 elution) enrichment of phage binding to EphA2 versus phage binding to BSA. In contrast, panning on ephrin-A1 did not result in phage enrichment and was not pursued further (results not shown).

Nineteen of the 20 individual phage clones from the pool eluted with low pH were found to specifically, bind to EphA2 Fc when compared to ephrin-A1 Fc, which was used as a negative control. All 19 clones were found to display the same peptide: SWLAYPGAVSYR (SWL peptide) (SEQ ID NO: 1). Furthermore, nine of 10 phage clones from the pool eluted with ephrin-A1 bound specifically to EphA2. Seven of these clones displayed the SWL peptide and two displayed the peptide YSAYPDSVPMMS (YSA peptide) (SEQ ID NO: 2).

The above method was also used to find peptides that bound to EphA4, EphA5, EphA7, EphB2 and EphB4 by panning the phage library against the appropriate immobilized receptor Fc fusion. The results of such panning experiments are described in the Examples below.

Example 2

The YSA and SWL Peptides Bind Specifically to EphA2

In this example, immobilized SWL and YSA peptides were used to capture Fc fusion proteins of various EphA receptors. Biotinylated peptides were captured on streptavidin-coated microtiter plates (Pierce, Rockford, Ill.) and incubated with Eph receptor Fc fusion proteins. Bound Eph receptors were detected with anti-human Fc antibody conjugated to alkaline phosphatase (AP) (Promega, Madison, Wis.). Alternatively, the immobilized biotinylated peptides were incubated with diluted cell culture supernatants containing EphA2-AP. Substrates were 2,2'-azino-bis(3-ethylbenzthiazoline-6-sulfonic acid) for horseradish peroxidase and p-nitrophenyl phosphate for AP. Absorbance at 405 or 450 nm was measured using an ELISA plate reader.

Figure 2:
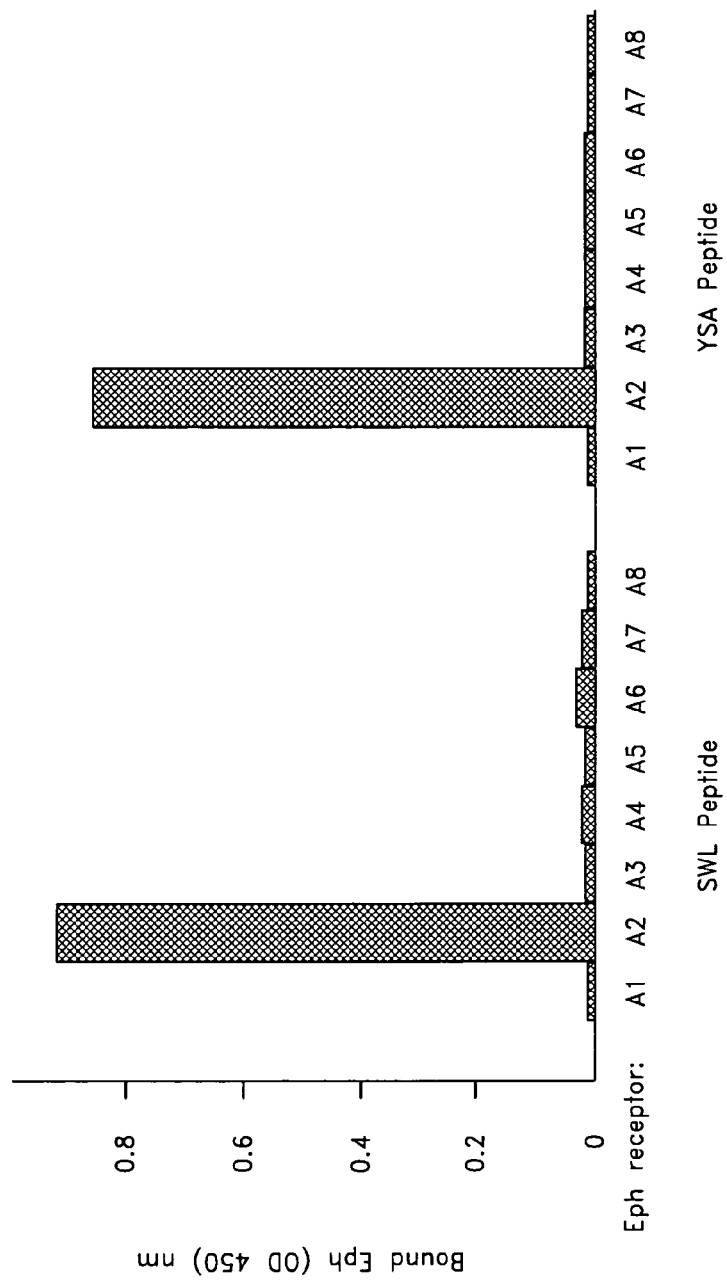
FIG. 2 is a bar graph which illustrates the binding specificity between immobilized SWL and YSA peptides and EphA2 Fc versus Fc fusion proteins of other EphA receptors.

The corresponding synthetic SWL and YSA peptides were found to bind specifically to EphA2. In particular, both SWL and YSA bound to EphA2 but not to other EphA receptors (FIG. 2) additionally these peptides have been shown to lack the ability to bind to receptors of the EphB family.

Example 3

Characterization of the Binding Interaction between EphA2 and Binding Peptides In this example, a BIAcore system was used to characterize the binding interaction between EphA2 and the peptides discovered in Example 1. EphA2 Fc was covalently coupled to activated biosensor chips and the equilibrium binding of peptides at various concentrations was determined by measuring changes in surface plasmon resonance using the BIAcore 3000. The chips were regenerated by washing with 1 M $Na_2CO_3$, pH 10.5. Equilibrium binding data obtained by surface plasmon resonance indicated that the YSA peptide binds to EphA2 with higher affinity ($K_D$=186 nM±7) than the SWL peptide ($K_D$=678 nM±23) (compare FIGS. 3A and 3B).

Example 4

The YSA and SWL Peptides Target EphA2 on the Cell Surface

This example demonstrates that both the YSA and SWL peptide bind to EphA2 on the surface of cells in culture. The affinity of the YSA peptide for EphA2 is much greater than that of the SWL peptide in each of the tested cell types.

Equal amounts of wild type control phage (WT) and phage displaying the SWL and YSA peptides were incubated with MDA-MB-435 human breast cancer cells overexpressing the extracellular and transmembrane domains of EphA2 fused to enhanced green fluorescent protein (EGFP) (MDA EphA2-EGFP) (Ogawa, K. et al. 2000 *Oncogene* 19:6043-6052), untransfected MDA-MB-435 cells (MDA WT), or adherent human umbilical vein endothelial (HUVE) cells. Binding was performed using MDA cells in suspension and adherent HUVE cells. In particular, phage binding to cells was quantitated either by incubating $1\times10^9$ PFUs for 60-90 minutes at 37 C with $1\times10^6$ MDA-MB-435 cells in a 0.5 ml suspension or by adding $1\times10^{10}$ PFUs directly to confluent monolayers of HUVE cells in 24 well tissue culture plates. The phage were diluted into either Dulbecco's Modified Eagle's Medium with 1% BSA (MDA-MB-435 cells) or Endothelial Basal Medium-2 (EBM-2) (Clonetics Products, BioWhittaker, Inc., Walkersville, Md.) with 1% BSA, 10 mM Hepes (HUVE cells).

The YSA phage exhibit 50-fold higher binding than wild type phage to MDA-MB-435 human breast cancer cells overexpressing the EphA2 extracellular domain on their surface. The SWL phage instead exhibits 7-fold higher binding (FIG. 4A). In the case of untransfected MDA-MB-435 cells, which express only low levels of endogenous EphA2, the YSA phage show a 2.5-fold higher binding than wild type phage whereas the SWL phage does not show specific binding (FIG. 4B). The YSA phage also exhibit 12-fold higher binding than wild type phage to human umbilical vein endothelial (HUVE) cells, which express moderate levels of EphA2. In contrast, the SWL phage does not specifically bind to these cells (FIG. 4C).

Example 5

The YSA Peptide Stimulates Tyrosine Phosphorylation of EphA2 and Activates Downstream Signaling This example shows that the YSA peptide stimulates tyrosine phosphorylation of EphA2 and activates downstream signaling events that are attributed to the activation of this receptor.

Human umbilical vein endothelial (HUVE) cells were grown in microvascular endothelial cell medium-2 (EGM-2 MV) (Clonetics) with 10% FCS and serum-starved in EBM-2 for 2 hours prior to stimulation with 2 µg/ml ephrin-A1 Fc or Fc protein in the presence or absence of YSA peptide. Ephrin-A1 Fc was cross-linked by preincubation with 0.2 µg/ml anti-human Fc antibodies for 30 minutes on ice. After stimulation, the cells were lysed in modified RIPA buffer (Ogawa, K. et al. 2000 *Oncogene* 19: 6043-6052). Cell lysates were immunoprecipitated with 5 µg anti-EphA2 antibody (Upstate, Lake Placid, N.Y.), separated by SDS polyacrylamide gel electrophoresis and probed by immunoblotting with peroxidase-conjugated anti-phosphotyrosine antibody (Transduction Laboratories, San Diego, Calif.) or anti-EphA2 antibody followed by a secondary anti-mouse IgG peroxidase-conjugated antibody (Amersham).

In an alternative method, non-serum starved HUVE cells were stimulated with 2 µg/ml ephrin-A1 Fc or Fc protein in the presence or absence of YSA peptide. Cell lysates were used to immunoprecipitate EphA2 as described above or probed by immunoblotting with anti-phospho-p44/p42 MAPK antibody (Cell Signaling Technology, Beverly, Mass.) followed by an anti-mouse IgG peroxidase-conjugated antibody (Arnersham) and re-probed with an anti-ERK2 antibody (Santa Cruz Biotechnology, Santa Cruz, Calif.) followed by a secondary anti-rabbit IgG peroxidase-conjugated antibody (Amersham). Erk2 (p42 MAP kinase) is the major phosphorylated form present. EphA2 was immunoprecipitated (IP) and probed by immunoblotting with anti-phosphotyrosine (PTyr) or anti-EphA2 antibodies.

Figure 5:
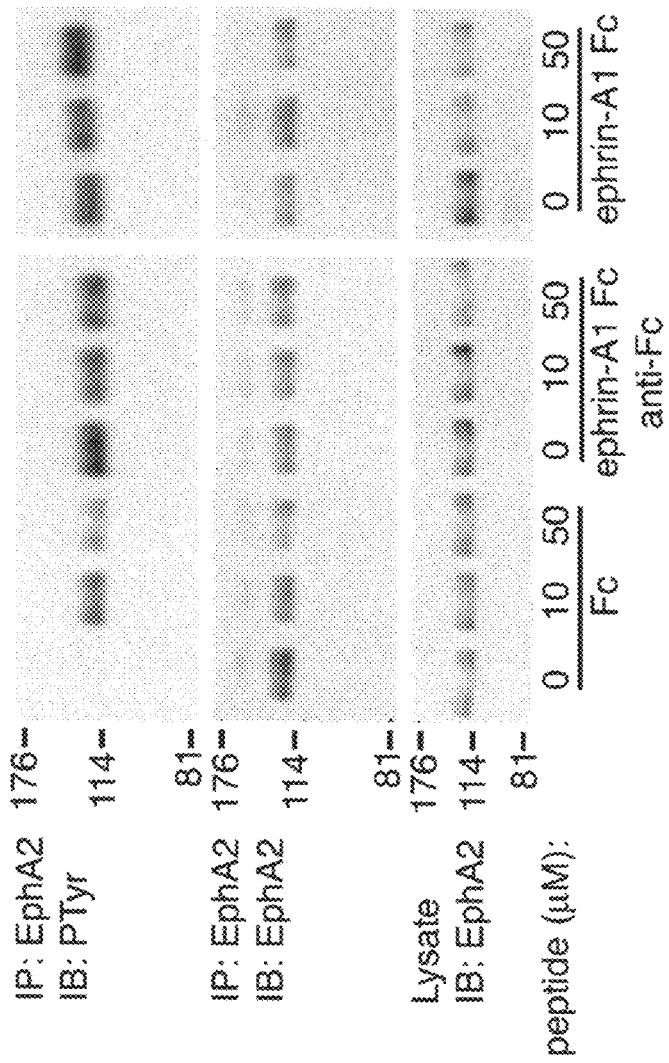
FIG. 5 is an immunoblot showing the phosphorylation of EphA2 in HUVE cells treated with either 0, 10 or 50 μM YSA peptide prior to treatment with Fc (lanes 1-3), ephrin-A1-Fc anti-Fc crosslinked complexes (lanes 4-6) and ephrin-A1-Fc (lanes 7-9). EphA2 was immunoprecipitated (IP) and probed by immunoblotting (IB) with anti-phosphotyrosine (PTyr) or anti-EphA2 antibodies.
Figure 6A:
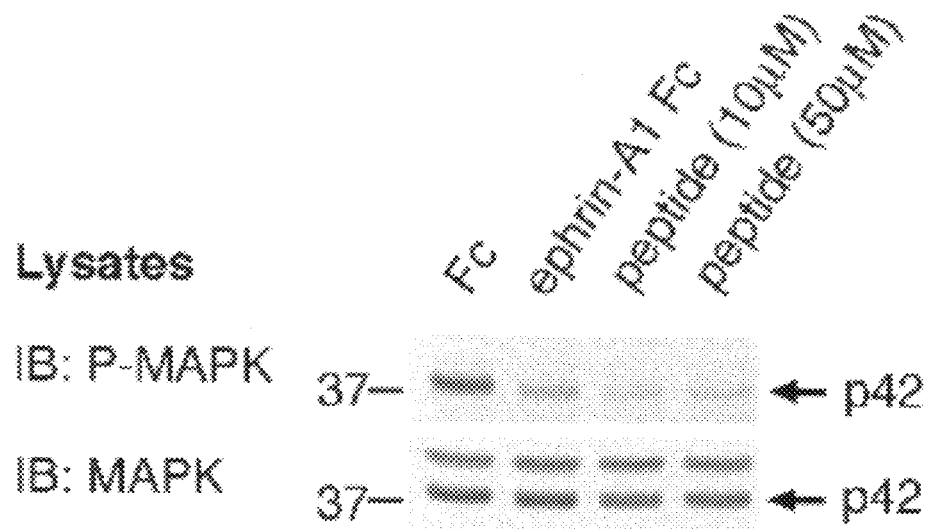
FIGS. 6A and 6B are immunoblots showing the inhibition of phosphorylation of MAP kinase (MAPK) in HUVE cells treated with the YSA peptide prior to Fc treatment (6A) (lanes 3 and 4) and the corresponding phosphorylation of EphA2 (6B) (lanes 3 and 4). IB designates immunoblot and IP designates immunoprecipitation prior to immunoblot.
Figure 6B:
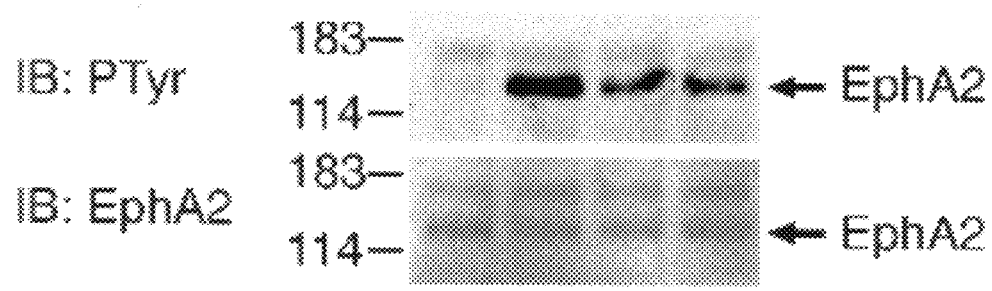

In addition to binding to EphA2 in HUVE cells the YSA peptide stimulates tyrosine phosphorylation of the receptor and downstream signaling in the absence of ephrin and does not decrease EphA2 phosphorylation in the presence of ephrin (FIG. 5). Furthermore, it was found that the YSA peptide activates a previously described Eph2A signaling pathway that suppresses MAP kinase activation (see Miao, et al. 2001 *Nature Cell Biol*. 3: 527-530 for a discussion of suppression of MAP kinase activation via the Eph2A signaling pathway). The suppression of MAP kinase in response to stimulation by the YSA peptide is shown in FIG. 6A while the corresponding phosphorylation of EphA2 in response to the YSA peptide is shown in FIG. 6B. Thus, the YSA peptide is an agonist for EphA2. Similar results have been obtained for the SWL peptide, which therefore is also an agonist for EphA2.

Example 6

The YSA and SWL Peptides Inhibit Ephrin-A Binding to EphA2

This example shows that YSA and SWL peptides inhibit the binding of ephrin-A5 and ephrin-A6 in a concentration dependent manner. Ephrin binding to Eph receptor-coated plates was quantified using alkaline phosphatase (AP) fusion proteins of ephrin-A5 and ephrin-A6 (plasmids encoding these AP-fusions are described above). Diluted cell culture supernatants containing ephrin-A5-AP and ephrin-A6-AP were co-incubated with peptides in microtiter wells coated with EphA2 Fc or EphA4 Fc. Ephrins remaining bound after washing were detected by measuring AP activity.

The YSA and SWL peptides inhibit, in a concentration dependent manner, the binding of A-ephrins to immobilized EphA2 but not EphA4 (FIGS. 7A and 7B). This suggests that the peptides bind to the surfaces of EphA2 that interact with the ephrins. ELISA assays confirmed that the YSA and SWL peptides bind to the globular ligand-binding domain of EphA2. The globular ligand-binding domain has been shown to contain two distinct ephrin-binding regions at the amino terminus of the receptor (Labrador, J. P. et al. 1997 *EMBO J* 16:3889-3897; Himanen, J. P. et al. 1998 *Nature* 396:486-491).

Example 7

The SWL and YSA Bind the Same or Overlapping Sites on EphA2

In this example, the binding site of the YSA and SWL peptides was characterized using competition experiments with phage-displayed peptides. Phage binding to Eph receptor-coated plates was quantified using an anti-phage antibody conjugated to horseradish peroxidase (M13 phage detection kit, Amersham Pharmacia Biotech., Piscataway, N.J.). For peptide competition assays with phage clones, Ni-NTA microtiter wells coated with EphA2 Fc were incubated for 1 hour at room temperature with phage clones diluted between 1:600 and 1:9,000 in binding buffer (100 µl/well). Unbound phage were washed away and competing peptides were added for 1 hour. Alternatively, peptides and phage were co-incubated together.

Figure 8:
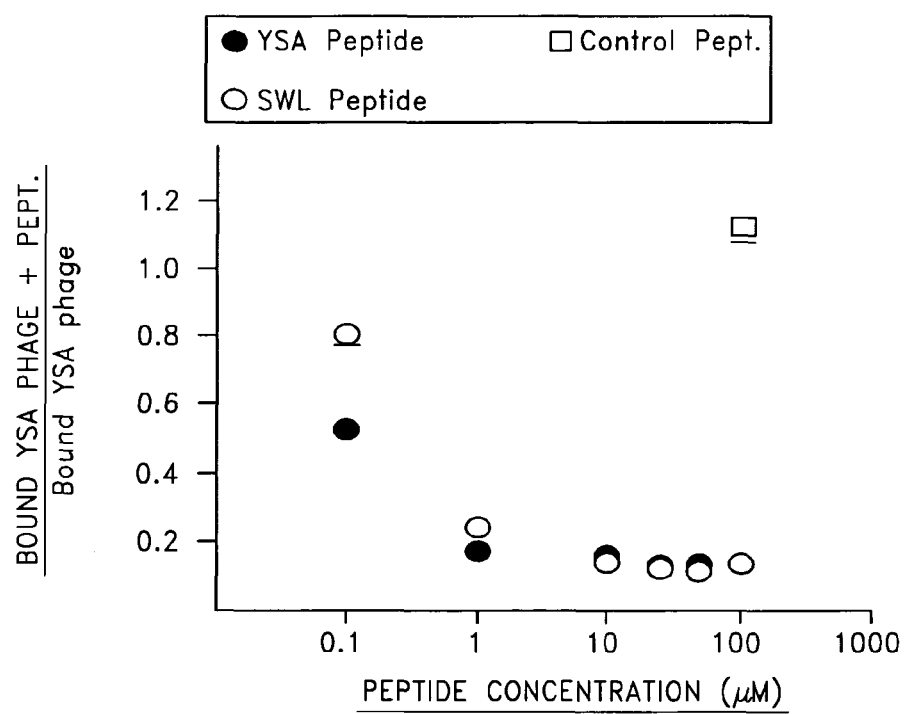
FIG. 8 is a graph which shows that SWL and YSA peptides bind the same or overlapping sites on EphA2.

SWL and YSA peptides were shown to have affinity for the same or overlapping sites. Synthetic SWL peptide competes with YSA phage bound to immobilized EphA2 and conversely YSA peptide competes with SWL phage (FIG. 8). Accordingly, these results indicate that the YSA and SWL peptides bind to the same or overlapping sites on EphA2.

Example 8

Figures 10A, 10B:
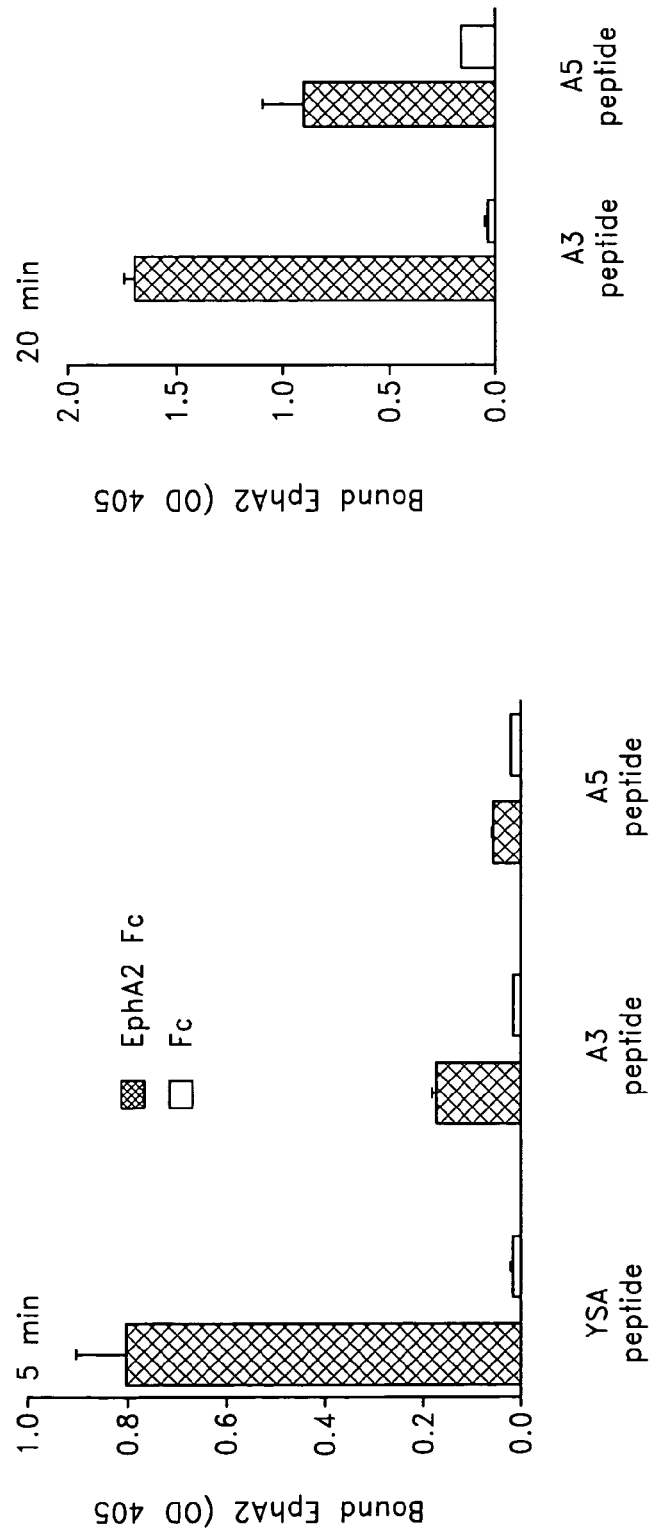
FIGS. 10A and 10B are bar graphs which illustrate the results of binding between biotinylated A3, A5, and YSA peptides immobilized on streptavidin-coated wells used to capture EphA2 Fc. OD readings at 5 minutes (10A) and 20 minutes (10B) are shown.
Figure 11A:
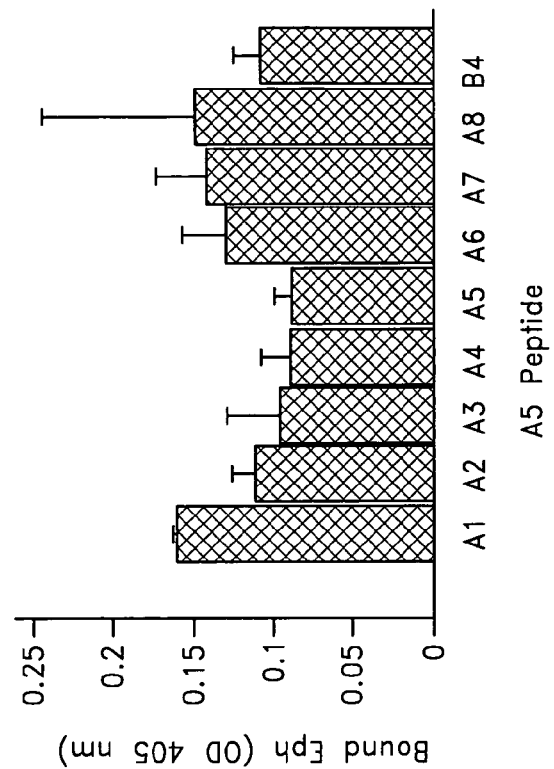
FIGS. 11A and 11B are bar graphs showing the results of binding between biotinylated A3 and A5 peptides immobilized on streptavidin-coated wells and Fc fusion proteins of EphA receptors. Error bars in all panels show standard deviation from duplicate measurements.
Figure 11B:
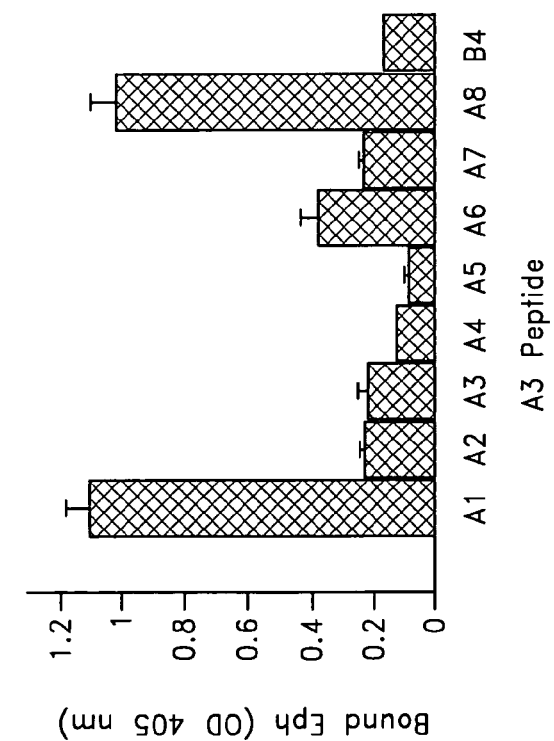

Peptides Corresponding to Ephrin Sequences Bind to Eph Receptors Promiscuously and Weakly This example shows that other sequences having similarities to both the SWL and YSA peptides bind to a variety of different Eph receptors with low affinity. FIG. 9A shows that both YSA and SWL peptides, which have related sequences, have some similarity with a high affinity Eph receptor binding interface (the G-H loop of the A-ephrins) (see Himanen, J. P. et al. 2001 *Nature* 414:933-938). When the sequences of the SWL and YSA peptides are considered in reverse order, similarity to a lower affinity receptor binding interface (the A-A' β-strand) is displayed (FIG. 9B). Twelve-mer synthetic peptides corresponding to the G-H loop of ephrin-A3 (A3 peptide, FIG. 9A) and the A-A' β-strand of ephrin-A5 (A5 peptide, FIG. 9B) indeed bind EphA2, albeit more weakly than the YSA peptide (FIGS. 10A and 10B). Even a longer A5 peptide containing additional receptor-binding residues (VADRYAVYWNSSNPR) (SEQ ID NO: 19) exhibits a similar weak binding. Interestingly, the A3 and A5 peptides bind promiscuously to all EphA receptors—similar to A-ephrins—and even to EphB4 (FIGS. 11A and 11B) (*Eph-Nomenclature-Committee Unified nomenclature for Eph family receptors and their ligands, the ephrins* 1997 *Cell* 90:403-404).

The competition methods discussed in Example 7 were used to determine the binding affinity of certain ephrin-related sequences. In particular, it was found that the A3 peptide did not inhibit phage binding (FIG. 14), suggesting that the A3 peptide which presumably binds to the high affinity ephrin-binding site may bind too weakly to compete. Indeed, the A3 peptide also did not compete with ephrin-A5 for binding to EphA2. In contrast, the A5 peptide enhanced both phage and ephrin-A5 binding to EphA2. Taken together, these results suggest that binding of the A5 peptide to the low affinity ephrin-binding site of EphA2 enhances binding of ephrins and YSA and SWL peptides to the high affinity site.

Example 9

Identification of Peptides the Bind to Eph Receptors

This example shows that phage display can be used to successfully discover additional peptides that bind to Eph receptors of various classes. The methods described in Example 1 were used to identify other peptides that could bind to EphA4, EphA5, EphA7, EphB4 and EphB2. The following table displays the peptide name, receptor affinity, peptide sequence and the SEQ ID NO of each of the 12-mer peptides that have currently been shown to bind to EphA or EphB family receptors.

TABLE 1

Sequences of Peptides that Bind Eph Family Receptors

| Peptide Name | Receptor Affinity | Peptide Sequence | SEQ ID NO: |
|---|---|---|---|
| SWL | EphA2 | SWLAYPGAVSYR | 1 |
| YSA | EphA2 | YSAYPDSVPMMS | 2 |
| APY | EphA4 | APYCVYRGSWSC | 20 |
| KYL | EphA4 | KYLPYWPVLSSL | 21 |
| VTM | EphA4 | VTMEAINLAFPG | 22 |
| DAL | EphB4 | DALNDWLLFRPW | 23 |
| IPW | EphB4 | IPWTQHMAMSPM | 24 |
|  | EphB4 | SVSVGMKPSPRP | 25 |
| SGH | EphB4 | SGHQLLLNKMPN | 26 |

TABLE 1-continued

Sequences of Peptides that Bind Eph Family Receptors

| Peptide Name | Receptor Affinity | Peptide Sequence | SEQ ID NO: |
|---|---|---|---|
| SLR | EphA5 | SLRDTYMRAKVL | 27 |
| WDC | EphA5 | WDCNGPYCHWLG | 28 |
| WTF | EphA5 | WTFPVLWDDKHP | 29 |
|  | EphB4 | GPVADAWLVYPR | 31 |
| NPV | EphB4 | NPVIGPIQRAWT | 32 |
| DHN | EphB4 | DHNHDLYNPWRL | 33 |
| TNY | EphB4 | TNYLFSPNGPIA | 34 |
|  | EphB4 | LPHGPVAAAWDA | 35 |
|  | EphB4 | TYFDFQAWSIRA | 36 |
|  | EphB4 | EWYMKFPPEHYF | 37 |
|  | EphB4 | GPVHRAWEPTSH | 38 |
|  | EphB4 | SHVGPIMRAWAP | 39 |
|  | EphB4 | WGIPRAAQVMWT | 40 |
|  | EphB4 | GPVSKAWQETET | 41 |
|  | EphB4 | EFFTWRPTYYGI | 42 |
|  | EphB4 | GPVERAWRPDLI | 43 |
|  | EphB4 | DHNHNLYNPWRL | 44 |
|  | EphB4 | FSPQGPAARNFA | 45 |
|  | EphA4 | NHWLDTLFPMHM | 46 |
| SHW | EphB2 | SHWPISPYSLLS | 47 |
|  | EphB2 | DHWRVSPYSLLY | 48 |
| SNE | EphB2 | SNEWIQPRLPQH | 49 |
| DHW | EphB2 | DHWRILPFSLSS | 50 |
|  | EphB2 | SHWPVLPFAHWQ | 51 |
|  | EphB2 | IHWPVAPYSYLD | 52 |
|  | EphB2 | WHRYPDPRMLPT | 53 |
| WHW | EphB2 | WHWTIEPFAITS | 54 |
|  | EphB2 | THWCHLLNCAAL | 55 |
|  | EphB2 | DHWYYTPWQPIE | 56 |
|  | EphB2 | NHWPTQPYAIPI | 57 |
|  | EphB2 | WPPHWPRSLDYA | 58 |
|  | EphB2 | DHWPLLPYALAH | 59 |
|  | EphB2 | RNKRIRMQLPMI | 60 |
|  | EphA7 | WASHAPYWPHPP | 61 |
|  | EphA7 | KHLPFYPHPTSP | 62 |

Example 10

Binding of the DAL, IPW, and SGH Peptides to EphB4

Figure 17:
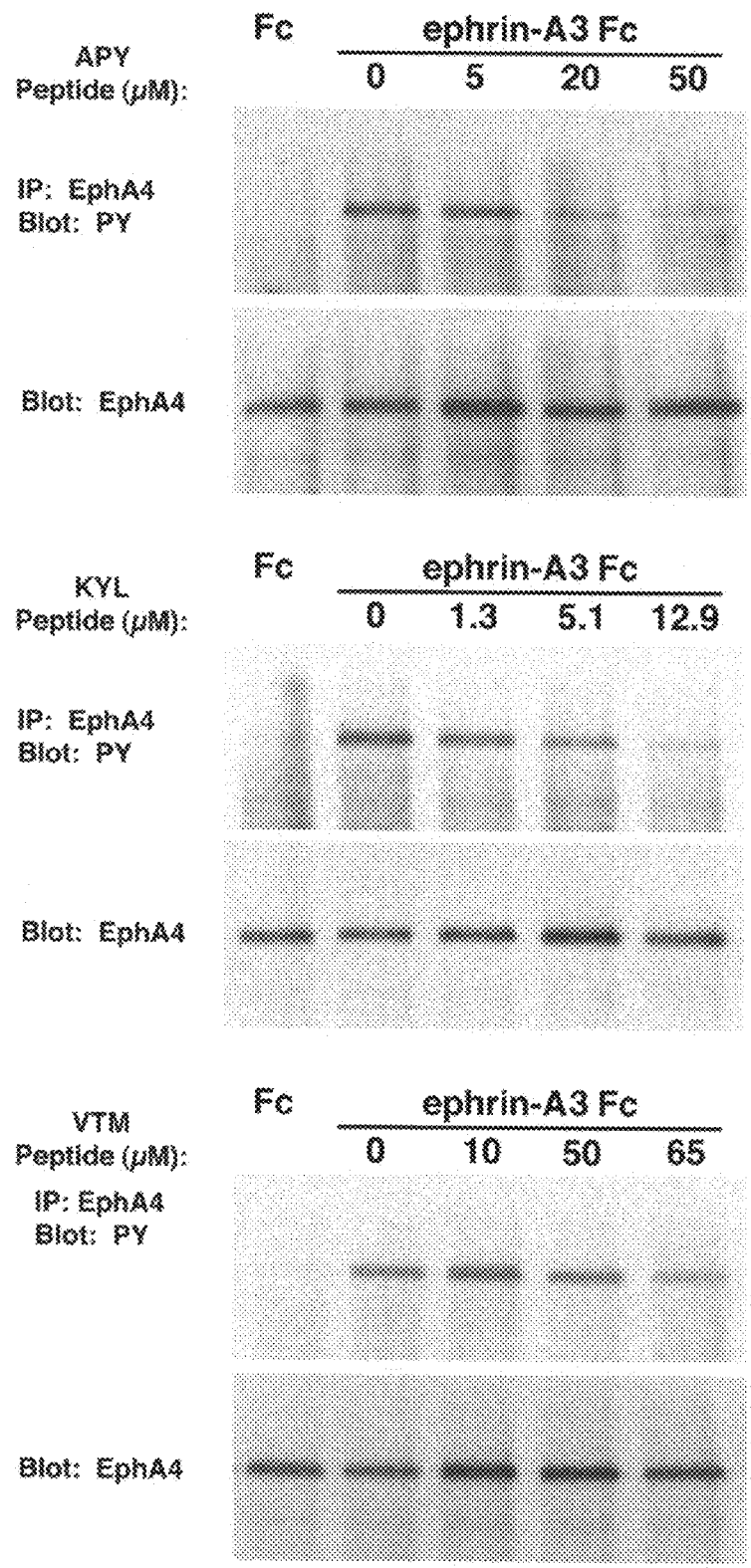
FIG. 17 is a group of immunoblots showing that APY (Panel A), KYL (Panel B), and VTM (Panel C) peptides antagonize ephrin-A3 induced activation of endogenous EphA4 in mouse hippocampal slices.

In this example, methods similar to those used in previous binding characterization experiments were used to show that the phage clones displaying the DAL, IPW, or SGH peptides bound to EphB4 Fc. FIG. 17 shows that each of these phage-displayed peptides bind to EphB4 with a 6- to 10-fold greater affinity than to EphA2. Furthermore, each of the phage-displayed peptides bound EphB4 with a greater affinity than any of the EphA family receptors that were tested (Eph1-Eph7).

Example 11

Specificity of the DAL Peptide for EphB4

In this example, the methods described in Example 2 were used to show that the DAL synthetic peptide binds specifically to EphB4 receptor. When EphB family receptors were incubated with immobilized DAL peptide it was observed that the DAL peptide bound four-fold more EphB4 compared to other EphB family receptors. A similar specificity was observed when EphA family receptors and EphB4 were tested against immobilized DAL peptide.

Example 12

Identification of Peptides that Bind to EphA4

Figure 12A:
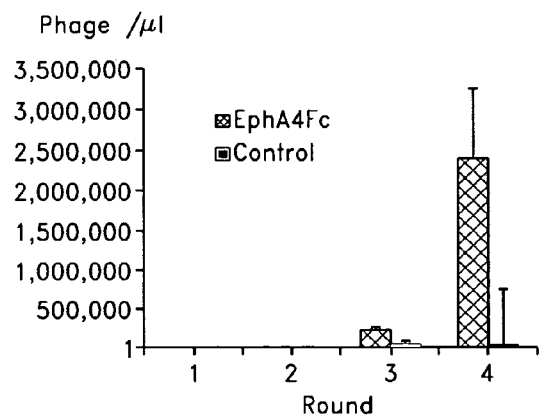
FIGS. 12A and 12E are bar graphs showing identification and binding selectivity of phage clones that target the EphA4 receptor.
Figure 12B:
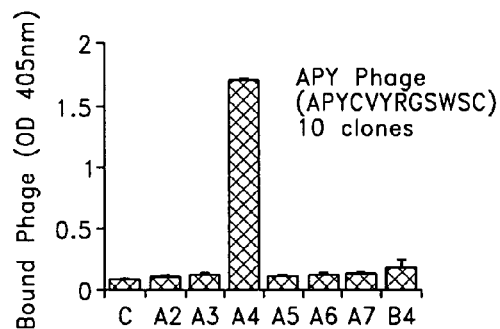
FIG. 12B shows phage clones that display peptides beginning with APY showed preferential binding to EphA4.
Figure 12C:
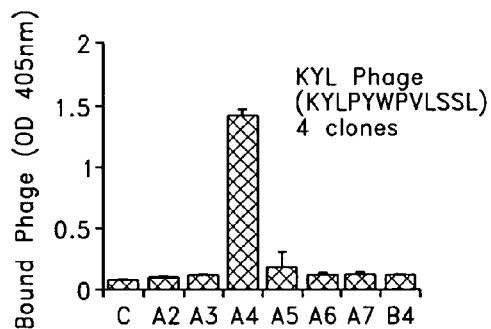
FIG. 12C shows phage clones that display peptides beginning with KYL showed preferential binding to EphA4.
Figure 12D:
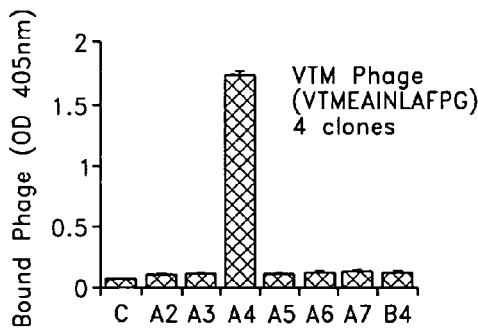
FIG. 12D shows phage clones that display peptides beginning with VTM showed preferential binding to EphA4.
Figure 12E:
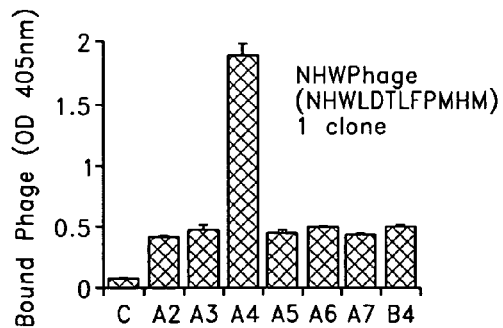

In this example phage display was used to identify peptides that bind to an EphA4 receptor. An M13 phage library displaying random 12-mer peptides was panned on the immobilized EphA4 receptor extracellular domain fused to a human Fc region (FIG. 12A). The phage clones remaining bound to EphA4 were eluted with a low pH solution and amplified. After four rounds of selection on EphA4, an approximately 80-fold enrichment of phage binding to EphA4 compared to a BSA negative control was detected.

Twenty of 38 clones that were tested individually bound to EphA4 Fc but not to an ephrin-A1 Fc negative control. The EphA4-binding clones displayed four different peptide sequences (FIGS. 12B-E). These peptide are referred to as: APY (APYCVYRGSWSC) (SEQ ID NO.: 20), KYL (KYLPYWPVLSSL) (SEQ ID NO.: 21), VTM (VTMEAINLAFPG) (SEQ ID NO.: 22), and NHW (NHWLDTLFPMHM) (SEQ ID NO.: 46). Phage clones displaying these peptides all bound preferentially to EphA4 compared to other EphA or EphB4 receptors (FIGS. 12B-E). However, the NHW phage also exhibited substantial binding to the other Eph receptors tested. Therefore, the three peptides that appeared more selective for EphA4 (APY, KYL, and VTM) were synthesized in order to determine their specificity and functional properties.

Example 13

Three Synthetic Peptides Preferentially Bound to EphA4 with High Affinity

In this example, similar to the phage clones displaying peptide fragments, it was found that the corresponding synthetic peptides preferentially bound to EphA4 in comparison to other EphA receptors. The VTM peptide was highly selective for EphA4, whereas the APY and KYL peptides exhibited some binding to other EphA and EphB receptors (FIG.

13). Equilibrium binding of a soluble EphA4 Fc fusion protein to immobilized peptides shows that EphA4 binds better to the KYL and APY peptides than to the VTM peptide. The apparent binding affinities of the dimeric EphA4 Fc protein to the peptides were in the low nanomolar range, indicating that the EphA4-peptide interactions are of high affinity.

Example 14

The APY, KYL, and VTM Peptides Compete with Each Other for Binding to EphA4

Figure 14:
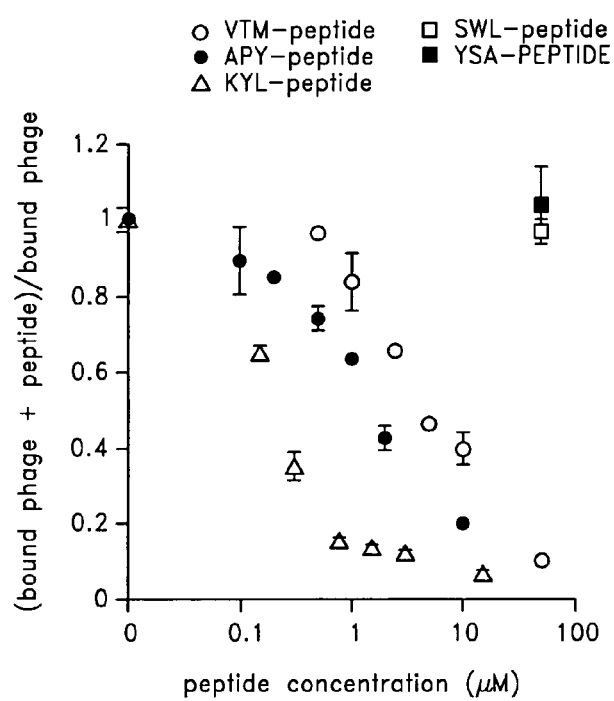
FIG. 14 shows that APY, KYL, and VTM peptides bind to the same or partially overlapping sites on EphA4.
Figure 16A:
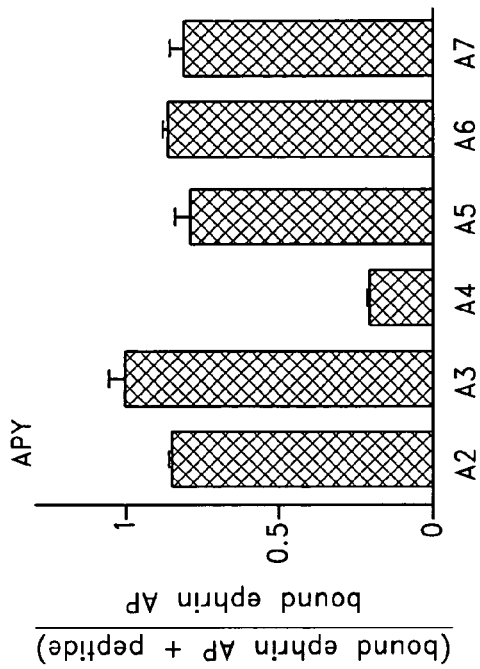
FIGS. 16A-D are bar graphs showing that control (FIG. 16A), APY (FIG. 16B), KYL (FIG. 16C) and VTM (FIG. 16D) peptides preferentially inhibit ephrin-A5 binding to EphA4 compared to the other Eph A receptors.
Figure 16B:
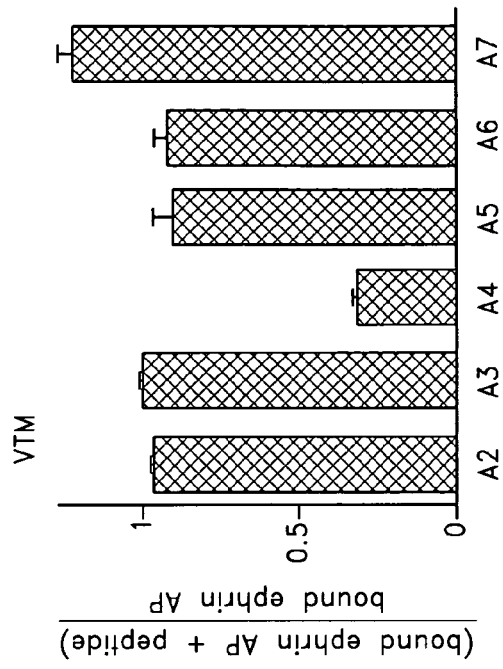
Figure 16C:
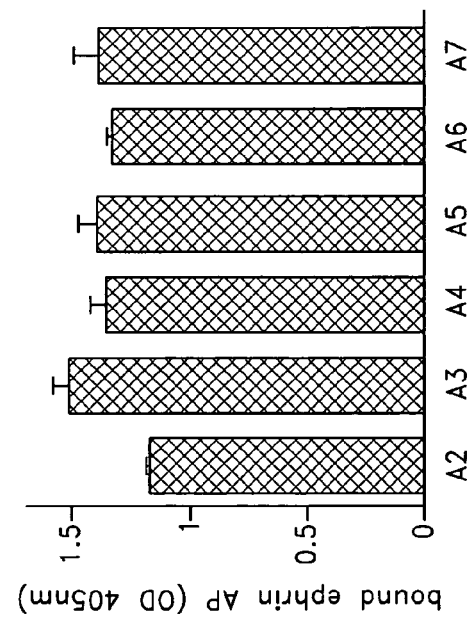
Figure 16D:
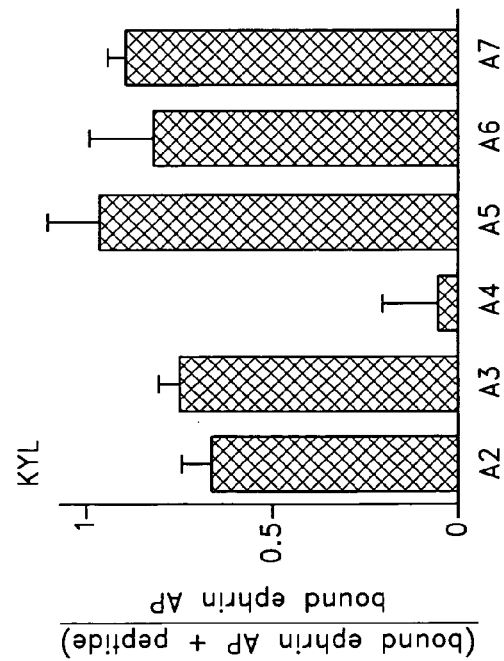

In this example the APY and KYL peptides, which are not closely related in amino acid sequence, were shown to share the motif ΦXXΦ (where Φ indicates an aromatic amino acid and X is any amino acid) (FIG. 19). The sequence of the VTM peptide is dissimilar from both APY and KYL peptides and does not contain the ΦXXΦ motif. Given that the entire multi-domain extracellular region of EphA4 was used for panning, it was conceivable that the peptides may bind to different regions of the receptor. However, experiments in which the three peptides were used to compete with the binding of VTM peptide-displaying phage to immobilized EphA4 showed that all three peptides could antagonize binding of the VTM and APY phage clones (FIG. 14). Thus, all three peptides likely bind to the same or partially overlapping sites on EphA4.

Example 15

The APY, KYL, and VTM Peptides Antagonize Ephrin Binding to EphA4 and Inhibit Ephrin-induced Activation of the Receptor In this example it was found that the ΦXXΦ motif of the APY and KYL peptides is also present in the high affinity receptor-binding site of the ephrin-A ligands and in two previously isolated peptides that inhibit ephrin binding to another EphA receptor (see above and FIG. 19). This indicated that these EphA4-binding peptides may also inhibit ephrin binding. Despite their sequence differences, all three EphA4-binding peptides inhibited binding of alkaline phosphatase-tagged ephrin-A5 (ephrin-A5 AP) to EphA4 in a dose dependent manner (FIG. 15). The KYL peptide was the most effective and almost completely inhibited ephrin binding at a concentration of 1 µM.

Approximately 10 µM of the APY peptide and 100 µM of the VTM peptide were required to achieve similar levels of inhibition. Like the EphA4 binding curves, these inhibition experiments indicate that the KYL peptide has the highest binding affinity and the VTM peptide the lowest. Furthermore, additional peptide inhibition curves at different ephrin concentrations confirmed that the peptides inhibited ephrin binding to the receptor in a competitive manner. Hence, the peptides bind to the ephrin binding site of EphA4 and can be used at micromolar concentrations to inhibit ephrin binding to this receptor. The peptides were also found to preferentially (APY and KYL), or selectively (VTM), block ephrin-A5 AP binding to EphA4 compared to other EphA receptors (FIG. 16). At the peptide concentration used in FIG. 16 (50 µM), however, selectivity for EphA4 was substantial with all three peptides.

To determine if the EphA4-binding peptides inhibit EphA4 activation by the ephrins, or instead activate EphA4, the peptides were applied to hippocampal slices together with ephrin-A3 Fe (Murai, K. K. et al. 2003 Nat Neurosci 6:153-160). Micromolar concentrations of all three peptides were found to antagonize ephrin-A3-induced tyrosine phosphorylation of endogenous EphA4 (FIG. 17). In addition, the peptides did not show the inherent ability to activate the receptor on their own. The KYL peptide blocked EphA4 tyrosine phosphorylation at lower concentrations than the APY and VTM peptides, consistent with its relatively higher binding affinity.

Example 16

The KYL Peptide Perturbs Ephrin/EphA4 Interactions Necessary for the Segmental Migration of Neural Crest Cells In this example to address whether the EphA4-binding peptides can inhibit endogenous ephrin-EphA4 physiological function, a neural crest cell migration assay (McLennan, R. & Krull, C. E. 2002 Gene Expr 10:295-305) was utilized. Chick trunk explants containing premigratory neural crest cells were grown in medium supplemented with 10 µg/ml control Fc, 10 µg/ml EphA4-Fc (positive control), 13 µM KYL peptide, or 13 µM of a control peptide for 24 hours. The migration of neural crest cells was determined by staining for HNK-1 for neural crest cells and ephrin-B1 to label the caudal sclerotome. The KYL peptide was selected because of its apparent high affinity. Neural crest cells migrated properly into the rostral sclerotome in explants treated with control Fc. However, EphA4-Fc treatment caused neural crest cells to abnormally migrate into the caudal half-sclerotome, as previously published (McLennan, R. & Krull, C. E. 2002 Gene Expr 10:295-305). Treatment with the KYL peptide similarly resulted in the ectopic migration of neural crest cells into the caudal half-sclerotome, whereas a control peptide that does not bind to EphA4 had no detectable effect. Thus, the KYL peptide can affect the biological function of endogenous EphA4/ephrin complexes, which enables proper neural crest cell migration.

Example 17

Identification of Peptides that Bind to Two Other EphA Receptors Expressed in Adult Brain: EphA5 and EphA7

In this example additional phage panning experiments were performed to identify peptides that bind to EphA5 and EphA7 (FIG. 18A). EphA5 and EphA7 are two EphA receptors that are closely related to EphA4 but are differentially expressed in the developing and adult nervous system (Ellis, J. et al. 1995 *Mechanisms of Development* 52:319-341; Mori, T. et al 1995 *Brain Res Mol Brain Res* 34:154-160; Olivieri, G. & Miescher, G. C. 1999 *J Histochem Cytochem* 47:855-861; Zhang, J. H. et al 1997 *Brain Res Mol Brain Res* 47:202-214). Three different peptide sequences that bind each receptor were identified. Two of the peptides isolated on EphA5 exhibit selective binding to this receptor (SLRDTYMRAKVL, SEQ ID NO.: 27) and WDCNGPYCHWLG, SEQ ID NO.: 28), while one peptide also binds to EphA6 (WTFPVLWDDKHP, SEQ ID NO.: 29). Of the EphA7-binding pelptides, one also binds to EphA3 (WASHAPYWPHPP, SEQ ID NO.: 61), the second also binds to EphA3 and EphA6 (SVSVGMKPSPRP, SEQ ID NO.: 25), and the third also binds to EphA3, EphA5, and EphA6 (KHLPFYPHPTSP, SEQ ID NO.: 62).

TABLE 2

Phage clones isolated by panning on EphB4

| Peptide sequence | SEQ ID NO | Binding specificity of phage clones | | | | |
|---|---|---|---|---|---|---|
| | | EphB1 | EphB2 | EphB3 | EphB4 | EphB6 |
| GPVADAWLVYPR | 31 | − | − | − | ++++ | − |
| NPVIGPIQRAWT | 32 | − | − | − | ++++ | − |
| DHNHDLYNPWRL | 33 | − | − | − | ++++ | − |
| TNYLFSPNGPIA | 34 | − | − | − | ++++ | − |
| LPHGPVAAAWDA | 35 | − | + | − | ++++ | − |
| TYFDFQAWSIRA | 36 | + | + | + | ++++ | + |
| EWYMKFPPEHYF | 37 | + | + | + | +++ | + |
| GPVHRAWEPTSH | 38 | − | − | + | ++++ | − |
| SHVGPTMRAWAP | 39 | + | − | − | ++++ | − |
| WGIPRAAQVMWT | 40 | + | + | + | ++++ | + |
| GPVSKAWQETET | 41 | − | − | − | +++ | − |
| EFFTWRPTYYGI | 42 | − | − | + | +++ | − |
| GPVERAWRPDLI | 43 | − | − | − | +++ | − |
| DHNHNLYNPWRL | 44 | − | − | − | ++++ | − |
| FSPQGPAARNFA | 45 | − | − | − | ++++ | − |
| DALNDWLLFRPW | 23 | n/a | n/a | n/a | ++++ | n/a |
| IPWTQHMAMSPM | 24 | n/a | n/a | n/a | ++++ | n/a |
| SGHQLLLNKMPN | 26 | n/a | n/a | n/a | ++ | n/a | n/a—not available

TABLE 3

Phage clones isolated by panning on EphB2

| Peptide sequence | SEQ ID NO | Binding specificity of phage clones | | | | |
|---|---|---|---|---|---|---|
| | | EphB1 | EphB2 | EphB3 | EphB4 | EphB6 |
| SHWPISPYSLLS | 47 | +++ | ++++ | + | + | + |
| DHWRVSPYSLLY | 48 | ++++ | ++++ | − | − | − |
| SNEWIQPRLPQH | 49 | − | ++++ | − | − | − |
| DHWRILPFSLSS | 50 | ++++ | ++++ | − | − | − |
| SHWPVLPFAHWQ | 51 | ++++ | ++++ | − | − | − |
| IHWPVAPYSYLD | 52 | ++++ | ++++ | − | − | − |
| WHRYPDPRMLPT | 53 | +++ | ++++ | ++ | + | + |
| WHWTIEPFAITS | 54 | ++++ | ++++ | + | + | ++ |
| THWCHLLNCAAL | 55 | ++++ | ++++ | ++++ | + | + |
| DHWYYTPWQPIE | 56 | + | + | − | − | − |
| NHWPTQPYAIPI | 57 | − | ++++ | − | − | − |
| WPPHWPRSLDYA | 58 | − | +++ | − | − | − |
| DHWPLLPYALAH | 59 | − | +++ | − | − | − |
| RNKRIRMQLPMI | 60 | − | ++++ | − | − | − |

TABLE 4

Binding specificity of selected synthetic peptides

| binding peptides | SEQ ID NO | binding specificity of synthetic peptides | | | | | | | | | | | |
|---|---|---|---|---|---|---|---|---|---|---|---|---|---|
| | | EphB1 | EphB2 | EphB3 | EphB4 | EphB6 | EphA1 | EphA2 | EphA3 | EphA4 | EphA5 | EphA6 | EphA7 | EphA8 |
| EphB4 | | | | | | | | | | | | | | |
| NPVIGPIQRAWT | 32 | − | + | − | ++++ | − | − | − | − | − | − | − | − | − |
| TNYLFSPNGPIA | 34 | − | − | − | ++++ | − | − | − | − | − | − | − | − | − |
| DHNHDLYNPWRL | 33 | − | − | − | ++++ | − | − | − | − | − | − | − | − | − |
| DALNDWLLFRPW | 23 | − | − | − | ++++ | + | − | − | − | + | − | + | − | ++ |
| EphB2 | | | | | | | | | | | | | | |
| SHWPISPYSLLS | 47 | +++ | ++++ | − | − | − | − | − | − | − | − | + | − | − |
| DHWRILPFSLSS | 50 | +++ | ++++ | ++ | − | + | − | + | − | − | − | ++ | − | − |
| WHWTIEPFAITS | 54 | ++++ | ++++ | ++ | + | + | − | ++ | − | − | + | ++ | − | ++ |
| SNEWIQPRLPQH | 49 | + | ++++ | − | − | − | − | − | − | ++ | − | − | − | − |

A panel of novel peptides that target different members of the EphA subclass of receptor tyrosine kinases was identified. This is in contrast to the ephrin ligands, which promiscuously bind to most Eph receptors within the same subclass (Flanagan & Vanderhaeghen 1998 *Ann Rev Neurosci* 21:309-345). Three of the EphA4-binding peptides were further characterized and found to antagonize ephrin binding to EphA4 and block ephrin-induced EphA4 activation and biological function. Since the peptides interfere with ephrin-Eph receptor interactions, they are envisioned to inhibit both forward and reverse signals propagated downstream of EphA4 and its ligands, respectively.

The recently solved crystal structure of an ephrin/Eph receptor complex shows that the receptor binding region of an ephrin contains an extended 15 amino acid loop between α-helices G and H (Himanen J. P. et al. 2001 *Nature* 414:933-938.). Sequence alignments of this G-H loop show that several amino acids are conserved among all the ephrins, while others distinguish the A-ephrins from the B-ephrins and presumably contribute to the specificity for EphA or EphB receptors (FIG. 19). Interestingly, two of the EphA4-binding peptides (APY and KYL peptides) and one of the EphA5-binding peptides (WDC peptide) contained a motif found within the G-H loop of the A-ephrins consisting of two aromatic residues separated by two non-conserved amino acids (ΦXXΦ) (FIG. 19).

This motif was also found to be present in the peptides that bound the EphA2 receptor. A significant number of identified EphB receptor binding peptides had a ΦXXΦ or ΦXXXXΦ motif. The conservation of the $\Phi X_n \Phi$ (n=2-4) motif among peptides that bound different Eph receptors indicates that the two aromatic residues are important for interaction with these receptors and may fit into a conserved region of the ephrin-binding pocket of the Eph receptors, with EphA receptors favoring ΦXXΦ and EphB receptors favoring ΦXXXΦ or ΦXXXXΦ. Residues that flank the aromatic residues are envisioned to provide the specificity for binding to a particular EphA or EphB receptor.

Other amino acid residues are also envisioned to be important for receptor binding and specificity. The APY EphA4-binding peptide and the WDC EphA5-binding peptide contain two cysteine residues that allow these peptides to form an intramolecular disulfide bond. A conformationally constrained cyclic architecture could be important in determining the high binding affinity and receptor-binding selectivity of the peptides. In addition, prolines present in the peptides and the ephrin G-H loop may play a role in Eph receptor binding.

One of the EphA4-binding peptides (VTM peptide) did not show obvious sequence similarities with the other two EphA4-binding peptides. However, EphA4 has unusual ligand specificity because it binds ephrin-B2 and ephrin-B3 in addition to the A-ephrins. Thus, some EphA4-binding peptides may contain amino acids characteristic of the G-H loop of the B-ephrins. Indeed, the VTM peptide contains the sequence Asparagine-Leucine (NL), which is found in the G-H loop of ephrin-B2 and ephrin-B3 (but not ephrin-B1, which does not bind to EphA4) (FIG. 19). Thus, the NL motif is envisioned to be an important site of contact between B-ephrins and EphA4. Alternatively, the phenylalanine (F) in the VTM peptide may correspond to the second aromatic residue of the $\Phi X_n \Phi$ motif, which is conserved in both the A-ephrins and the B-ephrins. Nevertheless, the VTM peptide competitively inhibits ephrin binding, indicating that it binds to the ligand-binding pocket of EphA4.

Example 18

High Throughput Screening Method for Identifying Eph Receptor Binding Agents

High Throughput Screening assays have been used to screen chemical libraries for small molecules that disrupt the Eph receptor-ephrin complex. The assay uses immobilized Eph receptor ectodomains in complex with ephrin-alkaline phosphatase fusion proteins. The ability to decrease bound alkaline phosphatase activity is used to identify small molecule inhibitors of the Eph-ephrin interaction.

Small molecules that target individual Eph receptors and have bioactive properties are useful for both elucidating the function of a receptor and for selectively perturbing the physiology of tissues enriched in that particular receptor. For example, one of the peptides inhibited the interaction between endogenously expressed EphA4 and its ephrin ligands, leading to biological consequences. Selectively inhibiting EphA4 signaling in the hippocampus and the cortex, where this particular receptor is highly expressed, may reduce repulsive ligand-receptor interactions that shape developing, restructuring, or regenerating neurons. Indeed, it has been found that EphA4 signaling maintains the morphology and organization of dendritic spines in the hippocampus (Murai et al. 2003 *Nat Neurosci* 6:153-160). This presumably occurs through transient repulsive contacts with ephrin-A3-positive astrocytes. Interestingly, the peptides block activation of endogenous EphA4 by ephrin-A3 Fc in hippocampal slices. Hence, they may be able to interfere with in vivo ligand-receptor interactions that restrict the expansion of spines. For example, brain injury induces gliosis and this has been correlated with a reduction in the size of dendritic spines, which may occur through activation of EphA4 by glial ephrin-A3 (Thompson, 2003 *Nat Neurosci* 6:103-104.). EphA4-binding peptides are envisioned to counteract some of the inhibitory signals and promote regeneration of functional circuits. On the other hand, engineered peptides capable of activating EphA4 are envisioned to restore the normal shape of elongated dendritic spines in patients with mental retardation.

It is believed that the presence of repulsive and growth inhibitory factors limits the regenerative capacity of the central nervous system. This could be especially important after traumatic brain injury or neuronal degeneration, where blocking non-permissive signals and promoting structural plasticity is desirable. Interestingly, EphA4-binding peptides may promote faster maturation and integration of the newly generated neurons in the dentate gyrus, where neural stem cells persist throughout life to replace lost neurons.

Some of the identified peptides are also envisioned to help the regeneration of injured axons within the spinal cord. Several ephrins and Eph receptors, including EphA4 and EphA7, are upregulated after spinal cord damage or deafferentation (Miranda et al. 1999 *Exp Neurol* 156:218-222; Willson et al. 2002 *Cell Transplantation* 11:229-239). In addition, EphA4 is important for guiding motor axons during development (Eberhart et al. 2002 *Dev Biol* 247:89-101) and establishing the correct trajectories of corticospinal fibers (Dottori et al. 1998 *PNAS USA* 95:13248-13253; Kullander et al. 2001 *Nat Rev Mol Cell Biol* 3:475-486). In these axons, EphA4 is believed to mediate repulsive guidance events. EphA4-mediated repulsion may restrict regrowth of axons in the central nervous system and inhibiting such interactions may promote regeneration.

The EphA receptor-binding peptides are also envisioned to help escort reagents to particular tissues, including damaged regions of the central nervous system that show limited inherent regenerative capability. Coupling pharmaceutical agents to these peptides will allow targeted delivery of molecules that can provide trophic support to degenerating neurons while at the same time attenuating inhibitory constraints for growth. EphA4-binding peptides are useful for selective delivery to brain structures such as the hippocampus and cortex to improve anatomical and cognitive function of patients with neurological disease. EphA5-binding peptides are also useful to deliver reagents to the substantia nigra and cerebellum (Yue et al. 1999 *J Neurosci* 19:2090-2101) and treat neurological diseases affecting these brain regions.

Outside the nervous system, peptide inhibition of EphA4 on platelets is envisioned to have applications for modifying the blood clotting process (Prevost et al. 2002 *PNAS USA* 99:9219-9224). Moreover, these peptides are useful for selectively perturbing EphA4 function in vivo or in vitro for developmental studies, including neural crest cell migration as described here.

EphA receptor-binding peptides are functionally versatile reagents and important tools for treating various diseases and pathologies. They are useful in the context of developmental studies aimed at dissecting the role of EphA receptors in cell migration, axon guidance, and synaptic plasticity as well as for modulating aberrant EphA receptor signaling that may accompany injury to the central nervous system.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:

1. An isolated peptide which selectively binds to the extracellular domain of a member of the Eph receptor family, wherein the isolated peptide comprises the amino acid sequence of SEQ ID NO:2.

2. A composition comprising the isolated peptide of claim 1 linked to p53 or pRB, and a pharmaceutical carrier.

3. A composition comprising:
   the isolated peptide of claim 1 linked to a chemotherapeutic alkylating agent; and
   a pharmaceutical carrier.

4. The composition of claim 3, wherein the chemotherapeutic alkylating agent is melphalan or chlorambucil.

5. A composition comprising:
   the isolated peptide of claim 1 linked to an anti-metabolite compound; and
   a pharmaceutical carrier.

6. The composition of claim 5, wherein the chemotherapeutic anti-metabolite compound is 5-fluorouracil or 5-fluorouridine.

7. The isolated peptide of claim 1, wherein the isolated peptide is capable of inhibiting phosphorylation of MAP kinase (MAPK).

8. The isolated peptide of claim 1, wherein the isolated peptide is capable of stimulating tyrosine phosphorylation of the EphA2 receptor.

9. The isolated peptide of claim 1, wherein said member of the Eph receptor family is EphA2.

10. A composition comprising the isolated peptide of claim 1 linked to a radionuclide selected from the group consisting of $^{90}$Y, $^{67}$Cu, $^{111}$Ln, $^{113m}$Ln, $^{67}$Ga, $^{99m}$Tc, $^{51}$Cr, $^{197}$Hg, $^{203}$Hg, $^{169}$Yb, $^{85}$Sr, and $^{87}$Sr.

11. An isolated peptide which selectively binds to the extracellular domain of a member of the Eph receptor family, wherein the isolated peptide consists of the amino acid sequence of SEQ ID NO:2.

* * * * *

SEQUENCE LISTING

```
<160> NUMBER OF SEQ ID NOS: 71

<210> SEQ ID NO 1
<211> LENGTH: 12
<212> TYPE: PRT
<213> ORGANISM: Artificial Sequence
<220> FEATURE:
<223> OTHER INFORMATION: EphA2-binding peptide

<400> SEQUENCE: 1

Ser Trp Leu Ala Tyr Pro Gly Ala Val Ser Tyr Arg
 1               5                  10

<210> SEQ ID NO 2
<211> LENGTH: 12
<212> TYPE: PRT
<213> ORGANISM: Artificial Sequence
<220> FEATURE:
<223> OTHER INFORMATION: EphA2-binding peptide

<400> SEQUENCE: 2

Tyr Ser Ala Tyr Pro Asp Ser Val Pro Met Met Ser
 1               5                  10

<210> SEQ ID NO 3
<211> LENGTH: 13
<212> TYPE: PRT
<213> ORGANISM: Artificial Sequence
<220> FEATURE:
<223> OTHER INFORMATION: G-H loop portion of hEphrin-A3

<400> SEQUENCE: 3

Arg Tyr Ser Ala Phe Ser Leu Gly Tyr Glu Phe His Ala
 1               5                  10

<210> SEQ ID NO 4
<211> LENGTH: 12
<212> TYPE: PRT
<213> ORGANISM: Artificial Sequence
<220> FEATURE:
<223> OTHER INFORMATION: A3 peptide

<400> SEQUENCE: 4

Tyr Ser Ala Phe Ser Leu Gly Tyr Glu Phe His Ala
 1               5                  10

<210> SEQ ID NO 5
```

```
<211> LENGTH: 13
<212> TYPE: PRT
<213> ORGANISM: Artificial Sequence
<220> FEATURE:
<223> OTHER INFORMATION: G-H loop portion of hEphrin-A2

<400> SEQUENCE: 5

Leu Phe Thr Pro Phe Ser Leu Gly Phe Glu Phe Arg Pro
 1               5                  10

<210> SEQ ID NO 6
<211> LENGTH: 13
<212> TYPE: PRT
<213> ORGANISM: Artificial Sequence
<220> FEATURE:
<223> OTHER INFORMATION: G-H loop portion of hEphrin-A5

<400> SEQUENCE: 6

Leu Phe Thr Pro Phe Ser Leu Gly Phe Glu Phe Arg Pro
 1               5                  10

<210> SEQ ID NO 7
<211> LENGTH: 13
<212> TYPE: PRT
<213> ORGANISM: Artificial Sequence
<220> FEATURE:
<223> OTHER INFORMATION: G-H loop portion of CEphrin-A6

<400> SEQUENCE: 7

Arg Phe Thr Pro Phe Ser Leu Gly Phe Glu Phe Arg Pro
 1               5                  10

<210> SEQ ID NO 8
<211> LENGTH: 13
<212> TYPE: PRT
<213> ORGANISM: Artificial Sequence
<220> FEATURE:
<223> OTHER INFORMATION: G-H loop portion of hEphrin-A1

<400> SEQUENCE: 8

Arg Phe Thr Pro Phe Thr Leu Gly Lys Glu Phe Lys Glu
 1               5                  10

<210> SEQ ID NO 9
<211> LENGTH: 13
<212> TYPE: PRT
<213> ORGANISM: Artificial Sequence
<220> FEATURE:
<223> OTHER INFORMATION: G-H loop portion of hEphrin-A4

<400> SEQUENCE: 9

Arg Phe Thr Pro Phe Ser Leu Gly Phe Glu Phe Leu Pro
 1               5                  10

<210> SEQ ID NO 10
<211> LENGTH: 12
<212> TYPE: PRT
<213> ORGANISM: Artificial Sequence
<220> FEATURE:
<223> OTHER INFORMATION: Reverse sequence of SWL peptide

<400> SEQUENCE: 10

Arg Tyr Ser Val Ala Gly Pro Tyr Ala Leu Trp Ser
 1               5                  10

<210> SEQ ID NO 11
<211> LENGTH: 12
<212> TYPE: PRT
```

<213> ORGANISM: Artificial Sequence
<220> FEATURE:
<223> OTHER INFORMATION: Reverse sequence of YSA peptide

<400> SEQUENCE: 11

Ser Met Met Pro Val Ser Asp Pro Tyr Ala Ser Tyr
1 5 10

<210> SEQ ID NO 12
<211> LENGTH: 13
<212> TYPE: PRT
<213> ORGANISM: Artificial Sequence
<220> FEATURE:
<223> OTHER INFORMATION: A-A' Beta-strand portion of hEphrin-A5

<400> SEQUENCE: 12

Gly Ser Lys Ala Val Ala Asp Arg Tyr Ala Val Tyr Trp
1 5 10

<210> SEQ ID NO 13
<211> LENGTH: 11
<212> TYPE: PRT
<213> ORGANISM: Artificial Sequence
<220> FEATURE:
<223> OTHER INFORMATION: A5 peptide

<400> SEQUENCE: 13

Lys Ala Val Ala Asp Arg Tyr Ala Val Tyr Trp
1 5 10

<210> SEQ ID NO 14
<211> LENGTH: 13
<212> TYPE: PRT
<213> ORGANISM: Artificial Sequence
<220> FEATURE:
<223> OTHER INFORMATION: A-A' Beta-strand portion of hEphrin-A2

<400> SEQUENCE: 14

Ala Ala Arg Ala Asn Ala Asp Arg Tyr Ala Val Tyr Trp
1 5 10

<210> SEQ ID NO 15
<211> LENGTH: 13
<212> TYPE: PRT
<213> ORGANISM: Artificial Sequence
<220> FEATURE:
<223> OTHER INFORMATION: A-A' Beta-strand portion of hEphrin-A4

<400> SEQUENCE: 15

Leu Arg Gly Gly Ser Ser Leu Arg His Val Val Tyr Trp
1 5 10

<210> SEQ ID NO 16
<211> LENGTH: 13
<212> TYPE: PRT
<213> ORGANISM: Artificial Sequence
<220> FEATURE:
<223> OTHER INFORMATION: A-A' Beta-strand portion of hEphrin-A1

<400> SEQUENCE: 16

Gly Ser Leu Ala Ala Ala Asp Arg His Thr Val Phe Trp
1 5 10

<210> SEQ ID NO 17
<211> LENGTH: 13
<212> TYPE: PRT
<213> ORGANISM: Artificial Sequence
<220> FEATURE:

```
-continued

<223> OTHER INFORMATION: A-A' Beta-strand portion of hEphrin-A3

<400> SEQUENCE: 17

Pro Gly Gly Ala Leu Gly Asn Arg His Ala Val Tyr Trp
1               5                   10

<210> SEQ ID NO 18
<211> LENGTH: 13
<212> TYPE: PRT
<213> ORGANISM: Artificial Sequence
<220> FEATURE:
<223> OTHER INFORMATION: A-A' Beta-strand portion of cEphrin-A6

<400> SEQUENCE: 18

Pro Pro Pro Val Arg Gly Arg Arg His Gly Val Tyr Trp
1               5                   10

<210> SEQ ID NO 19
<211> LENGTH: 15
<212> TYPE: PRT
<213> ORGANISM: Artificial Sequence
<220> FEATURE:
<223> OTHER INFORMATION: extended A5 peptide

<400> SEQUENCE: 19

Val Ala Asp Arg Tyr Ala Val Tyr Trp Asn Ser Ser Asn Pro Arg
1               5                   10                  15

<210> SEQ ID NO 20
<211> LENGTH: 12
<212> TYPE: PRT
<213> ORGANISM: Artificial Sequence
<220> FEATURE:
<223> OTHER INFORMATION: APY peptide

<400> SEQUENCE: 20

Ala Pro Tyr Cys Val Tyr Arg Gly Ser Trp Ser Cys
1               5                   10

<210> SEQ ID NO 21
<211> LENGTH: 12
<212> TYPE: PRT
<213> ORGANISM: Artificial Sequence
<220> FEATURE:
<223> OTHER INFORMATION: KYL peptide

<400> SEQUENCE: 21

Lys Tyr Leu Pro Tyr Trp Pro Val Leu Ser Ser Leu
1               5                   10

<210> SEQ ID NO 22
<211> LENGTH: 12
<212> TYPE: PRT
<213> ORGANISM: Artificial Sequence
<220> FEATURE:
<223> OTHER INFORMATION: VTM peptide

<400> SEQUENCE: 22

Val Thr Met Glu Ala Ile Asn Leu Ala Phe Pro Gly
1               5                   10

<210> SEQ ID NO 23
<211> LENGTH: 12
<212> TYPE: PRT
<213> ORGANISM: Artificial Sequence
<220> FEATURE:
<223> OTHER INFORMATION: DAL peptide
```

```
<400> SEQUENCE: 23

Asp Ala Leu Asn Asp Trp Leu Leu Phe Arg Pro Trp
1               5                   10

<210> SEQ ID NO 24
<211> LENGTH: 12
<212> TYPE: PRT
<213> ORGANISM: Artificial Sequence
<220> FEATURE:
<223> OTHER INFORMATION: IPW peptide

<400> SEQUENCE: 24

Ile Pro Trp Thr Gln His Met Ala Met Ser Pro Met
1               5                   10

<210> SEQ ID NO 25
<211> LENGTH: 12
<212> TYPE: PRT
<213> ORGANISM: Artificial Sequence
<220> FEATURE:
<223> OTHER INFORMATION: SVS peptide

<400> SEQUENCE: 25

Ser Val Ser Val Gly Met Lys Pro Ser Pro Arg Pro
1               5                   10

<210> SEQ ID NO 26
<211> LENGTH: 12
<212> TYPE: PRT
<213> ORGANISM: Artificial Sequence
<220> FEATURE:
<223> OTHER INFORMATION: SGH peptide

<400> SEQUENCE: 26

Ser Gly His Gln Leu Leu Leu Asn Lys Met Pro Asn
1               5                   10

<210> SEQ ID NO 27
<211> LENGTH: 12
<212> TYPE: PRT
<213> ORGANISM: Artificial Sequence
<220> FEATURE:
<223> OTHER INFORMATION: SLR peptide

<400> SEQUENCE: 27

Ser Leu Arg Asp Thr Tyr Met Arg Ala Lys Val Leu
1               5                   10

<210> SEQ ID NO 28
<211> LENGTH: 12
<212> TYPE: PRT
<213> ORGANISM: Artificial Sequence
<220> FEATURE:
<223> OTHER INFORMATION: WDC peptide

<400> SEQUENCE: 28

Trp Asp Cys Asn Gly Pro Tyr Cys His Trp Leu Gly
1               5                   10

<210> SEQ ID NO 29
<211> LENGTH: 12
<212> TYPE: PRT
<213> ORGANISM: Artificial Sequence
<220> FEATURE:
<223> OTHER INFORMATION: WTF peptide

<400> SEQUENCE: 29
```

-continued

Trp Thr Phe Pro Val Leu Trp Asp Asp Lys His Pro
1               5                   10

<210> SEQ ID NO 30
<211> LENGTH: 5
<212> TYPE: PRT
<213> ORGANISM: Artificial Sequence
<220> FEATURE:
<223> OTHER INFORMATION: Carboxy terminal linker

<400> SEQUENCE: 30

Gly Ser Gly Ser Lys
1               5

<210> SEQ ID NO 31
<211> LENGTH: 12
<212> TYPE: PRT
<213> ORGANISM: Artificial Sequence
<220> FEATURE:
<223> OTHER INFORMATION: EphB4-binding peptide

<400> SEQUENCE: 31

Gly Pro Val Ala Asp Ala Trp Leu Val Tyr Pro Arg
1               5                   10

<210> SEQ ID NO 32
<211> LENGTH: 12
<212> TYPE: PRT
<213> ORGANISM: Artificial Sequence
<220> FEATURE:
<223> OTHER INFORMATION: EphB4-binding peptide

<400> SEQUENCE: 32

Asn Pro Val Ile Gly Pro Ile Gln Arg Ala Trp Thr
1               5                   10

<210> SEQ ID NO 33
<211> LENGTH: 12
<212> TYPE: PRT
<213> ORGANISM: Artificial Sequence
<220> FEATURE:
<223> OTHER INFORMATION: EphB4-binding peptide

<400> SEQUENCE: 33

Asp His Asn His Asp Leu Tyr Asn Pro Trp Arg Leu
1               5                   10

<210> SEQ ID NO 34
<211> LENGTH: 12
<212> TYPE: PRT
<213> ORGANISM: Artificial Sequence
<220> FEATURE:
<223> OTHER INFORMATION: EphB4-binding peptide

<400> SEQUENCE: 34

Thr Asn Tyr Leu Phe Ser Pro Asn Gly Pro Ile Ala
1               5                   10

<210> SEQ ID NO 35
<211> LENGTH: 12
<212> TYPE: PRT
<213> ORGANISM: Artificial Sequence
<220> FEATURE:
<223> OTHER INFORMATION: EphB4-binding peptide

<400> SEQUENCE: 35

Leu Pro His Gly Pro Val Ala Ala Ala Trp Asp Ala
1               5                   10

```
<210> SEQ ID NO 36
<211> LENGTH: 12
<212> TYPE: PRT
<213> ORGANISM: Artificial Sequence
<220> FEATURE:
<223> OTHER INFORMATION: EphB4-binding peptide

<400> SEQUENCE: 36

Thr Tyr Phe Asp Phe Gln Ala Trp Ser Ile Arg Ala
1               5                   10

<210> SEQ ID NO 37
<211> LENGTH: 12
<212> TYPE: PRT
<213> ORGANISM: Artificial Sequence
<220> FEATURE:
<223> OTHER INFORMATION: EphB4-binding peptide

<400> SEQUENCE: 37

Glu Trp Tyr Met Lys Phe Pro Pro Glu His Tyr Phe
1               5                   10

<210> SEQ ID NO 38
<211> LENGTH: 12
<212> TYPE: PRT
<213> ORGANISM: Artificial Sequence
<220> FEATURE:
<223> OTHER INFORMATION: EphB4-binding peptide

<400> SEQUENCE: 38

Gly Pro Val His Arg Ala Trp Glu Pro Thr Ser His
1               5                   10

<210> SEQ ID NO 39
<211> LENGTH: 12
<212> TYPE: PRT
<213> ORGANISM: Artificial Sequence
<220> FEATURE:
<223> OTHER INFORMATION: EphB4-binding peptide

<400> SEQUENCE: 39

Ser His Val Gly Pro Ile Met Arg Ala Trp Ala Pro
1               5                   10

<210> SEQ ID NO 40
<211> LENGTH: 12
<212> TYPE: PRT
<213> ORGANISM: Artificial Sequence
<220> FEATURE:
<223> OTHER INFORMATION: EphB4-binding peptide

<400> SEQUENCE: 40

Trp Gly Ile Pro Arg Ala Ala Gln Val Met Trp Thr
1               5                   10

<210> SEQ ID NO 41
<211> LENGTH: 12
<212> TYPE: PRT
<213> ORGANISM: Artificial Sequence
<220> FEATURE:
<223> OTHER INFORMATION: EphB4-binding peptide

<400> SEQUENCE: 41

Gly Pro Val Ser Lys Ala Trp Gln Glu Thr Glu Thr
1               5                   10
```

-continued

```
<210> SEQ ID NO 42
<211> LENGTH: 12
<212> TYPE: PRT
<213> ORGANISM: Artificial Sequence
<220> FEATURE:
<223> OTHER INFORMATION: EphB4-binding peptide

<400> SEQUENCE: 42

Glu Phe Phe Thr Trp Arg Pro Thr Tyr Tyr Gly Ile
1               5                   10

<210> SEQ ID NO 43
<211> LENGTH: 12
<212> TYPE: PRT
<213> ORGANISM: Artificial Sequence
<220> FEATURE:
<223> OTHER INFORMATION: EphB4-binding peptide

<400> SEQUENCE: 43

Gly Pro Val Glu Arg Ala Trp Arg Pro Asp Leu Ile
1               5                   10

<210> SEQ ID NO 44
<211> LENGTH: 12
<212> TYPE: PRT
<213> ORGANISM: Artificial Sequence
<220> FEATURE:
<223> OTHER INFORMATION: EphB4-binding peptide

<400> SEQUENCE: 44

Asp His Asn His Asn Leu Tyr Asn Pro Trp Arg Leu
1               5                   10

<210> SEQ ID NO 45
<211> LENGTH: 12
<212> TYPE: PRT
<213> ORGANISM: Artificial Sequence
<220> FEATURE:
<223> OTHER INFORMATION: EphB4-binding peptide

<400> SEQUENCE: 45

Phe Ser Pro Gln Gly Pro Ala Ala Arg Asn Phe Ala
1               5                   10

<210> SEQ ID NO 46
<211> LENGTH: 12
<212> TYPE: PRT
<213> ORGANISM: Artificial Sequence
<220> FEATURE:
<223> OTHER INFORMATION: EphA4-binding peptide

<400> SEQUENCE: 46

Asn His Trp Leu Asp Thr Leu Phe Pro Met His Met
1               5                   10

<210> SEQ ID NO 47
<211> LENGTH: 12
<212> TYPE: PRT
<213> ORGANISM: Artificial Sequence
<220> FEATURE:
<223> OTHER INFORMATION: EphB2-binding peptide

<400> SEQUENCE: 47

Ser His Trp Pro Ile Ser Pro Tyr Ser Leu Leu Ser
1               5                   10

<210> SEQ ID NO 48
<211> LENGTH: 12
```

```
<212> TYPE: PRT
<213> ORGANISM: Artificial Sequence
<220> FEATURE:
<223> OTHER INFORMATION: EphB2-binding peptide

<400> SEQUENCE: 48

Asp His Trp Arg Val Ser Pro Tyr Ser Leu Leu Tyr
1               5                   10

<210> SEQ ID NO 49
<211> LENGTH: 12
<212> TYPE: PRT
<213> ORGANISM: Artificial Sequence
<220> FEATURE:
<223> OTHER INFORMATION: EphB2-binding peptide

<400> SEQUENCE: 49

Ser Asn Glu Trp Ile Gln Pro Arg Leu Pro Gln His
1               5                   10

<210> SEQ ID NO 50
<211> LENGTH: 12
<212> TYPE: PRT
<213> ORGANISM: Artificial Sequence
<220> FEATURE:
<223> OTHER INFORMATION: EphB2-binding peptide

<400> SEQUENCE: 50

Asp His Trp Arg Ile Leu Pro Phe Ser Leu Ser Ser
1               5                   10

<210> SEQ ID NO 51
<211> LENGTH: 12
<212> TYPE: PRT
<213> ORGANISM: Artificial Sequence
<220> FEATURE:
<223> OTHER INFORMATION: EphB2-binding peptide

<400> SEQUENCE: 51

Ser His Trp Pro Val Leu Pro Phe Ala His Trp Gln
1               5                   10

<210> SEQ ID NO 52
<211> LENGTH: 12
<212> TYPE: PRT
<213> ORGANISM: Artificial Sequence
<220> FEATURE:
<223> OTHER INFORMATION: EphB2-binding peptide

<400> SEQUENCE: 52

Ile His Trp Pro Val Ala Pro Tyr Ser Tyr Leu Asp
1               5                   10

<210> SEQ ID NO 53
<211> LENGTH: 12
<212> TYPE: PRT
<213> ORGANISM: Artificial Sequence
<220> FEATURE:
<223> OTHER INFORMATION: EphB2-binding peptide

<400> SEQUENCE: 53

Trp His Arg Tyr Pro Asp Pro Arg Met Leu Pro Thr
1               5                   10

<210> SEQ ID NO 54
<211> LENGTH: 12
<212> TYPE: PRT
<213> ORGANISM: Artificial Sequence
```

```
<220> FEATURE:
<223> OTHER INFORMATION: EphB2-binding peptide

<400> SEQUENCE: 54

Trp His Trp Thr Ile Glu Pro Phe Ala Ile Thr Ser
 1               5                  10

<210> SEQ ID NO 55
<211> LENGTH: 12
<212> TYPE: PRT
<213> ORGANISM: Artificial Sequence
<220> FEATURE:
<223> OTHER INFORMATION: EphB2-binding peptide

<400> SEQUENCE: 55

Thr His Trp Cys His Leu Leu Asn Cys Ala Ala Leu
 1               5                  10

<210> SEQ ID NO 56
<211> LENGTH: 12
<212> TYPE: PRT
<213> ORGANISM: Artificial Sequence
<220> FEATURE:
<223> OTHER INFORMATION: EphB2-binding peptide

<400> SEQUENCE: 56

Asp His Trp Tyr Tyr Thr Pro Trp Gln Pro Ile Glu
 1               5                  10

<210> SEQ ID NO 57
<211> LENGTH: 12
<212> TYPE: PRT
<213> ORGANISM: Artificial Sequence
<220> FEATURE:
<223> OTHER INFORMATION: EphB2-binding peptide

<400> SEQUENCE: 57

Asn His Trp Pro Thr Gln Pro Tyr Ala Ile Pro Ile
 1               5                  10

<210> SEQ ID NO 58
<211> LENGTH: 12
<212> TYPE: PRT
<213> ORGANISM: Artificial Sequence
<220> FEATURE:
<223> OTHER INFORMATION: EphB2-binding peptide

<400> SEQUENCE: 58

Trp Pro Pro His Trp Pro Arg Ser Leu Asp Tyr Ala
 1               5                  10

<210> SEQ ID NO 59
<211> LENGTH: 12
<212> TYPE: PRT
<213> ORGANISM: Artificial Sequence
<220> FEATURE:
<223> OTHER INFORMATION: EphB2-binding peptide

<400> SEQUENCE: 59

Asp His Trp Pro Leu Leu Pro Tyr Ala Leu Ala His
 1               5                  10

<210> SEQ ID NO 60
<211> LENGTH: 12
<212> TYPE: PRT
<213> ORGANISM: Artificial Sequence
<220> FEATURE:
<223> OTHER INFORMATION: EphB2-binding peptide
```

<400> SEQUENCE: 60

Arg Asn Lys Arg Ile Arg Met Gln Leu Pro Met Ile
1               5                   10

<210> SEQ ID NO 61
<211> LENGTH: 12
<212> TYPE: PRT
<213> ORGANISM: Artificial Sequence
<220> FEATURE:
<223> OTHER INFORMATION: EphA7-binding peptide

<400> SEQUENCE: 61

Trp Ala Ser His Ala Pro Tyr Trp Pro His Pro Pro
1               5                   10

<210> SEQ ID NO 62
<211> LENGTH: 12
<212> TYPE: PRT
<213> ORGANISM: Artificial Sequence
<220> FEATURE:
<223> OTHER INFORMATION: EphA7-binding peptide

<400> SEQUENCE: 62

Lys His Leu Pro Phe Tyr Pro His Pro Thr Ser Pro
1               5                   10

<210> SEQ ID NO 63
<211> LENGTH: 15
<212> TYPE: PRT
<213> ORGANISM: Homo sapiens

<400> SEQUENCE: 63

Gln Arg Phe Thr Pro Phe Thr Leu Gly Lys Glu Phe Lys Glu Gly
1               5                   10                  15

<210> SEQ ID NO 64
<211> LENGTH: 15
<212> TYPE: PRT
<213> ORGANISM: Homo sapiens

<400> SEQUENCE: 64

Gln Leu Phe Thr Pro Phe Ser Leu Gly Phe Glu Phe Arg Pro Gly
1               5                   10                  15

<210> SEQ ID NO 65
<211> LENGTH: 15
<212> TYPE: PRT
<213> ORGANISM: Homo sapiens

<400> SEQUENCE: 65

Gln Arg Tyr Ser Ala Phe Ser Leu Gly Tyr Glu Phe His Ala Gly
1               5                   10                  15

<210> SEQ ID NO 66
<211> LENGTH: 15
<212> TYPE: PRT
<213> ORGANISM: Homo sapiens

<400> SEQUENCE: 66

Gln Arg Phe Thr Pro Phe Ser Leu Gly Phe Glu Phe Leu Pro Gly
1               5                   10                  15

<210> SEQ ID NO 67
<211> LENGTH: 15
<212> TYPE: PRT

```
<213> ORGANISM: Homo sapiens

<400> SEQUENCE: 67

Gln Leu Phe Thr Pro Phe Ser Leu Gly Phe Glu Phe Arg Pro Gly
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: cEphrin-A6 peptide

<400> SEQUENCE: 68

Gln Arg Phe Thr Pro Phe Ser Leu Gly Phe Glu Phe Arg Pro Gly
1               5                   10                  15

<210> SEQ ID NO 69
<211> LENGTH: 15
<212> TYPE: PRT
<213> ORGANISM: Homo sapiens

<400> SEQUENCE: 69

Gln Glu Phe Ser Pro Asn Tyr Met Gly Leu Glu Phe Lys Lys His
1               5                   10                  15

<210> SEQ ID NO 70
<211> LENGTH: 15
<212> TYPE: PRT
<213> ORGANISM: Homo sapiens

<400> SEQUENCE: 70

Gln Glu Phe Ser Pro Asn Leu Trp Gly Leu Glu Phe Gln Lys Asn
1               5                   10                  15

<210> SEQ ID NO 71
<211> LENGTH: 15
<212> TYPE: PRT
<213> ORGANISM: Homo sapiens

<400> SEQUENCE: 71

Gln Glu Tyr Ser Pro Asn Leu Trp Gly His Glu Phe Arg Ser His
1               5                   10                  15
```